United States Patent [19]
Jarrell

[11] Patent Number: 5,498,531
[45] Date of Patent: Mar. 12, 1996

[54] INTRON-MEDIATED RECOMBINANT TECHNIQUES AND REAGENTS

[75] Inventor: Kevin A. Jarrell, Arlington, Mass.

[73] Assignee: President and Fellows of Harvard College, Cambridge, Mass.

[21] Appl. No.: 119,512

[22] Filed: Sep. 10, 1993

[51] Int. Cl.$^6$ .......................... C12N 15/11; C12N 15/13; C12P 19/34

[52] U.S. Cl. .................................. 435/91.31; 435/91.32; 435/91.3; 435/91.5; 536/23.1; 536/23.5; 536/23.53

[58] Field of Search .................................. 435/69.1, 91.1, 435/91.3, 91.31, 91.4, 91.42, 91.5, 91.51, 172.3, 172.1, 235.1; 536/23.1, 23.2, 23.4, 23.5, 23.7, 23.53

[56] References Cited

U.S. PATENT DOCUMENTS

| | | | |
|---|---|---|---|
| 5,037,746 | 8/1991 | Cech et al. | 435/91.31 |
| 5,223,409 | 6/1993 | Ladner et al. | 435/69.7 |

FOREIGN PATENT DOCUMENTS 9207075  4/1992  WIPO.

OTHER PUBLICATIONS

Agabian et al., "Trans Splicing of Nuclear Pre–mRNAs" *Cell*, vol. 61, pp. 1157–1160, Jun. 29, 1990.
Augustin et al., "Reverse self–splicing of group II intron RNAs in vitro" *Nature*, vol. 343, pp. 383–386, Jan. 25, 1990.
Bonen et al., "Trans–splicing of pre–mRNA in plants, animals, and protists" The *FASEB Journal*, vol. 7, pp. 40–46, Jan. 1993.
Buckler et al., "Exon amplification: A strategy to isolate mammalian genes based on RNA splicing" *Proceedings of the National Academy of Sciences*, vol. 88, pp. 4005–4009, May 1991.
Burgess et al., "A Mechanism to Enhance mRNA Splicing Fidelity: The RNA–Dependent ATPase Prp16 Usage of A Discard Pathway for Aberrant Lariat Intermediates" *Cell*, vol. 73, pp. 1377–1391, Jul. 2, 1993.
Burke et al., "Sequences and Classification of Group I and Group II Introns" *Methods in Enzymology*, vol. 180, pp. 533–545, 1989.
Bryk et al., "Spontaneous shuffling of domains between introns of phage T4" *Nature*, vol. 346, pp. 394–396, Jul. 26, 1990.
Cech et al., "Self–Splicing of Group I Introns" *Annu. rev. Biochem.*, vol. 59, pp. 543–568, 1990.
Cripe et al., "Structure of the Gene for Human Coagulation Factor V" *Biochemistry*, vol. 31, pp. 3777–3785, 1992.
De Vries et al., "Artificial Exon Shuffling between Tissue–Type Plasminogen Activator (t–PA) and Urokinase (u–PA): A Comparative Study on the Fibrinolytic Properties of t–PA/u–PA Hybrid Proteins" *Biochemistry*, vol. 27, pp. 2565–2572, 1988.
Dorit et al., "How Big Is the Universe of Exons?" *Science*, vol. 250, pp. 1377–1382, Dec. 7, 1990.
Dib–Hajj et al., "Domain 5 interacts with domain 6 and influences the second transesterification reaction of group II intron self–spacing" *Nucleic Acid Research*, vol. 21, No. 8, pp. 1797–1804, 1993.
Doudna et al., "RNA structure not sequence, determines the 5' splice–site specificity of a group I intron" *Proceedings of the National Academy of Sciences*, vol. 86, pp. 7402–7406, Oct. 1989.
Fedorov et al., "Analysis of nonuniformity in intorn phase distribution" *Nucleic Acid Research*, vol. 20, No. 10, pp. 2553–2557, 1992.
Franzen et al., "Kinetic analysis of the 5' splice junction hydrolysis of a group II intron promoted by domain 5" *Nucleic Acid Research*, vol. 21, No. 3, pp. 627–634, 1993.
Galloway et al., "Deletion–tolerance and Trans–splicing of the Bacteriophage T4 td Intron" *J. Mol. Biol.*, vol. 211, pp. 537–549, 1990.
Hall et al., "Exon shuffling by recombination between self–splicing introns of bacteriophage T4" *Nature*, vol. 340, pp. 574–576, Aug. 17, 1989.
Jacquier et al., "Efficient Trans–Splicing of a Yeast Mitochondrial RNA Group II Intron Implicates a Strong 5' Exon–Intron Interaction" *Science*, vol. 234, pp. 1099–1104, Nov. 28, 1986.
Jacquier et al., "multiple Exon–Binding Sites in Class II Self–Splicing Introns" *Cell*, vol. 50, pp. 17–29, Jul. 3, 1987.
Jarrell et al., "Group II Intron Domain 5 Facilitates a trans–Splicing Reaction" *Molecullar and Cellular Biology*, vol. 8, No. 6, pp. 2361–2366, Jun. 1988.
Jarrell et al., "Group II Intron Self–splicing" *The Journal of Biological Chemistry*, vol. 263, No. 7, pp. 3432–3439, Mar. 5, 1988.
Kim et al., "Pre–mRNA splicing within an assembled yeast spliceosome requires an RNA–dependent ATPase and ATP hydrolysis" *Proceedings of the National Academy of Sciences*, vol. 90, pp. 888–892, Feb. 1993.
Koch et al., "Group II Introns Deleted for Multiple Substructures Retain Self–Splicing Activity" *Molecular and Cellular Biology*, vol. 12, No. 5, pp. 1950–1958, May 1992.
Konarska et al., "Trans Splicing of mRNA Precursors In (List continued on next page.)

Primary Examiner—Mindy Fleisher
Assistant Examiner—Philip W. Carter
Attorney, Agent, or Firm—Matthew P. Vincent; Giulio A. DeConti, Jr.; Lahive & Cockfield

[57] ABSTRACT

The present invention makes available methods and reagents for novel manipulation of nucleic acids. As described herein, the present invention makes use of the ability of intronic sequences, such as derived from group I, group II, or nuclear pre-mRNA introns, to mediate specific cleavage and ligation of discontinuous nucleic acid molecules. For example, novel genes and gene products can be generated by admixing nucleic acid constructs which comprise exon nucleic acid sequences flanked by intron sequences that can direct trans-splicing of the exon sequences to each other. The flanking intronic sequences can, by intermolecular complementation, form a reactive complex which promotes the transesterification reactions necessary to cause the ligation of discontinuous nucleic acid sequences to one another, and thereby generate a recombinant gene comprising the ligated exons.

37 Claims, 19 Drawing Sheets

OTHER PUBLICATIONS

Vitro" *Cell*, vol. 42, pp. 165–171, Aug. 1985.

Langer–Safer et al., "Replacement of Finger and Growth Factor Domains of Tissue Plasminogen Activator with Plasminogen Kringle 1" *The Journal of Biological Chemistry*, vol. 266, No. 6, pp. 3715–3723, Feb. 25, 1991.

Michel et al., "Comparative and functional anatomy of group II catalytic introns: a review" *Gene*, vol. 82, pp. 5–30, 1989.

Mörl et al., "Group II intron RNA–catalyzed recombination of RNA in vitro" *Nucleic Acids Research*, vol. 18, No. 22, pp. 6545–6551, 1990.

Mörl et al., "New reactions Catalyzed by a Group II Intron Ribozyme with RNA and DNA Substrates" *Cell*, vol. 70, pp. 803–810, Sep. 4, 1992.

Mörl et al., "Integration of Group II Intron bl1 into a Foreign RNA by Reversal of the Self–Slicing Reaction In Vitro" *Cell*, vol. 60, pp. 629–636, Feb. 23, 1990.

Mohr et al., "Integration of a group I intron into a ribosomal RNA sequence promoted by a tyrosyl–tRNA synthetase" *Nature*, vol. 354, pp. 164–167, Nov. 14, 1991.

Mueller et al., "Group II Intron RNA Catalysis of Progressive Nucleotide Insertion: A Model for RNA Editing" *Science*, vol. 261, pp. 1035–1037, Aug. 20, 1993.

Ny et al., "The structure of the human tissue–type plasmonogen activator gene: Correlation of intron and exon structures to functional and structural domains" *Proceedings of the National Academy of Sciences*, vol. 81, pp. 5355–5359, Sep. 1984.

Patthy et al., "Intron–dependent evolution: preferred types of exons and introns" *FEBS Letters*, vol. 214, No. 1, pp. 1–7, Apr. 1987.

Peebles et al., "Group II Intron Selt–splicing: Development of Alternative Reaction Conditions and Identification of a Predicted Intermediate" *Cold Spring Harbor Symposia on Quantitative Biology*, vol. LII, pp. 223–232, 1987.

Peebles et al., "Mutation of the Conserved First Nucleotide of a Group II Intron from Yeast Mitochondrial DNA Reduces the Rate But Allows Accurate Splicing" *The Journal of Biological Chemistry*, vol. 268, No. 16, pp. 11929–11938, Jun. 5, 1993.

Puttaraju et al., "Group I permuted intron–exon (PIE) sequences self–splice to produce circular exons" *Nucleic Acids Research*, vol. 20, No. 20, pp. 5357–5364, 1992.

Saldanha et al., "Group I and group II introns" *The FASEB Journal*, vol. 7, pp. 15–24, Jan. 1993.

Schmeizer et al., "Self–Splicing of Group II Introns In Vitro: Mapping of the Branch Point and Mutation Inhibition of Lariat Formation" *Cell*, vol. 46, pp. 557–565, Aug. 15, 1986.

Schroeder et al., "Splice–Site Selection and Decoding: Are They Related?" *Science*, vol. 260, pp. 1443–1444, Jun. 4, 1993.

Seidel et al., "Exons as Microgenes?" *Science*, vol. 257, pp. 1489–1490, Sep. 11, 1992.

Sharp et al., "On the Origin of RNA Splicing and Introns" *Cell*, vol. 42, pp. 397–400, Sep. 1985.

Sharp et al., "Trans Splicing: Variation on a Familiar Theme?" *Cell*, vol. 50, pp. 147–148, Jul. 17, 1987.

Solnick et al., "Trans Splicing of mRNA Precursors" *Cell*, vol. 42, pp. 157–164, Aug. 1985.

Steitz et al., "Splicing Takes a Holliday" *Science*, vol. 257, pp. 888–889, Aug. 14, 1992.

Suchy et al., "Restoration of the Self–splicing Activity of a Defective Group II Intron by a Small Trans–acting RNA" *Institut für Genetik Mikrobiologie der Universität München*, pp. 179–187, Academic Press Limited 1991.

Von Ahesen et al., "Footprinting the Sites of Interaction of Antibiotics with Catlytic Group I Intron RNA" *Science*, vol. 260, pp. 1500–1503, Jun. 4, 1993.

Wallasch et al., "Structural requirements for selection of 5'–and 3' splice sites of group II introns" *Nucleic Acids Research*, vol. 19, No. 12, pp. 3307–3314, 1991.

Wang et al., "Movement of the Guide Sequence During RNA Catalysis by a Group I Ribozyme" *Science*, vol. 260, pp. 504–508, Apr. 23, 1993.

Woodson et al., "Reverse Self–Splicing of the Tetrahymena Group I Intron: Implication for the Directionality of Splicing and for Intron Transposition" *Cell*, vol. 57, pp. 335–345, Apr. 21, 1989.

Dube et al. (1989) Biochemistry, vol. 28, No. 14, pp. 5703–5707.

Beaudry et al. (1992) Science, vol. 257, pp. 635–641.

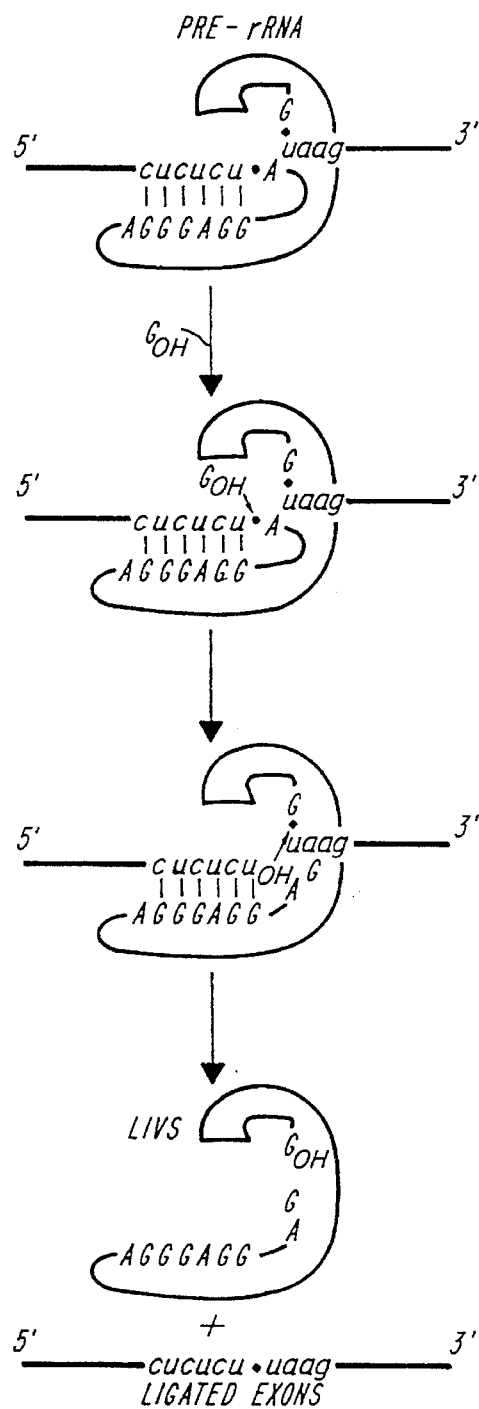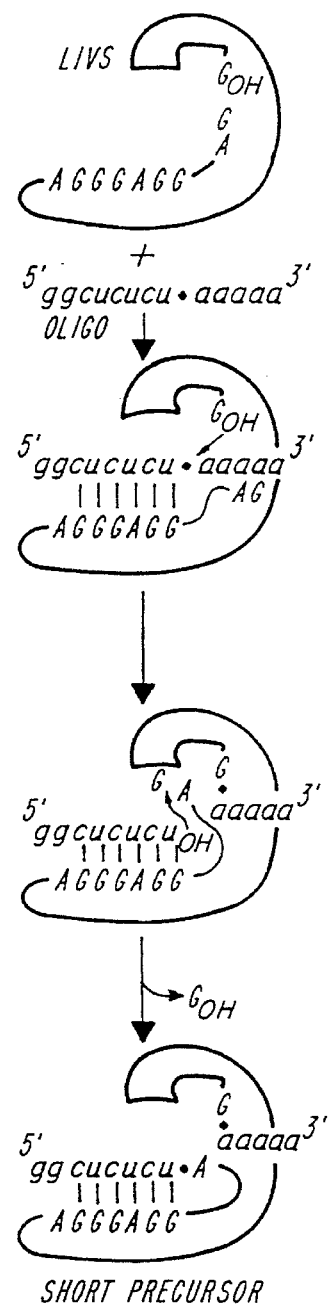
FIG. 3

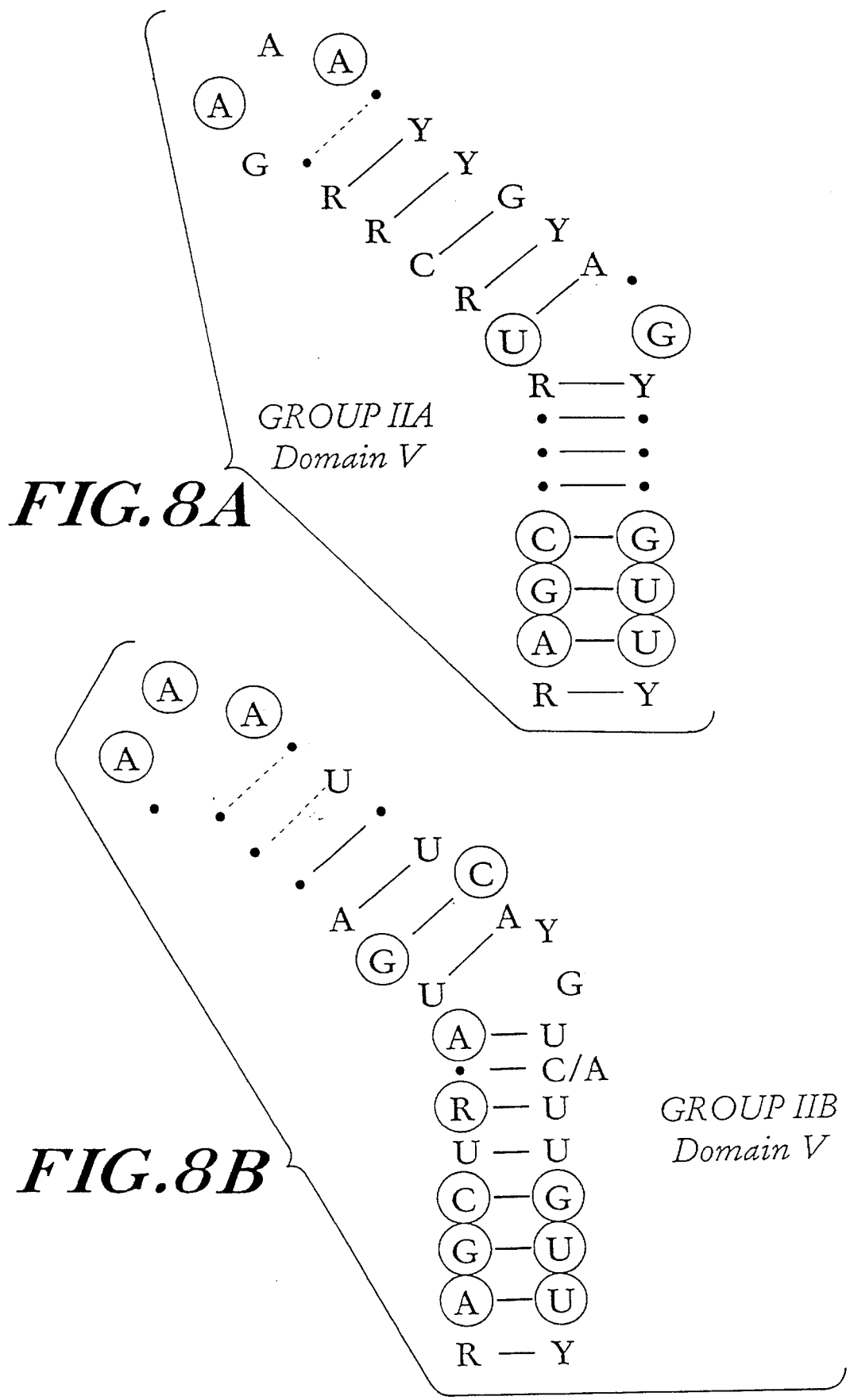
FIG. 8A GROUP IIA Domain V
FIG. 8B GROUP IIB Domain V

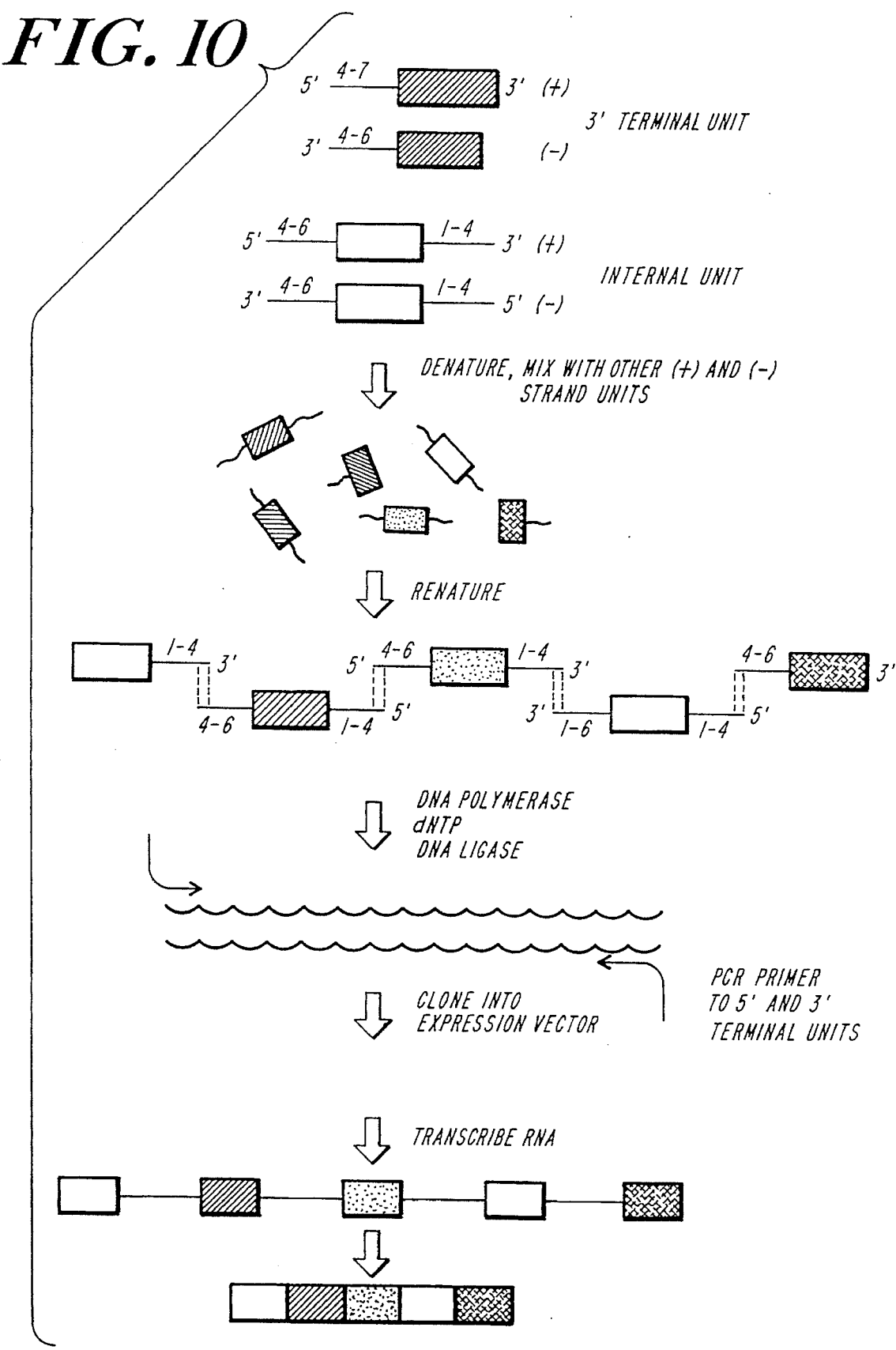

INTRON-MEDIATED RECOMBINANT TECHNIQUES AND REAGENTS

BACKGROUND OF THE INVENTION

Most eukaryotic genes are discontinuous with proteins encoded by them, consisting of coding sequences (exons) interrupted by non-coding sequences (introns). After transcription into RNA, the introns are removed by splicing to generate the mature messenger RNA (mRNA). The splice points between exons are typically determined by consensus sequences that act as signals for the splicing process.

Structural features of introns and the underlying splicing mechanisms form the basis for classification of different kinds of introns. Since RNA splicing was first described, four major categories of introns have been recognized. Splicing of group I, group II, nuclear pre-mRNA, and tRNA introns can be differentiated mechanistically, with certain group I and group II introns able to be autocatalytically excised from a pre-RNA in vitro in the absence of any other protein or RNA factors. In the instance of the group I, group II and nuclear pre-mRNA introns, splicing proceeds by a two-step transesterification mechanism.

To illustrate, the nuclear rRNA genes of certain lower eukaryotes (e.g., *Tetrahymena thermophila* and *Physarum polycephalum*) contain group I introns. This type of intron also occurs in chloroplast, yeast, and fungal mitochondrial rRNA genes; in certain yeast and fungal mitochondrial mRNA; and in several chloroplast tRNA genes in higher plants. Group I introns are characterized by a linear array of conserved sequences and structural features, and are excised by two successive transesterifications. Splicing of the Tetrahymena pre-rRNA intron, a prototypic group I intron, proceeds by two transesterification reactions during which phosphate esters are exchanged without intermediary hydrolysis. Except for the initiation step, promoted by a free guanosine, all reactive groups involved in the transesterification reactions are contained within the intron sequence. The reaction is initiated by the binding of guanosine to an intron sequence. The unshared pair of electrons of the 3'-hydroxyl group of the bound guanosine can act as a nucleophile, attacking the phosphate group at the 5' exon-intron junction (splice site), resulting in cleavage of the precursor RNA. A free 3'-hydroxyl group is generated at the cleavage site (the end of the 5' exon) and release of the intron occurs in a second step by attack of the 5' exon's 3'-hydroxyl group on the 3' splice site phosphate.

Group II introns, which are classed together on the basis of a conserved secondary structure, have been identified in certain organellar genes of lower eukaryotes and plants. The group II introns also undergo self-splicing reactions in vitro, but in this instance, a residue within the intron, rather than added guanosine, initiates the reaction. Another key difference between group II and group I introns is in the structure of the excised introns. Rather than the linear products formed during splicing of group I introns, spliced group II introns typically occur as lariats, structures in which the 5'-phosphoryl end of the intron RNA is linked through a phosphodiester bond to the 2'-hydroxyl group of an internal nucleotide. As with group I introns, the splicing of group II introns occurs via two transesterification steps, one involving cleavage of the 5' splice site and the second resulting in cleavage of the 3' splice site and ligation of the two exons. For example, 5' splice site cleavage results from nucleophilic attack by the 2'-hydroxyl of an internal nucleotide (typically an adenosine) located upstream of the 3' splice site, causing the release of the 5' exon and the formation of a lariat intermediate (so called because of the branch structure of the 2', 5' phosphodiester bond thus produced). In the second step, the 3'-end hydroxyl of the upstream exon makes a nucleophilic attack on the 3' splice site. This displaces the intron and joins the two exons together.

Eukaryotic nuclear pre-mRNA introns and group II introns splice by the same mechanism; the intron is excised as a lariat structure, and the two flanking exons are joined. Moreover, the chemistry of the two processes is similar. In both, a 2' hydroxyl group within the intron serves as the nucleophile to promote cleavage at the 5' splice site, and the 3' hydroxyl group of the upstream exon is the nucleophile that cleaves the 3' splice site by forming the exon-exon bond. However, in contrast to the conserved structural elements that reside within group I and II introns, the only conserved features of nuclear pre-mRNA introns are restricted to short regions at or near the splice junctions. In yeast, these motifs are (i) a conserved hexanucleotide at the 5' splice, (ii) an invariant heptanucleotide, the UACUAAC Box, surrounding the branch point A, (iii) a generally conserved enrichment for pyrimidine residues adjacent to the invariant AG dinucleotide at the 3' splice site. Further characteristics of nuclear pre-mRNA splicing in vitro that distinguish it from autocatalytic splicing are the dependence on added cell-free extracts, and the requirement for adenosine triphosphate (ATP). Another key difference is that nuclear pre-mRNA splicing generally requires multiple small nuclear ribonucleoproteins (snRNPs) and other accessory proteins, which can make-up a larger multi-subunit complex (splicesome) that facilitates splicing.

SUMMARY OF THE INVENTION

The present invention makes available methods and reagents for novel manipulation of nucleic acids. As described herein, the present invention makes use of the ability of intronic sequences, such as derived from group I, group II, or nuclear pre-mRNA introns, to mediate specific cleavage and ligation of discontinuous nucleic acid molecules. For example, novel genes and gene products can be generated by admixing nucleic acid constructs comprising "exon" nucleic acid sequences flanked by intron sequences that can direct trans-splicing of the exon sequences to each other. The flanking intronic sequences, by intermolecular complementation between the flanking intron sequences of two different constructs, form a functional intron which mediates the transesterification reactions necessary to cause the ligation of the discontinuous nucleic acid sequences to one another, and thereby generate a recombinant gene comprising the ligated exons. As used herein, the term exon denotes nucleic acid sequences, or exon "modules", that can, for instance, encode portions of proteins or polypeptide chains, such as corresponding to naturally occurring exon sequences or naturally occurring exon sequences which have been mutated (e.g. point mutations, truncations, fusions), as well as nucleic acid sequences from "synthetic exons" including sequences of purely random construction. However, the term "exon", as used in the present invention, is not limited to protein-encoding sequences, and may comprises nucleic acid sequences of other function, including nucleic acids of "intronic origin" which give rise to, for example, ribozymes or other nucleic acid structure having some defined chemical function.

As described herein, novel genes and gene products can be generated, in one embodiment of the present method, by admixing nucleic acid constructs which comprise a variegated population of exon sequences. As used herein, variegated refers to the fact that the population includes nucleic acids of different nucleotide compositions. When the interactions of the flanking introns are random, the order and composition of the internal exons of the combinatorial gene library generated is also random. For instance, where the variegated population of exons used to generate the combinatorial genes comprises N different internal exons, random trans-splicing of the internal exons can result in $N^y$ different genes having y internal exons. However, the present trans-splicing method can also be utilized for ordered gene assembly such that nucleic acid sequences are spliced together in a predetermined order, and can be carried out in much the same fashion as automated oligoucleotide or polypeptide synthesis. In similar fashion, an ordered combinatorial ligation can be carried out in which particular types of exons are added to one and other in an ordered fashion, but, at certain exon positions, more than one type of exon may be added to generate a library of combinatorial genes.

Furthermore, the present invention makes available methods and reagents for producing circular RNA molecules. In particular, exon constructs flanked by either group II or nuclear pre-mRNA fragments can, under conditions which facilitate exon ligation by splicing of the flanking intron sequences, drive the manufacture of circularly permuted exonic sequences in which the 5' and 3' ends of the same exon are covalently linked via a phosphodiester bond. Circular RNA moieties generated in the present invention can have several advantages over the equivalent "linear" constructs. For example, the lack of a free 5' or 3' end may render the molecule less susceptible to degradation by cellular nucleases. Such a characteristic can be especially beneficial, for instance, in the use of ribozymes in vivo, as might be involved in a particular gene therapy. The circularization of mature messenger-RNA transcripts can also be beneficial, by conferring increased stability as described above, as well as potentially increasing the level of protein translation from the transcript.

DESCRIPTION OF DRAWINGS

FIG. 3 is a schematic representation of an illustrative group I splicing reaction, as well as a reverse-splicing reaction.

FIGS. 8A and 8B illustrate the consensus sequence for group IIA and IIB domain V.

FIG. 10 is a schematic representation of an intron-mediated combinatorial method which relies on cis-splicing to ultimately form the chimeric genes.

DETAILED DESCRIPTION OF THE INVENTION

Figure 1A:
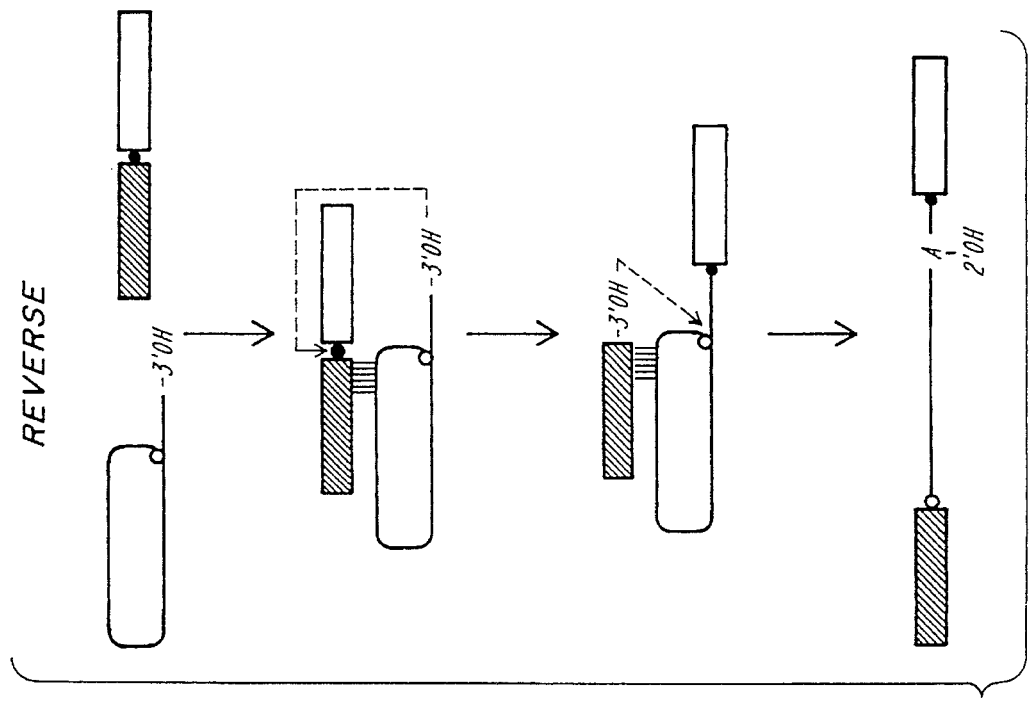
FIGS. 1A and 1B are a schematic representation of the group II splicing reaction, as well as the reverse-slicing reaction.

Biological selections and screens are powerful tools with which to probe protein and nucleic acid function and to isolate variant molecules having desirable properties. The technology described herein enables the rapid and efficient generation and selection of novel genes and gene products. The present combinatorial approach, for example, provides a means for capturing the vast diversity of exons, and relies on the ability of intron sequences to mediate random splicing between exons.

As described below, novel genes and gene products can be generated, in one embodiment of the present combinatorial method, by admixing a variegated population of exons which have flanking intron sequences that can direct trans-splicing of the exons to each other. Under conditions in which trans-splicing occurs between the exons, a plurality of genes encoding a combinatorial library are generated by virtue of the ability of the exons to be ligated together in a random fashion. Where the initial variegated exon population are ribonucleotides (i.e. RNA), the resulting combinatorial transcript can be reverse-transcribed to cDNA and cloned into an appropriate expression vector for further manipulation or screening.

In another embodiment of the present combinatorial method, a variegated population of single-stranded DNA molecules corresponding to exon sequences of both (+) and (−) strand polarity, and which have flanking intron sequences capable of mediating cis-splicing, are provided together such that a portion of the nucleic acid sequence in the flanking intron of an exon of one polarity (e.g. a (+) strand) can base pair with a complementary sequence in the flanking intron of another exon of opposite polarity (e.g. a (−) strand). Using standard techniques, any single-stranded regions of the concatenated exon/intron sequences can be subsequently filled-in with a polymerase, and nicks covalently closed with a ligase, to form a double-stranded chimeric gene comprising multiple exons interrupted by intron sequences. Upon transcription of the chimeric gene to RNA, cis-splicing can occur between the exons of the chimeric gene to produce the mature RNA transcript, which can encode a chimeric protein.

As used herein, the term exon denotes nucleic acid sequences, or exon "modules", that can, for instance, encode portions of proteins or polypeptide chains. The exons can correspond to discrete domains or motifs, as for example, functional domains, folding regions, or structural elements of a protein; or to short polypeptide sequences, such as reverse turns, loops, glycosylation signals and other signal sequences, or unstructured polypeptide linker regions. The exons modules of the present combinatorial method can comprise nucleic acid sequences corresponding to naturally occurring exon sequences or naturally occurring exon sequences which have been mutated (e.g. point mutations, truncations, fusions), as well as nucleic acid sequences from "synthetic exons" including sequences of purely random construction, that is, nucleic acid sequences not substantially similar to naturally occurring exon sequences. In some instances, the exon module can correspond to a functional domain, and the module may comprise a number of naturally occurring exon sequences spliced together, with the intron sequences flanking only the exon sequences disposed at the extremity of the module.

Moreover, the term "exon", as used in the present invention, is not limited to protein-encoding sequences, and may comprises nucleic acid sequences of other function, including nucleic acids of "intronic origin" which give rise to, for example, ribozymes or other nucleic acid structure having some defined chemical function. As illustrated below, group II intron domains (e.g. domains I–VI) and group I intron domains (e.g. paired regions P1-P10) can themselves be utilized as "exons", each having flanking intronic sequences that can mediate combinatorial splicing between different group I or group II domains to produce novel catalytic intron structures. In another illustrative embodiment, the exon can comprise a cloning or expression vector into which other nucleic acids are ligated by an intron-mediated trans-splicing reaction.

With respect to generating the protein-encoding exon constructs of the present invention, coding sequences can be isolated from either cDNA or genomic sources. In the instance of cDNA-derived sequences, the addition of flanking intronic fragments to particular portions of the transcript can be carried out to devise combinatorial units having exonic sequences that correspond closely to the actual exon boundaries in the pre-mRNA. Alternatively, the choice of coding sequences from the cDNA clone can be carried out to create combinatorial units having "exon" portions chosen by some other criteria. For example, as described below with regard to the construction of combinatorial units from either antibody or plasminogen activator cDNA sequences, the criteria for selecting the exon portions of each splicing construct can be based on domain structure or function of a particular portion of the protein.

Several strategies exist for identifying coding sequences in mammalian genomic DNA which can subsequently be used to generate the present combinatorial units. For example, one strategy frequently used involves the screening of short genomic DNA segments for sequences that are evolutionarily conserved, such as the 5' splice site and branch acceptor site consensus sequences (Monaco et al. (1986) Nature 323:646–650; Rommens et al. (1989) Science 245:1059–1065; and Call et al. (1990) Cell 60: 509–520). Alternative strategies involve sequencing and analyzing large segments of genomic DNA for the presence of open reading frames (Fearson et al. (1990) Science 247:49–50), and cloning hypo-methylated CpG islands indicative of 5' transcriptional promoter sequences (Bird et al. (1986) Nature 321:209– 213). Yet another technique comprises the cloning of isolated genomic fragments into an intron which is in turn disposed between two known exons. The genomic fragments are identified by virtue of the ability of the inserted genomic sequences to direct alternate splicing which results in the insertion into a mature transcript of at least one genomic-derived exon between the two know exons (Buckler et al. (1991) PNAS 88:4005–4009).

Exons identified from genomic DNA can be utilized directly as combinatorial units by isolating the identified exon and appropriate fragments of the flanking intron sequences normally associated with it. Alternatively, as with the cDNA derived exons, the genomic-derived exon can be manipulated by standard cloning techniques (Molecular Biology. A Laboratory Manual, eds. Sambrook, Fritsch and Maniatis (New York: CSH Press, 1989); and Current Protocols in Molecular Biology, Eds. Ausebel et al. (New York: John Wiley & Sons, 1989)) into vectors in which appropriate flanking intronic sequences are added to the exon upon transcription. In yet another embodiment, the reversal of splicing reactions, described below for the various intron groups, can be used to specifically add flanking intron fragments to one or both ends of the exonic sequences, and thereby generate the combinatorial units of the present invention.

Furthermore, generating the splicing units useful in the present combinatorial methods, one skilled in the art will recognize that in the instance of protein-encoding exons, particular attention should be payed to the phase of the intronic fragments. Introns that interrupt the reading frame between codons are known as "Phase 0" introns; those which interrupt the codons between the first and second nucleotides are known as "Phase 1" introns; and those interrupting the codons between the second and third nucleotides are known as "Phase 2" introns. In order to prevent a shift in reading frame upon ligation of two exons, the phase at both the 5' splice site and 3' splice site must be the same. The phase of the flanking intronic fragments can be easily controlled during manipulation, especially when reverse splicing is utilized to add the intronic fragments, as the each insertion site is known. However, as described below, when the variegated population of combinatorial units comprises flanking intronic fragments of mixed phase, particular nucleotides in the intronic sequences can be changed in such a manner as to lower the accuracy of splice site choice. In addition, the splicing reaction conditions can also be manipulated to lower the accuracy of splice site choice.

I. Intronic Sequences

The present invention makes use of the ability of introns to mediate ligation of exons to one and other in order to generate a combinatorial library of genes from a set of discontinuous exonic sequences. This method is not limited to any particular intron or class of introns. By way of example, the intronic sequences utilized can be selected from group I, group II, or nuclear pre-mRNA introns. Furthermore, in light of advancements made in delineating the critical and dispensable elements in each of the classes of introns, the present invention can be practiced with portions of introns which represent as little as the minimal set of intronic sequences necessary to drive exon ligation.

Group I introns, as exemplified by the Tetrahymena ribosomal RNA (rRNA) intron, splice via two successive phosphate transfer, transesterification reactions. As illustrated in FIG. 3, the first transesterification is initiated by nucleophilic attack at the 5' junction by the 3' OH of a free guanosine nucleotide, which adds to the 5' end of the intron and liberates the 5' exon with a 3' OH. The second transesterification reaction is initiated by nucleophilic attack at the 3' splice junction by the 3' OH of the 5' exon, which results in exon ligation and liberates the intron.

Figure 1B:
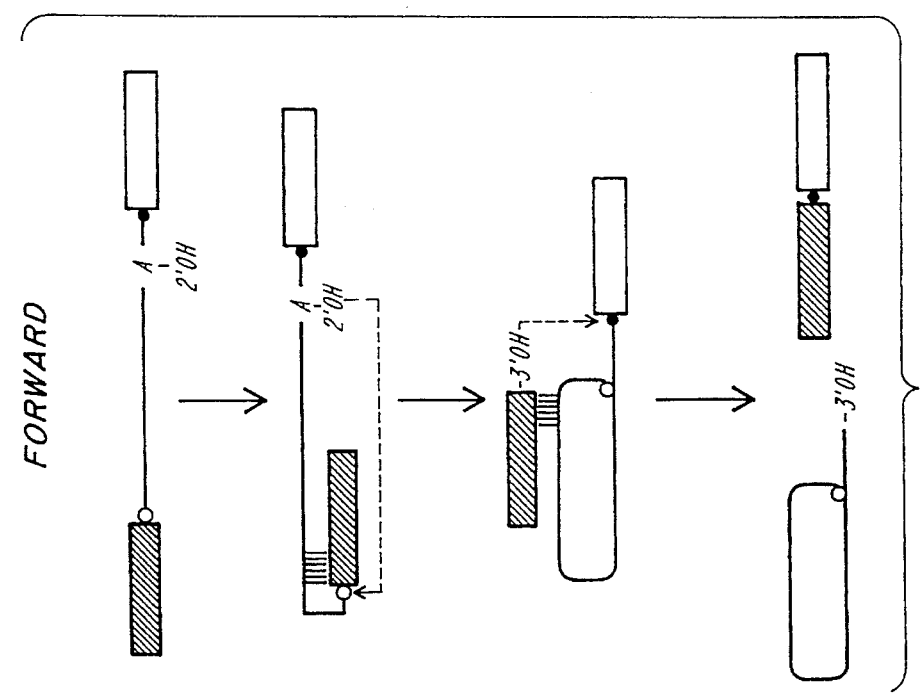

Group II introns also splice by way of two successive phosphate transfer, transesterification reactions (see FIG. 1). There is, however, one prominent difference between the reaction mechanisms proposed for group I and group II introns. While cleavage at the 5' junction in group I splicing is due to nucleophilic attack by a free guanosine nucleotide, cleavage at the 5' junction in group II splicing is typically due to nucleophilic attack by a 2' OH from within the intron. This creates a lariat intermediate with the 5' end of the intron attached through a 2', 5'-phosphodiester bond to a residue near the 3' end of the intron. Subsequent cleavage at the 3' junction results in exon ligation and liberates the "free" intron in the form of a lariat. The nature of the initiating nucleophile notwithstanding, the two self-splicing mechanism appear quite similar as both undergo 5' junction cleavage first, and subsequently 3' junction cleavage and exon ligation as a consequence of nucleophilic attack by the 5' exon. Furthermore, nuclear pre-mRNA, in similar fashion to group II—intron splicing, also proceed through a lariat intermediate in a two-step reaction.

All three intron groups share the feature that functionally active introns able to mediate splicing can be reconstituted from intron fragments by non-covalent interactions between the fragments (and in some instances other trans-acting factors). Such "trans-splicing" by fragmented introns, as described herein, can be utilized to ligate discontinuous exon sequences to one and other and create novel combinatorial genes. Moreover, autocatalytic RNA (i.e. group I and group II introns) are not only useful in the self-splicing reactions used generate combinatorial libraries, but can also catalyze reactions on exogenous RNA.

The following description of each of the group I, group II, and nuclear pre-mRNA intronic sequences is intended to illustrate the variation that exists in each group of introns. Moreover, the descriptions provide further insight to one skilled in the art to devise exon constructs useful in the present splicing methods, using as little as a minimal set of intronic fragments.

A. Group II Introns

Group II introns, which are classed together on the basis of a conserved secondary structure, are found in organellar genes of lower eukaryotes and plants. Like introns in nuclear pre-mRNA, group II introns are excised by a two-step splicing reaction to generate branched circular RNAs, the so-called intron-lariats. A remarkable feature of group II introns is their self-splicing activity in vitro. In the absence of protein or nucleotide cofactors, the intronic RNA catalyzes two successive transesterification reactions which lead to autocatalytic excision of the intron-lariat from the pre-mRNA and concomitantly to exon ligation. (See FIG. 1).

Figure 2:
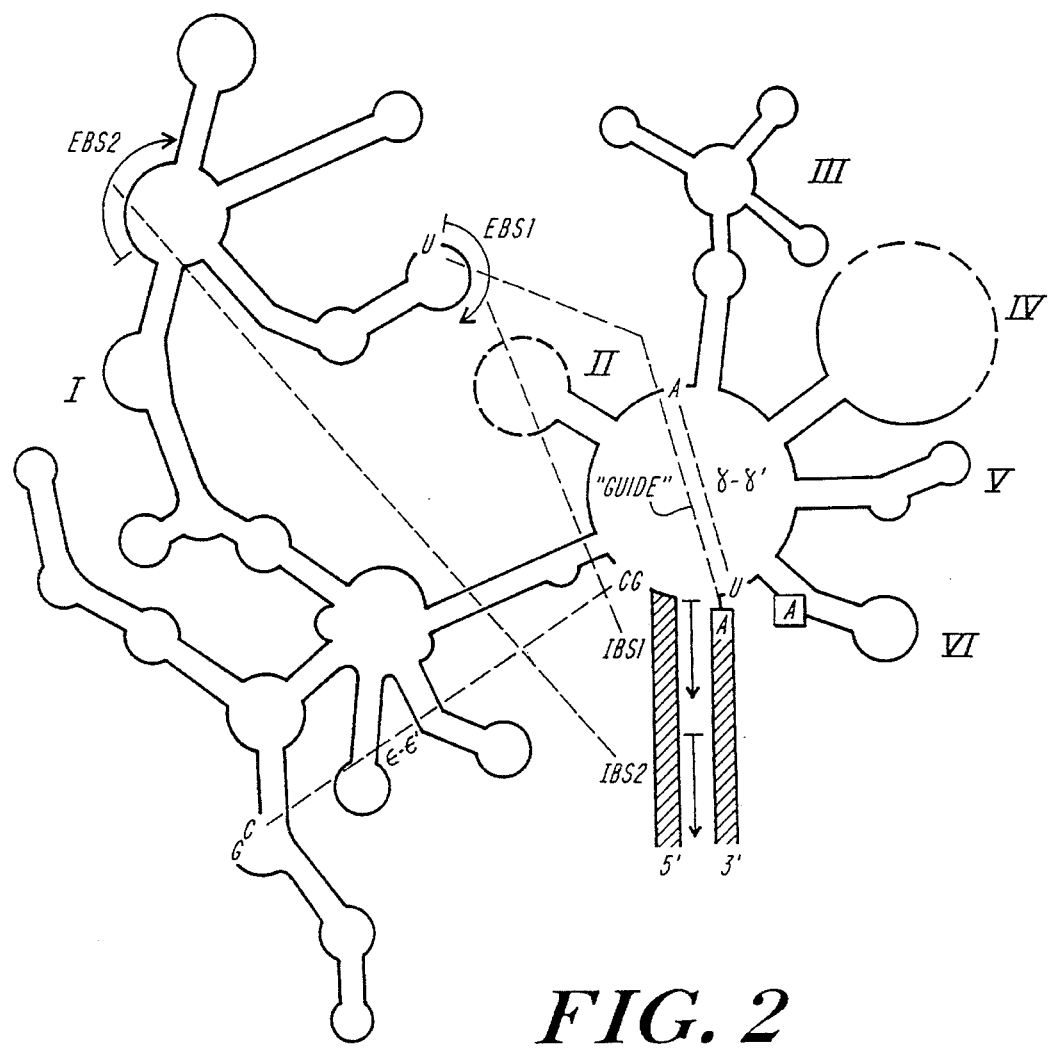
FIG. 2 illustrates the domain structure of a group II intron.

More than 100 group II intron sequences from fungal and plant mitochondria and plant chloroplasts have been analyzed for conservation of primary sequence, secondary structure and three-dimensional base pairings. Group II introns show considerable sequence homology at their 3' ends (an AY sequence), and have a common $G_1W_2G_3Y_4G_5$ motif at their 5' ends, but do not show any other apparent conserved sequences in their interior parts. However, group II introns are generally capable of folding into a distinctive and complex secondary structure typically portrayed as six helical segments or domains (designated herein as domains I–VI) extending from a central hub (see FIG. 2). This core structure is believed to create a reactive center that promotes the transesterification reactions.

However, mutational analysis and phylogenetic comparison indicate that certain elements of the group II intron are dispensable to self-splicing. For example, several group II introns from plants have undergone some rather extensive pruning of peripheral and variable stem structures. Moreover, while the group II intron can be used to join two exons via cis-splicing, a discontinuous group II intron form of trans-splicing can be used which involves the joining of independently transcribed coding sequences through interactions between intronic RNA pieces. In vitro studies have shown that breaks, for example within the loop region of domain IV, can be introduced without disrupting self-splicing. The ability of group II intron domains to reassociate specifically in vivo is evidenced by trans-spliced group II introns, which have been found, for example, in the rps-12 gene of higher plant ctDNA, the psaA gene in Chlamydomonas reinhardtii ctDNA, and the nad1 and nad5 genes in higher plant mtDNA (Michel et al. (1989) Gene 82:5–30; and Sharp et al. (1991) Science 254:663). These genes consist of widely separated exons flanked by 5'- or 3'-segments of group II introns split in either domains III or IV. The exons at different loci are transcribed into separate precursor RNAs, which are trans-spliced, presumably after the association of the two segments of the group II intron. Moreover, genetic analysis of trans-splicing of the Chlamydomonas reinhardtii psaA gene has demonstrated that the first intron of this gene is split into three segments. The 5' exon is flanked by parts of domain I and the 3' exon by parts of domains IV to VI, respectively. The middle segment of the intron is encoded at a remote locus, tscA, and consists of the remainder of domains I to IV. This tscA segment can apparently associate with the other two intron segments to reconstitute an intron capable of splicing the two exons (Goldschmidt et al. (1991) Cell 65:135–143).

The functional significance to self-splicing of certain control structural elements have been further deduced by analysis of minimal trans-splicing sets, and found to generally comprise an exon-binding site and intron-binding site, a structural domain V, and (though to lesser extent) a "branch-site" nucleotide involved in lariat formation. Domain I contains the exon-binding sequences. Domain VI is a helix containing the branch site, usually a bulged A residue. Domain V, the most highly conserved substructure, is required for catalytic activity and binds to at least a portion of domain I to form the catalytic core.

The 5' splice sites of group II introns are defined by at least three separate tertiary base pairing contacts between nucleotides flanking the 5' splice site and nucleotides in substructures of domain I. The first interaction involves a loop sequence in the D sub-domain of domain I (exon binding site 1 or EBS 1) that base pairs with the extreme 3' end of the 5' exon (intron binding site 1 or IBS 1). The second interaction involves the conserved dinucleotide -$G_3Y_4$- (designated ε) that base pairs with a dinucleotide in the C1 subdomain of domain I (designated ε'). The third interaction involves base pairing between intron binding site 2 (IBS 2), a sequence located on the 5' side of IBS 1, with exon binding site 2 (EBS 2), a loop sequence of the D subdomain of domain I near EBS 1. Of the two exon-binding sites identified in group II introns, only EBS 1 is common to all group II members. The EBS 1 element comprises a stretch of 3 to 8 consecutive residues, preferably 6, located within domain I, which are complementary to the last 3 to 8 nucleotides of the 3' exon end of the 5' exon. The EBS 2-IBS 2 pairing also typically consists of two 4–8 nucleotide stretches. Its exonic component (IBS 2) lies from 0 to 3 nucleotides upstream from the IBS 1 element, and the intronic component (EBS 2) also lies within domain I. However, while IBS 2-EBS 2 pairing can improve the efficiency of 5' splice site use, particularly in trans-, it is subject to many more variations from the IBS 1-EBS 1 interaction, such as reduced length, presence of bulging nucleotides or a mismatch pair. Disrupting the IBS 2-EBS 2 pairing, in the Sc.a5 group II intron for example, is essentially without effect on the normal splicing reaction, and in at least twelve group II introns analyzed, the IBS 2-EBS 2 interaction seems to be missing altogether and is apparently less important than the IBS 1-EBS 2 interaction. As already noted, only that pairing is absolutely constant in (typical) group II introns, and always potentially formed at cryptic 5' splice sites.

Further studies, while confirming that the EBS 1-IBS 1 base pairing is necessary for activation of the 5' junction, indicate that this interaction alone is not always sufficient for unequivocal definition of the cleavage site. It has been established that altering the first nucleotide of the group II intron (e.g., $G_1$ of $G_1W_2G_3Y_4G_5$) can reduce the self-splicing rate in vitro. Characterization of the products of self-splicing from $G_1\rightarrow N$ mutant transcripts have demonstrated that the relative order of function is G>U>A>C. It is also suggested that the 5' G of the intron helps to position the cleavage site precisely (Wallasch et al. (1991) Nuc. Acid Res. 19:3307–3314). For example, the presence of an additional adenosine following IBS 1 can lead to ambiguous hydrolytic cleavages at the 5' intron/exon boundary. As described herein, such ambiguity can be used to address exon phasing.

Another well conserved feature of group II introns is the bulging A located 7 to 8 nt upstream from the 3' intron-exon junction on the 3' side of helix VI. This is the nucleotide which participates in the long range, 2'-5' lariat bond (Van der Veen et al. (1986) Cell 44:225– 234; Schmelzer and Schweyen (1986) Cell 46:557–565; Jacquier and Michel (1987) Cell 50:17–29; Schmelzer and Muller (1987) Cell 51:753–762). Evidence from electron microscopy, attempts at reverse transcription of circular introns, and treatment with the 2',5' -phosphodiesterase of HeLa cells indicate that group II introns are excised as lariats (Van der Veen et al. (1986) Cell 44:225–234; Schmidt et al. (1987) Curr. Genet. 12:291–295; Koller et al. (1985) Embo J. 4:2445–2450). However, lariat formation is not absolutely essential for correct exon ligation to occur. Cleavage at the 5' splice site, presumably mediated by free hydroxide ions rather than a 2'-OH group, followed by normal exon ligation, has been observed both in trans-splicing reactions (Jacquier and Rosbash (1986) Science 234:1099– 1104; and Koch et al. (1992) Mol. Cell Biol. 12:1950–1958) and, at high ionic strength, in cis-splicing reactions with molecules mutated in domain VI (Van der Veen et al. (1987) Embro J. 12:3827–3821). Also, several group II introns lack a bulging A on the 3' side of helix VI. For instance, all four CP tRNA-VAL introns of known sequence have a fully paired helix VI, and their 7th nucleotide upstream from the 3' intron-exon junction is a G, not an A. Furthermore, correct lariat formation has been observed with a mutant of intron Sc.b1 whose helix VI should be fully paired, due to the insertion of an additional nucleotide (a U) at the site facing the normally bulging A (Schmelzer and Muller (1987) Cell 51:753–762).

Perhaps one of the best conserved structural elements of group II introns is domain V. The typical domain V structure contains 32–34 nucleotides and is predicted to fold as a hairpin. The hairpin is typically an extended 14 base pair helix, capped by a four base loop involving 15–18, and punctuated by a 2 base bulge at positions 25 and 26. Comparative sequence analysis (Michel et al. (1989) Gene 82:5–30) has shown that group II introns can generally be classified into one of two classes (e.g. group IIA and IIB). FIG. 8 shows the consensus sequences of domain V for each of the IIA and IIB introns. Base pairs that are highly conserved are indicated by solid lines. Dashed lines indicate less well conserved base pair interactions. The unpaired loop at the apex of the hairpin is typically an NAAA sequence, where N is most often a G for IIA introns. Nucleotides which are highly conserved are circled, while less conserved nucleotides are uncircled. A black dot indicates a lack of discernible sequence consensus.

Degenerate group II introns can be functional despite lacking some domains. Euglena ctDNA, for example, contains a large number of relatively short group II introns which sometimes lack recognizable cognates of domain II, III, or IV. The view that the only group II structures required for splicing activities are domains I and V is supported by a detailed mutational analysis of a yeast mitochondrial group II intron in which various domains were deleted, either singly or in combinations. (Koch et al. (1992) Mol. Cell. Biol. 12:1950–1958). For example, the removal or disruption of the domain VI helix simply reduces 3' splice site fidelity and reaction efficiency. This analysis has led to the belief that domain V probably interacts with domain I to activate the 5' splice site, since a transcript lacking domains II–IV, and VI, but retaining domain I and domain V was capable of specific hydrolysis of the 5' splice junction.

With regard to 3' splice-site selection, two weak contacts are believed to play a role in defining the 3' splice-site but are, however, not essential to splicing. The first of these contacts is a lone base pair, termed γ/γ', between the 3' terminal nucleotide of the introns and a single base between domains II and III. (Jacquier et al. (1990) J. Mol. Biol. 13:437–447). A second single base pair interaction, termed the internal guide, has been defined between the first base of the 3' exon and the nucleotide adjacent to the 5' end of EBS 1 (Jacquier et al. (1990) J. Mol. Biol. 219:415–428).

In addition to the ability of autocatalytic RNAs such as group I and group II introns to excise themselves from RNA and ligate the remaining exon fragments, ample evidence has accumulated demonstrating that the autocatalytic RNAs can also catalyze their integration into exogenous RNAs. For example, both group I and group II introns can integrate into foreign RNAs by reversal of the self-splicing reactions. The mechanism of the group II intron reverse-splicing reaction is shown in FIG. 1. In the first step of the reverse reaction, the attack of the 3' OH group of the intron 3' terminus at the junction site of the ligated exons yields a splicing intermediate, the intron-3' exon lariat, and the free 5' exon. In the second step, the 5' exon which is still bound to the lariat via the IBS 1/EBS 1 base pairing can attack the 2'-5' phosphodiester bond of the branch. This transesterification step leads to reconstitution of the original precursor. The analogous reaction of the intron with a foreign RNA harboring an IBS 1 motif results in site-specific integration downstream of the IBS 1 sequence.

The exon constructs of the present invention, whether comprising the group II intronic sequences described above or the group I or nuclear pre-mRNA intronics described below, can be generated as RNA transcripts by synthesis in an in vitro transcription system using well known protocols. For example, RNA can be transcribed from a DNA template containing the exon construct using a T3 or T7 RNA polymerase, in a buffer solution comprising 40 mm Tris-HCl (pH 7.5), 6 mM $MgCl_2$, 10 mM dithiothreitol, 4 mM spermidine and 500 mM each ribonucleoside triphosphate. In some instances, it will be desirable to omit the spermidine from the transcription cocktail in order to inhibit splicing of the transcribed combinatorial units.

Several reaction conditions for facilitating group II-mediated splicing are known. For example, the reaction can be carried out in "Buffer C" which comprises 40 mM Tris-HCl (pH 7.0), 60 mM $MgCl_2$, 2 mM spermidine, and 500 mM KCl (Wallasch et al. (1991) Nuc. Acid Res. 19:3307–3314; and Suchy et al. (1991) J. Mol. Biol. 222:179–187); or "Buffer S" which comprises 70 mM $Tris-SO_4$ (pH 7.5) 60 mM $MgSO_4$, 2 mM spermidine, and 500 mM $(NH_4)_2 SO_4$ (Morl et al. (1990) Nuc. Acid Res. 18:6545–6551; and Morl et al. (1990) Cell 60:629–636). The group II ligation reactions can be carried out, for instance, at 45° C., and the reaction stopped by EtOH precipitation or by phenol:chloroform (1:1) extraction. Suitable reaction conditions are also disclosed in, for example. Jacquier et al. (1986) Science 234:1099–1104; Franzer et al. (1993) Nuc. Acid Res. 21:627–634; Schmelzer et al. (1986) Cell 46:557–565: Peebles et al. (1993) J. Biol. Chem. 268:11929–11938; Jarrell et al. (1988) J. Biol. Chem. 263:3432–3439; and Jarrell et al. (1982) Mol. Cell Biol. 8:2361–2366. Moreover, manipulation of the reaction conditions can be used to favor certain reaction pathways, such as a reverse-splicing reaction (e.g., by increasing the $MgSO_4$, concentration to 240 mM in Buffer S); bypassing the need for a branch nucleotide acceptor (e.g. high salt); and decreasing the accuracy of splice-site choice (Peebles et al. (1987) CSH Symp. Quant. Biol. 52:223–232).

B. Group I Introns

Group I introns are present in rRNA, tRNA, and protein-coding genes. They are particularly abundant in fungal and plant mitochondrial DNAs (mtDNAs), but have also been found in nuclear rRNA genes of Tetrahymena and other lower eukaryotes, in chloroplast DNAs (ctDNAs), in bacteriophage, and recently in several tRNA genes in eubacteria.

As first shown for the Tetrahymena large rRNA intron, group I introns splice by a mechanism involving two transesterification reactions initiated by nucleophilic attack of guanosine at the 5' splice site (See FIG. 3). The remarkable finding for the Tetrahymena intron was that splicing requires only guanosine and $Mg^{2+}$. Because bond formation and cleavage are coupled, splicing requires no external energy source and is completely reversible. After excision, some group I introns circularize via an additional transesterification, which may contribute to shifting the equilibrium in favor of spliced products.

The ability of group I introns to catalyze their own splicing is related to their highly conserved secondary and tertiary structures. The folding of the intron results in the formation of an active site juxtaposing key residues that are widely separated in primary sequence. This RNA structure catalyzes splicing by bring the 5' and 3' splice sites and guanosine into proximity and by activating the phosphodiester bonds at the splice sites. Different group I introns have relatively little sequence similarity, but all share a series of the short, conserved sequence elements P, Q, R, and S. These sequence elements always occur in the same order and basepair with one another in the folded structure of the intron (see FIG. 4). Element R [consensus sequence (C/G)YUCA(GA/AC)GACUANANG] and S [consensus AAGAUAGUCY] are the most highly conserved sequences within group I introns, and typically serve as convenient "landmarks" for the identification of group I introns. The boundaries of group I introns are marked simply by a U residue at the 3' end of the 5' exon and a G residue at the 3' end of the intron. (see, for example, Michel et al. (1990) J Mol Biol 216:585–610; Cech, TR (1990) Annu Rev Biochem 59:543–568; Cech, TR (1988) Gene 73:259–271; Burke (1989) Methods in Enzymology 190:533–545; and Burke et al. (1988) Gene 73:273–294)

The conserved group I intron secondary structure was deduced from phylogenetic comparisons, and specific features have been confirmed by analysis of in vivo and in vitro mutations and by structure mapping. The structure, shown in FIG. 4, consists of a series of paired regions, denoted P1-P10, separated by single-stranded regions (denoted J) or capped by loops (denoted L), from the core of the structure. The fundamental correctness of the model is supported by the observation that a vast number of group I intron sequences can be folded into this basic structure.

P1 and P10, which contain the 5' and 3' splice sites, respectively, are formed by base pairing between an internal guide sequence (IGS), generally located just downstream of the 5' splice site, and exon sequences flanking the splice sites. Group I introns have been classified into four major subgroups, designated IA to ID, based on distinctive structural and sequence features. Group IA introns, for example, contain two extra pairings, P7.1/P7.1a or P7.1/P7.2, between P3 and P7, whereas many group IB and IC introns may contain additional sequences, including open reading frames (ORFs), in positions that do not disrupt the conserved core structure. Indeed, many of the peripheral stem-loops can be completely deleted without major loss of splicing function. For example, the phage T4 sunY intron has been re-engineered to contain as few as 184 nucleotides while still retaining greater than 10 -percent activity. Presumably, if the criterion for activity were lowered, the minimal size one could achieve would be decreased.

The region of the Tetrahymena intron required for enzymatic activity, the catalytic core, consists of P3, P4, P6, P7, P8, and P9.0. Mutation of a nucleotide involved in one of these core structural elements typically decreases the maximum velocity of splicing, increase $K_m$ for guanosine, or both. In those instances where the primary importance of the nucleotide is its contribution to the formation of a duplex region, a second-site mutation that restores base-pairing also restores splicing function. Studies using Fe(II)-EDTA, a reagent that cleaves the sugar-phosphate backbone, have shown that parts of the core are buried in the structure inaccessible to the solvent, that $Mg^{2+}$ is necessary for folding of the intron, and that individual RNA domains fold in a specific order as $Mg^{2+}$ is increased. All group I introns have fundamentally similar core structures, but subgroup-specific structures such as P7.1, P7.2, and P5abc appear to participate in additional interactions that stabilize the core structure in different ways (Michel et al. (1990) J Mol Biol 216:585–610; and Michel et al. (1992) Genes & Dev 6:1373–1385).

A three dimensional model of the group I intron catalytic core has been developed by Michel and Westhof (Michel et al. (1990) J Mol Biol 216:585–610) through comparative sequence analysis. In the Michel-Westhof model, the relative orientation of the two helices is constrained by a previously proposed triple helix involving parts of J3/4-P4-P6-J6/7 and by potential tertiary interactions identified by co-variation of nucleotides that are not accounted for by secondary structure. A number of these binding sites accounts for the known splicing mechanism, which requires appropriate alignments of guanosine and the 5' and 3' exons in the first and second steps of splicing. Deoxynucleotide and phosphorothioate substitution experiments suggest that functionally important $Mg^{2+}$ ions are coordinated at specific positions around the active site (e.g., P1 and J8/7) where they may function directly in phosphodiester bond cleavage (Michel et al. (1990) J Mol Biol 216:585–610; and Yarus, M (1993) FASEB J 7:31–9). Basic features of the predicted three-dimensional structure have been supported by mutant analysis in vitro and by the use of specifically positioned photochemical cross-linking and affinity cleavage reagents.

Figure 4:
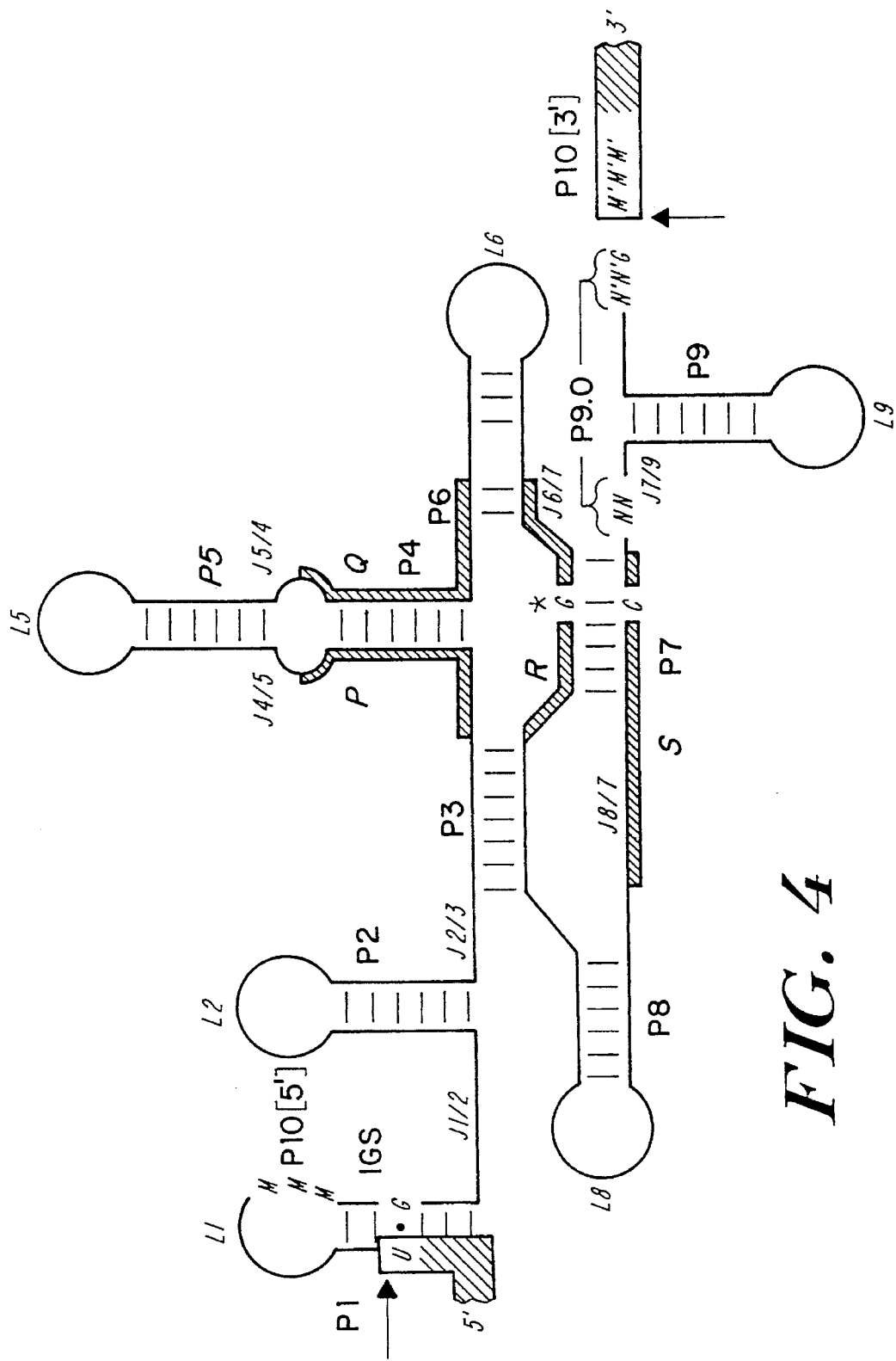
FIG. 4 illustrates the secondary structure of a group I intron.

The 5' and 3' splice sites of group I introns are substrates that are acted on by the catalytic core, and they can be recognized and cleaved by the core when added on separate RNA molecules (Cech, TR (1990) Annu Rev Biochem 59:543–568). In group I introns the last 3–7 nucleotides of the 5' exon are paired to a sequence within the intron to form the short duplex region designated P1. The intron-internal portion of P1 is also known as the 5' exon-binding site and as a portion of the internal guide sequence, IGS. The P1s of different group I introns vary widely in sequence. Neither the sequence nor length of P1 is fixed, but the conserved U at the 3' end of the 5' exon always forms a wobble base pair with a G residue in the IGS (FIG. 4). The conserved U:G is one important recognition element that defines the exact site of guanosine attack. In general, other base combinations do not substitute well. One exception is C:G, which maintains the accuracy of splicing but decreases the Kcat/Km by a factor of 100. Another exception is C:A; the ability of this pair to substitute well for U:G has been interpreted as an indication that disruption of P1 by a wooble base pair is a key element in recognition of the splice site. Position within the P1 helix is another determinant of 5' splice site. Analysis of in vitro mutants has shown that the distance of the U:G pair from the bottom of the P1 helix is critical for efficient cleavage in the Tetrahymena intron and that J1/2 and P2 also play a role in the positioning of P1 relative to the core (Michel et al. (1990) J Mol Biol 216:585–610; Young et al. (1991) Cell 67:1007–1019; and Salvo et al. (1992) J Biol Chem 267:2845–2848). The U:G pair is most efficiently used when located 4–7 base pairs from the base of the P1.

The positioning of the 3' splice site in group I introns depends on at least three interactions, whose relative importance differs in different introns. These are the P10 pairing between the IGS and the 3' exon, binding of the conserved G residue at the 3' end of the intron to the G-binding site in the second step of splicing, and an additional interaction, P9.0, which involves base paring between the two nucleotides preceding the terminal G of the intron and two nucleotides in J7/9 (Cech, TR (1990) Annu Rev Biochem 59:543–568).

Group I introns have $K_m$ values for guanosine that are as low as 1 μM and readily discriminate between guanosine and other nucleosides. The major component of the guanosine-binding site corresponds to a universally conserved CG pair in P7. Guanosine was initially proposed to interact with this base pair via formation of a base triple, but the contribution of neighboring nucleotides and the binding of analogs are also consistent with a model in which guanosine binds axially to the conserved G and flanking nucleotides. The guanosine-binding site of group I introns can also be occupied by the guanidino groups of arginine or antibiotics, such as streptomycin, which act as competitive inhibitors of splicing (von Ahsen et al. (1991) Nuc Acids Res 19:2261–2265).

Group I introns can also be utilized in both trans-splicing and reverse-splicing reactions. For example, the ribozyme core of a group I intron can be split in L6, and through intermolecular complementation, a functional catalytic core can be reassembled from intronic fragments (i.e. P1–6.5 and P6.5–10) on separately transcribed molecules (Galloway et al. (1990) J. Mol. Biol. 211:537–549).

Furthermore, as described for group II intron constructs, combinatorial units comprising group I introns can be transcribed from DNA templates by standard protocols. The group I self-splicing reaction has an obligatory divalent cation requirement, which is commonly met by $Mg^{2+}$. The reaction can in fact be stopped using a chelating agent such as EDTA. The group I-mediated splicing of exonic sequences can be carried out, for example, in a buffer comprising 100 mM $(NH_4)_2SO_4$, 50 mM HEPES (pH 7.5), 10 mM $MgCl_2$, and 25 μM GTP, at a temperature of 42° C. (Woodson et al. (1989) Cell 57:335–345). In another embodiment, the reaction buffer comprises 50 mM Tris-HCl (pH 7.5), 50 mM $NH_4Cl$, 3 mM $MgCl_2$, 1 mM spermidine, and 100 mM GTP, and the reaction proceeds at 55° C. (Salvo et al. (1990) J. Mol. Biol. 211:537–549). To form the reverse-splicing reaction, the $Mg^{2+}$ concentration can be increased (e.g., to 25 mM) and the GTP omitted. Typically, the reversal of splicing reaction is favored by high RNA concentrations, high magnesium and temperature, and the absence of guanosine. Other examples of useful reaction conditions for group I intron splicing can be found, for example, in Mohr et al. (1991) Nature 354:164–167; Guo et al. (1991) J. Biol. Chem. 266:1809–1819; Kittle et al. (1991) Genes Dev. 5:1009–1021; Doudna et al. (1989) PNAS 86:7402–7406; and Pattanju et al. (1992) Nuc. Acid Res. 20:5357–5364.

The efficiency of splicing of group II and group I introns can often be improved by, and in some instances may require, the addition of protein and/or RNA co-factors, such as maturases. (Michel et al. (1990) J. Mol. Biol. 216:585–610; Burke et al. (1988) Gene 71:259–271; and Lambowitz et al. (1990) TIBS 15:440–444). This can be especially true when more truncated versions of these introns are used to drive ligation by trans-splicing, with the maturase or other co-factor compensating for structural defects in the intron structure formed by intermolecular complementation by the flanking intron fragments. Genetic analysis of mitochondrial RNA splicing in Neurospora and yeast has shown, for example, that some proteins involved in splicing of group I and group II introns are encoded by host chromosomal genes, whereas others are encoded by the introns themselves. Several group I and group II introns in yeast mtDNA, for instance, encode maturases that function in splicing the intron that encodes them. These include group I introns Cob-I2, -I3, and I4, and group II introns cox1-I1 and -I2. Thus, the conditions for splicing of group I and group II introns can further comprise maturases and other co-factors as necessary to form a functional intron by the flanking intron sequences.

C. Nuclear pre-mRNA introns

Nuclear pre-mRNA splicing, like group II intron-mediated splicing, also proceeds through a lariat intermediate in a two-step reaction. In contrast to the highly conserved structural elements that reside within group II introns, however, the only conserved features of nuclear pre-mRNA introns are restricted to short regions at or near the splice junctions. For instance, in yeast these motifs are (i) a conserved hexanucleotide at the 5' splice, (ii) an invariant heptanucleotide, the UACUAAC box, surrounding the branch point A (underlined), and (iii) a generally conserved enrichment for pyrimidine residues adjacent to an invariant AG dinucleotide at the 3' splice site.

Two other characteristics of nuclear pre-mRNA splicing in vitro that distinguish it from autocatalytic splicing are the dependence on added cell-free extracts and the requirement for adenosine triphosphate (ATP). Once in vitro systems had been established for mammalian and yeast pre-mRNA splicing, it was found that a group of trans-acting factors, predominately made up of small nuclear ribonucleoprotein particles (snRNP's) containing U1, U2, U4, U5 and U6 RNA's was essential to the splicing process. Together with the discovery of autocatalytic introns, the demonstration that snRNAs were essential, trans-acting components of the spliceosome argued strongly that group II self-splicing and nuclear pre-mRNA splicing occurred by fundamentally equivalent mechanisms. According to this view, the snRNAs compensate for the low information content of nuclear introns and, by the formation of intermolecular RNA-RNA interactions, achieve the catalytic capability inherent in the intramolecular structure of autocatalytic introns.

Figure 9A:
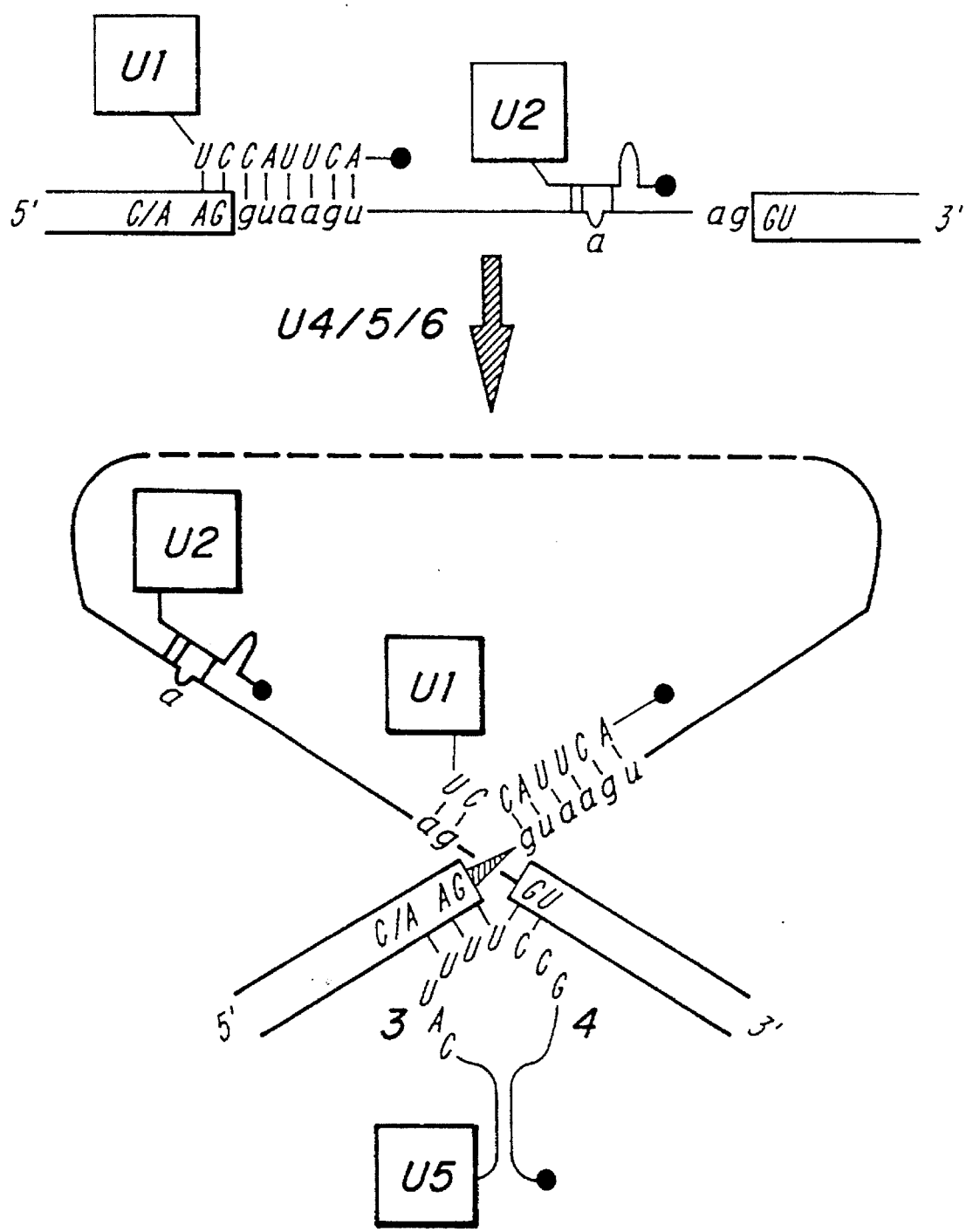
FIG. 9A illustrates the interaction between nuclear pre-mRNA introns and snRNPs.

As illustrated in FIG. 9A, consensus sequences of the 5' splice site and at the branchpoint are recognized by base pairing with the U1 and U2 snRNP's, respectively. The original proposal that the U1 RNA interacted with the 5' splice site was based solely on the observed nine-base-pair complementarity between the two mammalian sequences (Rogers et al. (1980)Nature 283:220). This model has since been extensively verified experimentally (reviewed in Steitz et al., in Structure and Function of Major and Minor snRNP Particles, M. L. Birnstiel, Ed. (Springer-Verlag, New York, 1988)). Demonstration of the Watson-Crick interactions between these RNAs was provided by the construction of compensatory base pair changes in mammalian cells (Zhuang et al. (1986) Cell 46:827). Subsequently, suppressor mutations were used to prove the interaction between U1 and the 5' splice site in yeast (Seraphin et al. (1988) EMBO J 7:2533).

The base pairing interaction between U2 and sequences surrounding the branchpoint was first tested in yeast (Parker et al. (1987) Cell 49:229), where the strict conservation of the branchpoint sequence readily revealed the potential for complementarity. The branchpoint nucleotide, which carries out nucleophilic attack on the 5' splice site, is thought to be unpaired (FIG. 9A), and is analogous to the residue that bulges out of an intramolecular helix in domain VI of group II introns. The base pairing interaction between U2 and the intron has also been demonstrated genetically in mammalian systems (Zhaung et al. (1989) Genes Dev. 3:1545). In fact, although mammalian branchpoint sequences are notable for their deviation from a strict consensus, it has been demonstrated that a sequence identical to the invariant core of the yeast consensus, CUAAC is the most preferred (Reed et al. (1989) PNAS 86:2752).

Genetic evidence in yeast suggests that the intron base pairing region at the 5' end of U1 RNA per se is not sufficient to specify the site of 5' cleavage. Mutation of the invariant G at position 5 of the 5' splice site not only depresses cleavage efficiency at the normal GU site but activates cleavage nearby; the precise location of the aberrant site varies depending on the surrounding context (Jacquier et al. (1985) Cell 43:423; Parker et al. (1985) Cell 41:107; and Fouser et al. (1986) Cell 45:81). Introduction of a U1 RNA, the sequence of which has been changed to restore base pairing capability at position 5, does not depress the abnormal cleavage event; it enhances the cleavage at both wild-type and aberrant sites. These results indicate that the complementarity between U1 and the intron is important for recognition of the splice-site region but does not determine the specific site of bond cleavage (Seraphin et al. (1988) Genes Dev. 2:125; and Seraphin et al. (1990) Cell 63:619).

With regard to snRNPs, genetic experiments in yeast have revealed that the U5 snRNP is an excellent candidate for a trans-acting factor that functions in collaboration with U1 to bring the splice sites together in the spliceosome. U5 is involved in the fidelity of the first and the second cleavage-ligation reactions. For example, a number of U5 mutants exhibit a distinct spectrum of 5' splice-site usage; point mutations with the invariant nine-nucleotide loop sequence (GCCUUUUAC) in U5 RNA allows use of novel 5' splice sites when the normal 5' splice site was mutated. For instance, splicing of defective introns was restored when positions 5 or 6 of the invariant U5 loop were mutated so that they were complementary to the nucleotides at positions 2 and 3 upstream of the novel 5' splice site. Likewise, mutational analysis has demonstrated the role of the U5 loop sequence in 3' splice site activation. For example, transcripts which are detective in splicing due to nucleotide changes in either one of the first two nucleotides of the 3' exon were subsequently rendered functional by mutations in positions 3 or 4 of the U5 loop sequence which permitted pairing with the mutant 3' exon. (See Newman et al. (1992) Cell 68:1); and Newman et al. (1991) Cell 65:115). It is suggested that first U1 base pairs with intron nucleotides at the 5' splice site during assembly of an early complex (also including U2). This complex is joined by a tri-snRNP complex comprising U4, U5 and U6 to form a Holliday-like structure which serves to juxtaposition the 5' and 3' splice sites, wherein U1 base pairs with intronic sequences at both splice site. (Steitz et al. (1992) Science 257:888–889).

While each of the U1, U2 and U5 snRNPs appear to be able to recognize consensus signals within the intron, no specific binding sites for the U4–U6 snRNP has been identified. U4 and U6 are well conserved in length between yeast and mammals and are found base paired to one another in a single snRNP (Siliciano et al. (1987) Cell 50:585). The interaction between U4 and U6 is markedly destabilized specifically at a late stage in spliceosome assembly, before the first nucleolytic step of the reaction (Pikienly et al. (1986) Nature 324: 341: and Cheng et al. (1987) Genes Dev. 1:1014). This temporal correlation, together with an unusual size and sequence conservation of U6, has lead to the understanding that the unwinding of U4 from U6 activates U6 for participation in catalysis. In this view, U4 would function as an antisense negative regulator, sequestering U6 in an inert conformation until it is appropriate to act (Guthrie et al. (1988) Annu Rev. Genet. 22:387). Recent mutational studies demonstrate a functional role for U6 residues in the U4–U6 interaction domain in addition to base pairing (Vanken et al. (1990) EMBO J 9:3397; and Madhani et al. (1990) Genes Dev. 4:2264).

Mutational analysis of the spliceosomal RNAs has revealed a tolerance of substitutions or, in some cases, deletion, even of phylogenetically conserved residues (Shuster et al. (1988) Cell 55:41; Pan et al. (1989) Genes Dev. 3:1887; Liao et al. (1990) Genes Dev. 4:1766; and Jones et al. (1990) EMBO J 9:2555). For example, extensive mutagenesis of yeast U6 has been carried out, including assaying the function of a mutated RNA with an in vitro reconstitution system (Fabrizio et al. (1990) Science 250:404), and transforming a mutagenized U6 gene into yeast and identifying mutants by their in vivo phenotype (Madhani et al. (1990) Genes Dev. 4:2264). Whereas most mutations in U6 have little or no functional consequence (even when conserved residues were altered), two regions that are particularly sensitive to nucleotide changes were identified: a short sequence in stem I (CAGC) that is interrupted by the *S. pombe* intron, and a second, six-nucleotide region (ACAGAG) upstream of stem I.

Figure 9B:
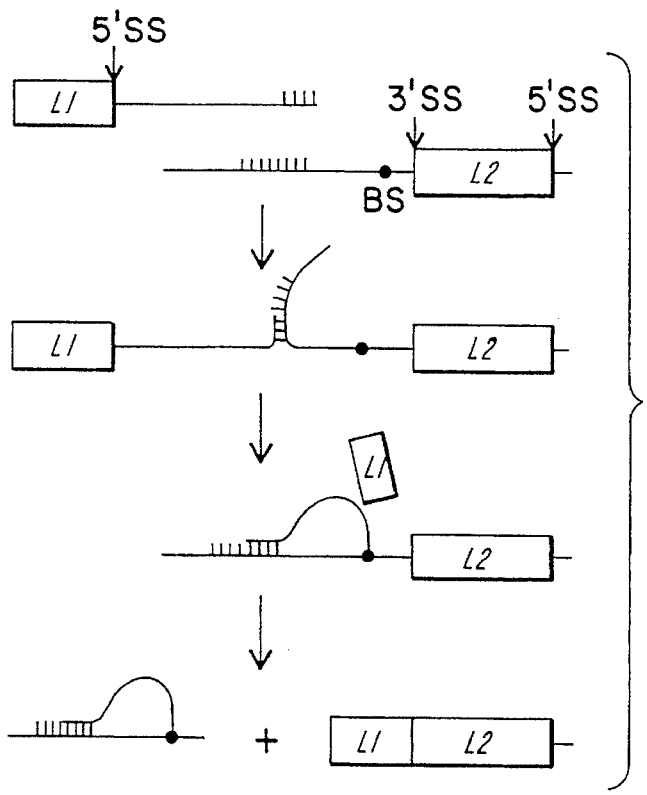
FIGS. 9B and 9C illustrate two embodiments for accomplishing nuclear pre-mRNA intron mediated trans-splicing.
Figure 9C:
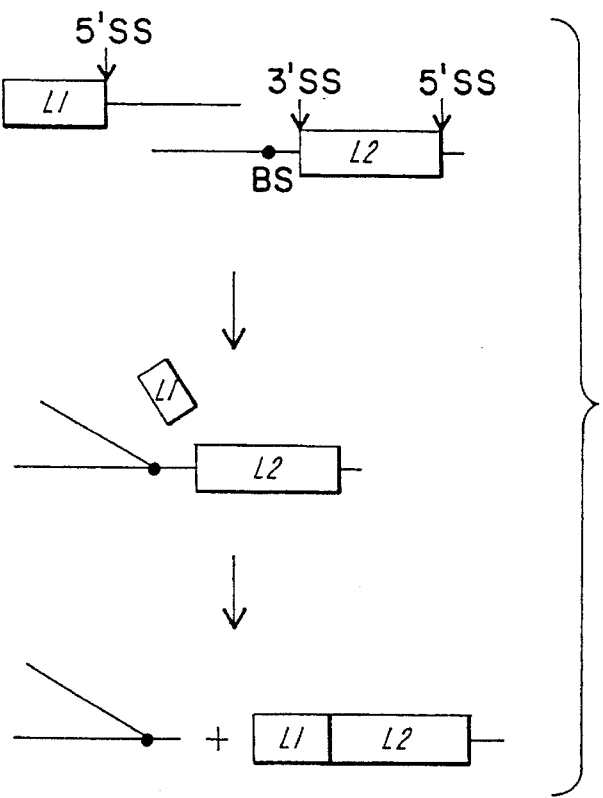

As described above for both group I and group II introns, exonic sequences derived from separate RNA transcripts can be joined in a trans-splicing process utilizing nuclear pre-mRNA intron fragments (Konarska et al. (1985) Cell 42:165–171; and Solnick (1985) Cell 42:157–164). In the trans-splicing reactions, an RNA molecule, comprising an exon and a 3' flanking intron sequences which includes a 5' splice site, is mixed with an RNA molecule comprising an exon and 5' flanking intronic sequences, including a 3' splice site, and a branch acceptor site. As illustrated in FIGS. 9B and 9C, upon incubation of the two types of transcripts (e.g. in a cell-free splicing system), the exonic sequences can be accurately ligated. In a preferred embodiment the two transcripts contain complementary sequences which allow base-pairing of the discontinuous intron fragments. Such a construct, as FIG. 9B depicts, can result in a greater splicing efficiency relative to the scheme shown in FIG. 9C in which no complementary sequences are provided to potentiate complementation of the discontinuous intron fragments.

The exon ligation reaction mediated by nuclear pre-mRNA intronic sequences can be carried out in a cell-free splicing system. For example, combinatorial exon constructs can be mixed in a buffer comprising 25 mM creatine phosphate, 1 mM ATP, 10 mM $MgCl_2$, and a nuclear extract containing appropriate factors to facilitate ligation of the exons (Konarska et al. (1985) Nature 313:552–557: Krainer et al. (1984) Cell 36:993–1005; and Dignam et al. (1983) Nuc. Acid Res. 11:1475–1489). The nuclear extract can be substituted with partially purified spliceosomes capable of carrying out the two transesterification reactions in the presence of complementing extracts. Such spliceosomal complexes have been obtained by gradiant sedimentation (Grabowski et al. (1985) Cell 42:345–353; and Lin et al. (1987) Genes Dev. 1:7–18), gel filtration chromatography (Abmayr et al. (1988) PNAS 85:7216–7220; and Reed et al. (1988) Cell 53:949–961), and polyvinyl alcohol precipitation (Parent et al. (1989) J. Mol. Biol. 209:379–392). In one embodiment, the spliceosomes are activated for removal of nuclear pre-mRNA introns by the addition of two purified yeast "pre-mRNA processing" proteins, PRP2 and PRP16 (Kim et al. (1993) PNAS 90:888–892; Yean et al. (1991) Mol. Cell Biol. 11:5571–5577; and Schwer et al. (1991) Nature 349:494–499).

II. Trans-splicing Combination of Exons

In one embodiment of the present combinatorial method, the intronic sequences which flank each of the exon modules are chosen such that gene assembly occurs in vitro through ligation of the exons, mediated by a trans-splicing mechanism. Conceptually, processing of the exons resembles that of a fragmented cis-splicing reaction, though a distinguishing feature of trans-splicing versus cis-splicing is that substrates of the reaction are unlinked. As described above, breaks in the intron sequence can be introduced without abrogating splicing, indicating that coordinated interactions between different portions of a functional intron need not depend on a covalent linkage between those portions to reconstitute a functionally-active splicing structure. Rather, the joining of independently transcribed coding sequences results from interactions between fragmented intronic RNA pieces, with each of the separate precursors contributing to a functional trans-splicing core structure.

The present trans-splicing system provides an active set of transcripts for trans-splicing wherein the flanking intronic sequences can interact to form a reactive complex which promotes the transesterification reactions necessary to cause the ligation of discontinuous exons. In one embodiment, the exons are flanked by portions of one of a group I or group II intron, such that the interaction of the flanking intronic sequences is sufficient to produce an autocatalytic core capable of driving ligation of the exons in the absence of any other factors. While the accuracy and/or efficiency of these autocatalytic reactions can be improved, in some instances, by the addition of trans-acting protein or RNA factors, such additions are not necessary.

In another embodiment, the exon modules are flanked by intronic sequences which are unable, in and of themselves, to form functional splicing complexes without involvement of at least one trans-acting factor. For example, the additional trans-acting factor may compensate for structural defects of a complex formed solely by the flanking introns. As described above, domain V of the group II intron class can be removed from the flanking intronic sequences, and added instead as a trans-acting RNA element. Similarly, when nuclear pre-mRNA intron fragments are utilized to generate the flanking sequences, the ligation of the exons requires the addition of snRNPs to form a productive splicing complex.

Figure 5:
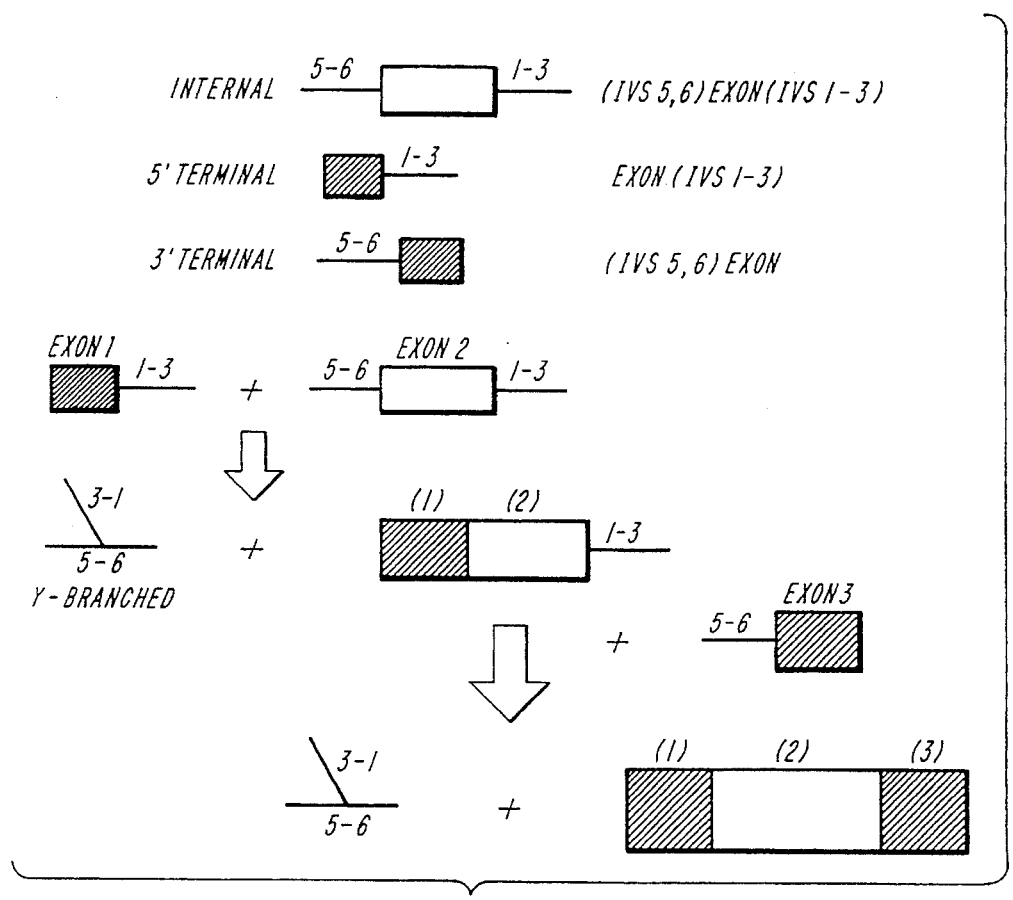
FIG. 5 is a schematic representation of a trans-splicing reaction between discontinuous exon sequences.

In an illustrative embodiment, the present combinatorial approach can make use of group II intronic sequences to mediate trans-splicing of exons. For example, as depicted in FIG. 5, internal exons can be generated which include domains V and VI at their 5' end, and domains I–III at their 3' end. The nomenclature of such a construct is (IVS5,6)Exon(IVS1-3), representing the intron fragments and their orientation with respect to the exon. Terminal exons are likewise constructed to be able to participate in trans-splicing, but at only one end of the exon. A 5' terminal exon, in the illustrated group II system, is one which is flanked by domains I–III at its 3' end [Exon(IVS1-3)] and is therefore limited to addition of further exonic sequences only at that end; and a 3' terminal exon is filmed by intron sequences (domains V and VI) at only its 5' end [(IVS5,6)Exon]. Under conditions which favor trans-splicing, the flanking intron sequences at the 5' end of one exon and the 3' end of another exon will associate to form a functionally active complex by intermolecular complementation and ligate the two exons together.

Figure 6:
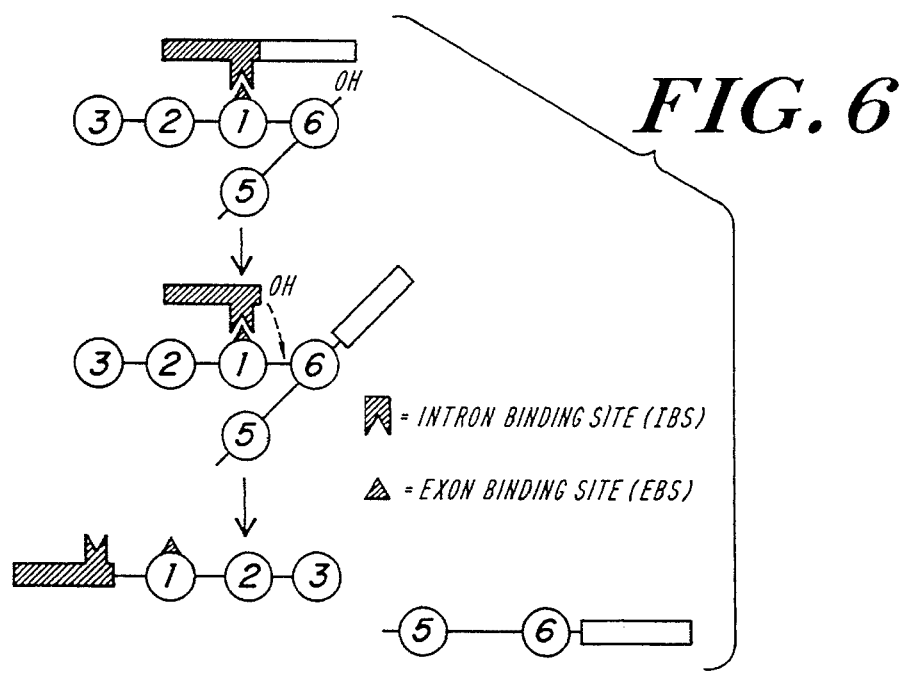
FIG. 6 illustrates how a reverse-splicing reaction can be utilized to activate exons for subsequent combinatorial trans-splicing.

In another embodiment of the present trans-splicing combinatorial method, the exons, as initially admixed, lack flanking intronic sequences at one or both ends, relying instead on a subsequent addition of flanking intronic fragments to the exons by a reverse-splicing reaction. Addition of the flanking intron sequences, which have been supplemented in the exon mixture, consequently activates an exon for trans-splicing. FIG. 6 illustrates how the reverse-splicing reaction of group II introns can be used to add domains I–IV to the 3' end of an exon as well as domains I–III to the 5' end of an exon. As shown in FIG. 6, the reversal reaction for branch formation can mediate addition of 3' flanking sequences to an exon. For example, exon modules having 5' intron fragments (e.g. domains V–VI) can be mixed together with little ligation occurring between exons. These exons are then mixed with a 2'-5' Y-branched intron resembling the lariate-IVS, except that the lariat is discontinuous between domain IV and V. The reverse-splicing is initiated by binding of the IBS 1 of the 5' exon to the EBS 1 of the Y-branched intron, followed by nucleophilic attack by the 3'-OH of the exon on the 2'-5' phosphodiester bond of the branch site. This reaction, as depicted in FIG. 6, results in the reconstitution of the 5' splice-site with a flanking intron fragment comprising domains I–III.

While FIG. 6 depicts both a 5' exon and 3' exon, the reverse splicing reaction can be carried out without any 3' exon, the IBS sequence being at the extreme 3' end of the transcript to be activated. Alternatively, to facilitate addition of 5' flanking sequences, an exon can be constructed so as to further include a leader sequence at its 5' end. As shown in FIG. 6, the leader (e.g. the 5' exon) contains an IBS which defines the splice junction between the leader and "mature" exon. The leader sequence can be relatively short, such as on the order of 2–3 amino acid residues (e.g. the length of the IBS). Through a reverse self-splicing reaction using a discontinuous 2'-5' branched intron, the intronic sequences can be integrated at the splice junction by reversal of the two transterfication steps in forward splicing. The resulting product includes the mature exon having a 5' flanking intron fragment comprising domains V and VI.

Addition of intronic fragments by reverse-splicing and the subsequent activation of the exons presents a number of control advantages. For instance, the IBS:EBS interaction can be manipulated such that a variegated population of exons is heterologous with respect to intron binding sequences (e.g. one particular species of exon has a different IBS relative to other exons in the population). Thus, sequential addition of intronic RNA having discrete EBS sequences can reduce the construction of a gene to non-random or only semi-random assembly of the exons by sequentially activating only particular combinatorial units in the mixture. Another advantage derives from being able to store exons as part of a library without self-splicing occurring at any significant rate during storage. Until the exons are activated for trans-splicing by addition of the intronic sequences to one or both ends, the exons can be maintained together in an effectively inert state.

When the interactions of the flanking introns are random, the order and composition of the internal exons of the combinatorial gene library generated is also random. For instance, where the variegated population of exons used to generate the combinatorial genes comprises N different internal exons, random trans-splicing of the internal exons can result in $N^y$ different genes having y internal exons. Where 5 different internal exons are used (N=5) but only constructs having one exon ligated between the terminal exons are considered (i.e. y=1) the present combinatorial approach can produce 5 different genes. However, where y=6, the combinatorial approach can give rise to 15,625 different genes having 6 internal exons, and 19,530 different genes having from 1 to 6 internal exons (e.g. $N^1 + N^2 \ldots + N^{y-1} + N^y$). It will be appreciated that the frequency of occurrence of a particular exonic sequence in the combinatorial library may also be influenced by, for example, varying the concentration of that exon relative to the other exons present, or altering the flanking intronic sequences of that exon to either diminish or enhance its trans-splicing ability relative to the other exons being admixed.

Figure 7:
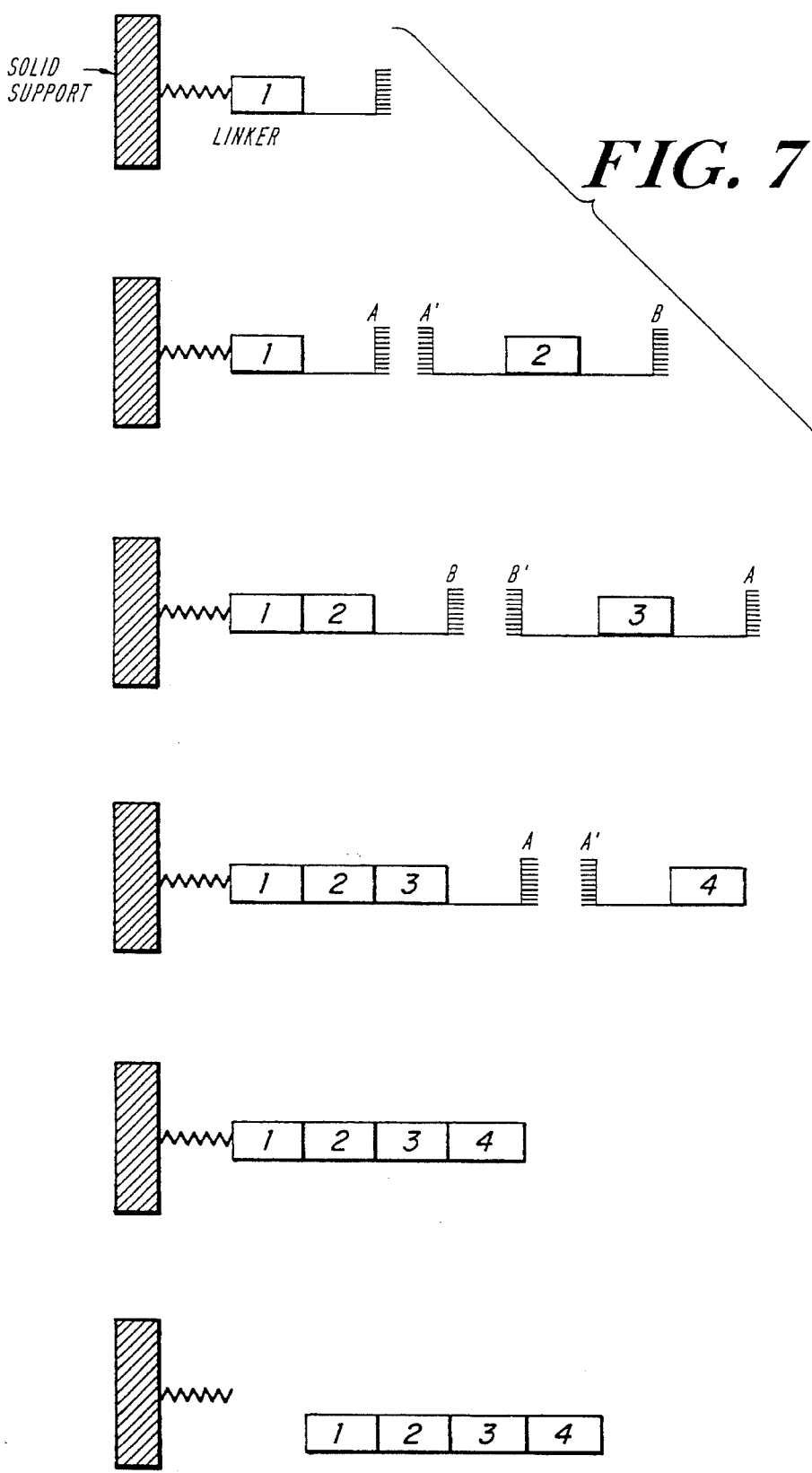
FIG. 7 illustrates an ordered gene assembly mediated by trans-splicing of exons flanked with nuclear pre-mRNA intron fragments.

However, the present trans-splicing method can also be utilized for ordered gene assembly, and carried out in much the same fashion as automated oligoucleotide or polypeptide synthesis. FIG. 7 describes schematically the use of resin-bound combinatorial units in the ordered synthesis of a gene. In the illustrated example, mammalian pre-mRNA introns are used to flank the exon sequences, and splicing is catalyzed by addition of splicing extract isolated from mammalian cells. The steps outlined can be carried out manually, but are amenable to automation. The 5' terminal exon sequence (shown as exon 1 in FIG. 7) is directly followed by a 5' portion of an intron that begins with a 5' splice-site consensus sequence, but does not include the branch acceptor sequence. The flanking intron fragment further includes an added nucleotide sequence, labeled "A" in the diagram, at the 3' end of the downstream flanking intron fragment. The 5' end of this terminal combinatorial unit is covalently linked to a solid support.

In the illustrated scheme, exon 2 is covalently joined to exon 1 by trans-splicing. The internal shuffling unit that contains exon 2 is flanked at both ends by intronic fragments. Downstream of exon 2 are intron sequences similar to those downstream of exon 1, with the exception that in place of sequence A the intronic fragment of exon 2 has an added sequence B that is unique, relative to sequence A. Exon 2 is also preceded by a sequence complementary to A (designated A'), followed by the nuclear pre-mRNA intron sequences that were not included downstream of exon 1, including the branch acceptor sequence and 3' splice-site consensus sequence AG.

To accomplish the trans-splicing reaction, the shuffling units are allowed to anneal by hydrogen bonding between the complementary intronic sequences (e.g. A and A'). Then, trans-splicing is catalyzed by the addition of a splicing extract which contains the appropriate snRNPs and other essential splicing factors. The Y-branched intron that is generated, and any other by-products of the reaction, are washed away, and a ligated exon 1 and 2 remain bound to the resin. A second internal shuffling unit is added. As shown in FIG. 7, the exon (exon 3) has flanking intronic fragments which include a sequence B' in the upstream fragment and a sequence A in the downstream fragment. The nucleotide sequence B' is unique relative to sequence A', and is complementary to sequence B. As above, the RNA is allowed to anneal through the B:B' sequences, splicing of the intervening sequences is catalyzed by the addition of extract, and reaction by-products other than the resin bound exons are washed away. While FIG. 7 depicts a non-random assembly of a gene, it is understood that semi-random assembly can also be carried out, such as would occur, for example, when exon 3 is substituted with a variegated population of exons combinatorial units.

This procedure can be continued with other exons, and may be terminated by ligation of a 3' terminal shuffling unit that contains an exon (exon 4 in the FIG. 7) with upstream intron sequence (and either the A' or B' sequence, as appropriate), but lacking any downstream intron sequences. After the 3' terminal exon is added, the assembled gene can be cleaved from the solid support, reverse transcribed, and the cDNA amplified by PCR and cloned into a plasmid by standard methods.

Figure 11:
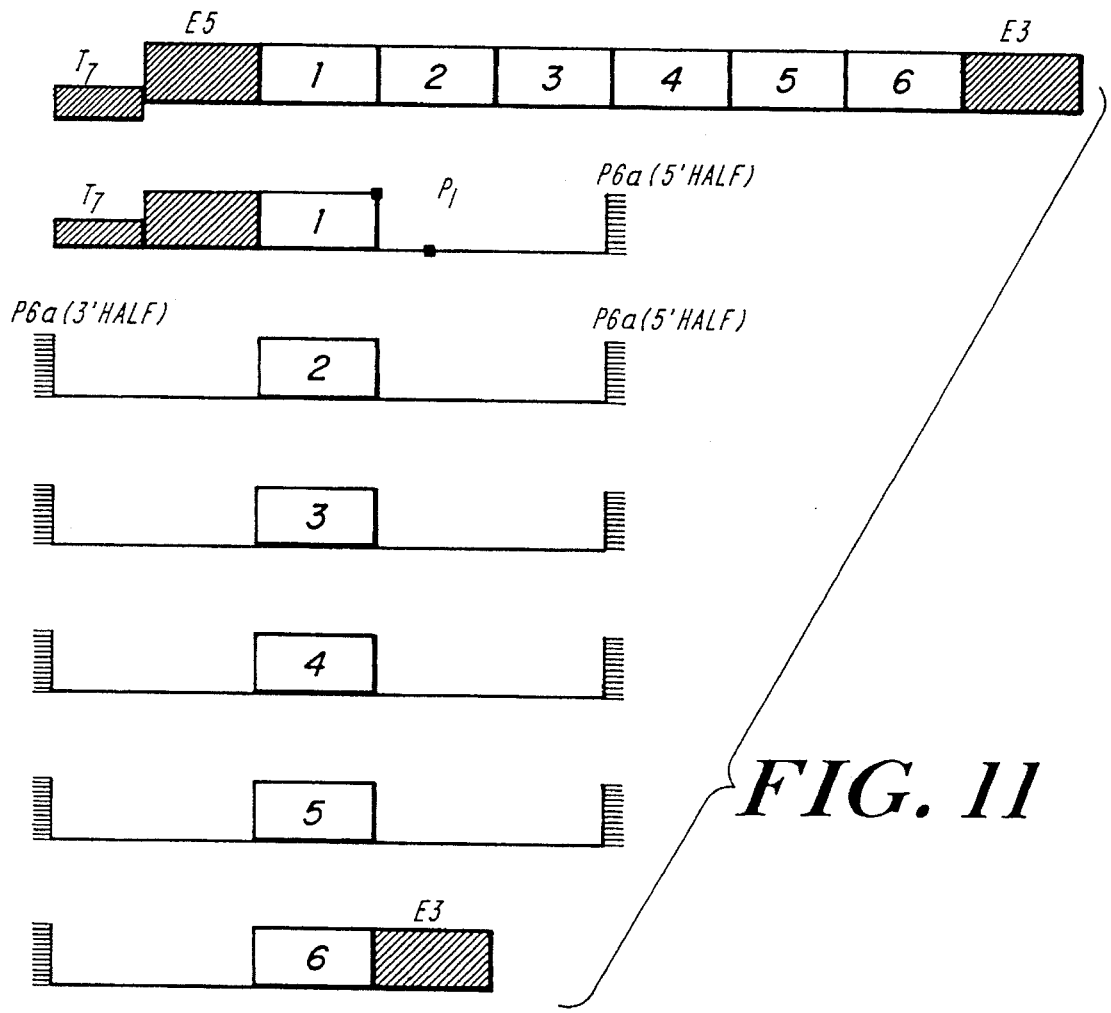
FIG. 11 depicts one example of how group I intron sequences can be used to shuffle group II intron domains.

The domain shuffling experiments described to yield novel protein coding genes can also be used to create new ribozymes. FIG. 11 depicts one example of how group I intron sequences can be used to shuffle group II intron domains. In the illustrative embodiment, the group II intron consists of 6 domains and is flanked by exons (E5 and E3); in this instance, E5 is shown to include a T7 promoter. The six shuffling competent constructs diagrammed in the figure can be made either by standard site directed mutagenesis and cloning or by the reversal of splicing. The 5' terminal exon is followed by sequences from the T4 td intron, beginning with the first nucleotide of the intron and including the internal guide sequence, and continuing through the 5' half of the P6a stem (i.e. including half of L6). The last nucleotide of the exon is a U. The internal guide sequence of the intron is changed by site directed mutagenesis so that it is complementary to the last 6 nt of the exon. This will allow the P1 stem to form. The U at the end of the exon is based paired with a G in the internal guide sequence. The 3' terminal "exon", in this case, consists of group II intron domain 6 plus E3. The 3' terminal exon is preceded by the T4 td intron, beginning with the 3' half of P6a and continuing through to the end of the intron. The last nucleotide of the intron is followed by the first nucleotide of group II intron domain 6. The internal exons each consist of a group II intron domain but, in contrast to the terminal exons, each internal exon is flanked by group I intron sequences on both sides. In each case, the internal guide sequence of the group I intron is changed so as to be complementary to the last 6 nts of the exon and, in each case, the last nucleotide of the exon is a U.

Constructing a library of group II domains flanked by group I intronic sequence allows new group II ribozymes to be assembled from these units by random exon shuffling using conditions that allow for efficient trans-splicing of "exons" flanked by these group I intron sequences. For instance, if only one E5:d1 and d6:E3 are used, but a variegated population of d2–d5, the assembled genes will all have the same 5' and 3' terminal exons, but will have different arrangements and numbers of internal exons. An E3 specific primer plus reverse transcriptase can be used to make cDNA of the library of recombined transcript. T7 and E3 specific primers can be used to amplify the assembled genes by PCR, and RNA transcripts of the assembled gene can be generated using T7 polymerase. The RNA can be incubated under self splicing conditions appropriate for group II splicing. Molecules that are capable of self splicing will yield intron lariats that migrate anomalously slow on denaturing polyacrylamide gels. The lariats can be gel purified and represent active ribozymes. The isolated lariats can be specifically debranched with a HeLa debranching activity. Reverse transcription and PCR can be used to make and amplify cDNA copies of the ribozymes. The primers used for the PCR amplification will include exon sequences so that each amplified intron will be flanked by a 5' and a 3' exon. The last 6 nt of the 5' exon will be complementary to EBS 1. The amplified DNA can be cloned into a plasmid vector and individual interesting variants isolated and studied in detail.

Figure 12:
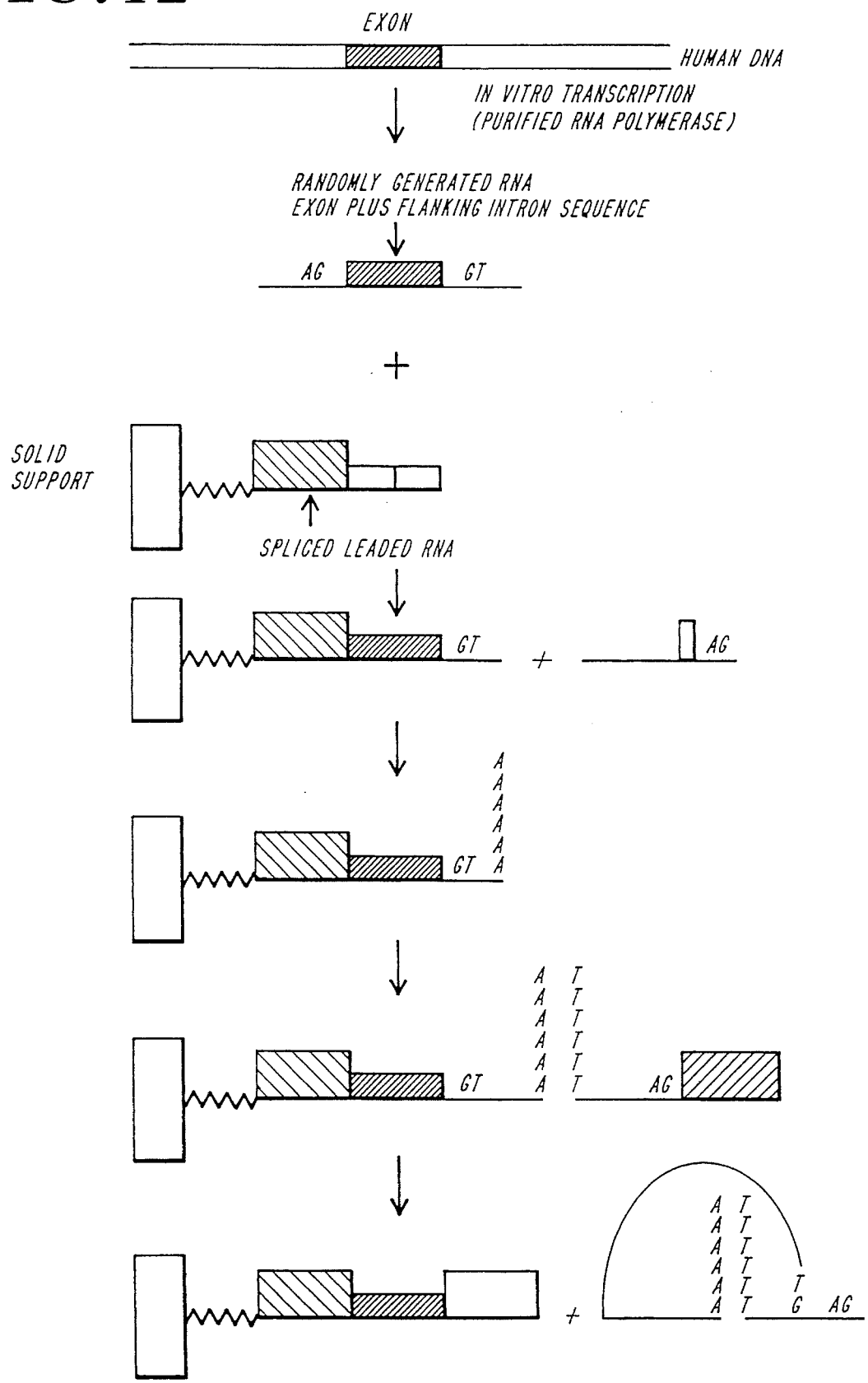
FIG. 12 illustrates an "exon-trap" assay for identifying exons from genomic DNA, utilizing trans-splicing mediated by discontinuous nuclear pre-mRNA intron fragments.

FIG. 12 illustrates an "exon-trap" assay for identifying exons (in the traditional use of the term) from genomic DNA, utilizing trans-splicing mediated by discontinuous nuclear pre-mRNA intron fragments. One advantage of this method is that the DNA does not have to be cloned prior to using the method. In contrast to prior techniques, the starting material of the exon-trap assay could ultimately be total human genomic DNA. In addition, the present method described herein is an in vitro method, and can be easily automated.

In the first step, purified RNA polymerase II is used to transcribe the target DNA. In the absence of the basal transcription factors, Pol II will randomly transcribe DNA (Lewis et al. (1982) Enzymes 15: 109–153). FIG. 12 shows that some of these transcripts will contain individual exons flanked by intron sequences. Since human exons are small, typically less than 300 nt (Hawkins et al. (1988) Nucleic Acids Res. 16, 9893–9908) and introns are large (up to 200,000 nt, Maniatis, T. (1991) Science 251, 33–34) most transcripts will contain either zero or one exon. In the illustrative embodiment, a spliced leader RNA of, for instance, trypanosome or nematode (Agabian (1990) Cell 61, 1157–1160), is covalently linked to a solid support by its 5' end. The RNA generated by random transcription of the genomic DNA is mixed with the immobilized spliced leader and splicing is catalyzed using splicing extract. The resin is then washed to remove unwanted reaction products, such as unreacted RNA and the splicing extract.

Furthermore, in a subsequent step, an in vitro polyadenlyation reaction (for example, Ryner et al. (1989) Mol. Cell. Biol., 9, 4229–4238) can be carried out which adds oligo-A (up to a length of 300 nt) to the 3' end of the RNA. FIG. 12 shows that an RNA transcript, generated by in vitro transcription of a plasmid having an oligo T stretch, followed by the 3' portion of an intron (including the branch acceptor site and the AG dinucleotide), followed by an exon, can be annealed to the immobilized polyadenylated RNA by hydrogen bonding between the poly-A and poly-T sequences. In vitro trans-splicing, catalyzed by splicing extract, will join the known 3' exon to the "trapped" exon. The RNA can then be stripped from the column, copied to DNA by reverse transcriptase and amplified by PCR using primers to the 5' leader and known 3' exon. The amplified DNA that contains a trapped exon will be larger than the side product that results from splicing of the spliced leader exon to the known 3' exon. Thus, the amplified DNA that contains trapped exons can be selected by size.

Moreover, a "capping" reaction can be done to eliminate products that do not contain a trapped exon. After the step of mixing genomically derived RNA with the immobilized exon, a "capping RNA", with a 3' splice site and a 3' exon, can be added and splicing catalyzed by the addition of splicing extract. The 3' exon of the capping RNA is different from the 3' exon of the RNA shown with the oligo-T stretch. The capping RNA is one which will trans-splice very efficiently to any spliced leader RNA which has not already participated in a splicing reaction; but, will splice less efficiently to immobilized RNAs that have a trapped exon ligated to them as the capping RNA lacks a poly-T sequence to anneal to the trapped exon. Therefore, after the capping reaction, the step shown for splicing of the oligo-T containing construct will result, primarily, in the generation of the desired (leader/trapped exon/known exon) product and not in the generation of the unwanted (5' leader/3' known exon) product.

III. Cis-splicing Combination of Exons

In yet another embodiment, the combinatorial method can be carried out in a manner that utilizes the flanking intronic sequences in a cis-splicing reaction to generate a combinatorial gene library. As illustrated schematically in FIG. 10, the actual combinatorial event takes place at the DNA level through annealing of complementary sequences within the intron encoding fragments. Briefly, complementary DNA strands are synthesized which correspond to the exonic sequences and flanking intron fragments. As used herein, the term (+) strand refers to the single-stranded DNA that is of the same polarity as a trans-splicing RNA transcript. That is, intronic sequences flanking the 5' end of the exon represent a 3' fragment of an intron. Likewise, the term (−) strand refers to the single stranded DNA which is complementary to the (+) strand (e.g. of opposite polarity).

The 5' and 3' ends of each of the (+) and (−) strands are complementary and can therefore mediate concatenation of single-stranded DNA fragments to one and other through basepairing. In the exemplary illustration of FIG. 10, the exon sequences are flanked by group II domains IV–VI at one end, and domains I–IV at the other. A library of combinatorial units representative of a number of different exons is generated, such as by PCR or digestion of double-stranded plasmid DNA, to include both (+) and (−) strands. The units are combined under denaturing conditions, and then renatured. Upon renaturation, the sequences corresponding to domain IV at the 3' end of one (+) strand unit can anneal with the complementary domain IV sequences at the 3' end of a (−) strand unit, resulting in concatenation of combinatorial units (see FIG. 10).

Double-stranded DNA can be generated from the concatenated single-stranded units by incubating with a DNA polymerase, dNTPs, and DNA ligase; and the resulting combinatorial genes subsequently cloned into an expression vector. In one instance, 5' terminal and 3' terminal combinatorial units can be used and the double-stranded genes can be amplified using PCR anchors which correspond to sequences in each of the two terminal units. The PCR primers can further be used to add restriction endonuclease cleavage sites which allow the amplified products to be conveniently ligated into the backbone of an expression vector. Upon transcription of the combinatorial gene, the intronic RNA sequences will drive ligation of the exonic sequences to produce an intron-less transcript.

While FIG. 10 demonstrates one embodiment which utilizes group II introns, the combinatorial process can be carried out in similar fashion using either group I intron sequences or nuclear pre-mRNA intron sequences.

IV. Circular RNA Transcripts

In addition to generating combinatorial gene libraries, the trans-splicing exon constructs of the present invention have a number of other significant uses. For instance, the present trans-splicing constructs can be used to produce circular RNA molecules. In particular, exon constructs flanked by either group II or nuclear pre-mRNA fragments can, under conditions which facilitate exon ligation by trans-splicing of the flanking intron sequences, drive the manufacture of circularly permuted exonic sequences in which the 5' and 3' ends of the same exon are covalently linked via a phosphodiester bond.

Circular RNA moieties generated in the present invention can have several advantages over the equivalent "linear" constructs. For example, the lack of a free 5' or 3' end may render the molecule less susceptible to degradation by cellular nucleases. Such a characteristic can be especially beneficial, for instance, in the use of ribozymes in vivo, as might be involved in a particular gene therapy. In the instance of generating ribozymes, the "exonic" sequences circularized are not true exons in the sense that they encode proteins, rather, the circularized sequences are themselves intronic in origin, and flanked by other trans-acting intron fragments.

However, the circularization of mature messenger-RNA transcripts can also be beneficial, by conferring increased stability as described above, as well as potentially increasing the level of protein translation from the transcript. To illustrate, a ribosome which has completed translation of a protein from the present circular transcript may continue to track around the transcript without dissociating from it, and hence renew synthesis of another protein. Alternatively, the ribosome may dissociate after translation is completed but, by design of the circular transcript, will disengage the transcript proximate to the start site and thereby provide an increased probability that the ribosome will rebind the transcript and repeat translation. Either scenario can provide a greater level of protein translation from the circular transcript relative to the equivalent linear transcript.

Figure 13A:
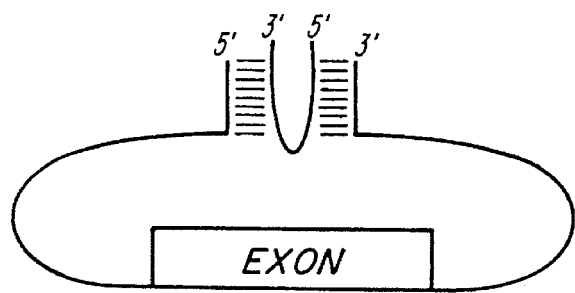
FIG. 13A shows a nucleic acid construct, designated (IVS5,6)-exon-(IVS1-3), which can mediate trans-splicing between heterologous exons, as well as be used to generate circular RNA transcripts.
Figure 13B:
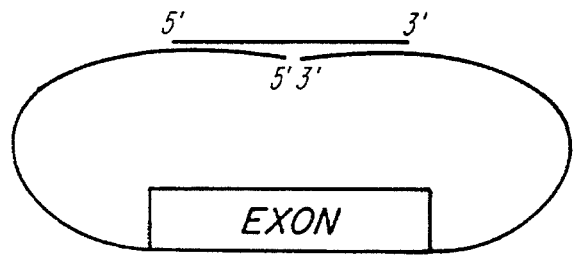
FIGS. 13B–C depict two examples of nucleic acid constructs, designated (3'-half-IVS)-exon-( 5'-half-IVS), which can mediate trans-splicing between heterologous exons, as well as be used to generate circular RNA transcripts.
Figure 13C:
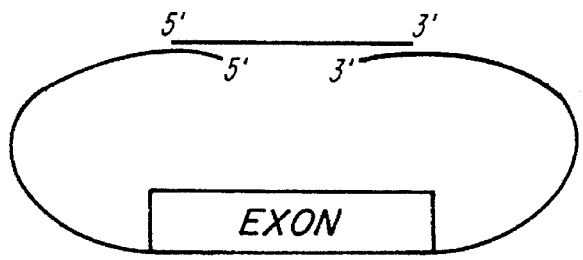

FIGS. 13A–C depicts three examples of intron fragment constructs, designated (IVS5,6)-exon-(IVS1-3), and (3'-half-IVS)-exon-(5'-half-IVS), which, in addition to being capable of driving trans-splicing between heterologous exons as described above, can also be used to generate circular RNA transcripts. The (IVS5,6)-exon-(IVS1-3) transcript comprises the group II intron domains V and VI at the 5' end of the exon, and domains I–III at the 3' end of the exon. The (3'-half-IVS)-exon-(5'-half-IVS) is a similar construct, but replaces the group II domains V–VI and I–III with fragments corresponding to the 3'-half and 5'-half of a nuclear pre-mRNA intron. As described in Examples 1 and 2 below, each of these transcripts can be shown to drive intramolecular ligation of the exon's 5' and 3' end to form circular exons.

Figure 14:
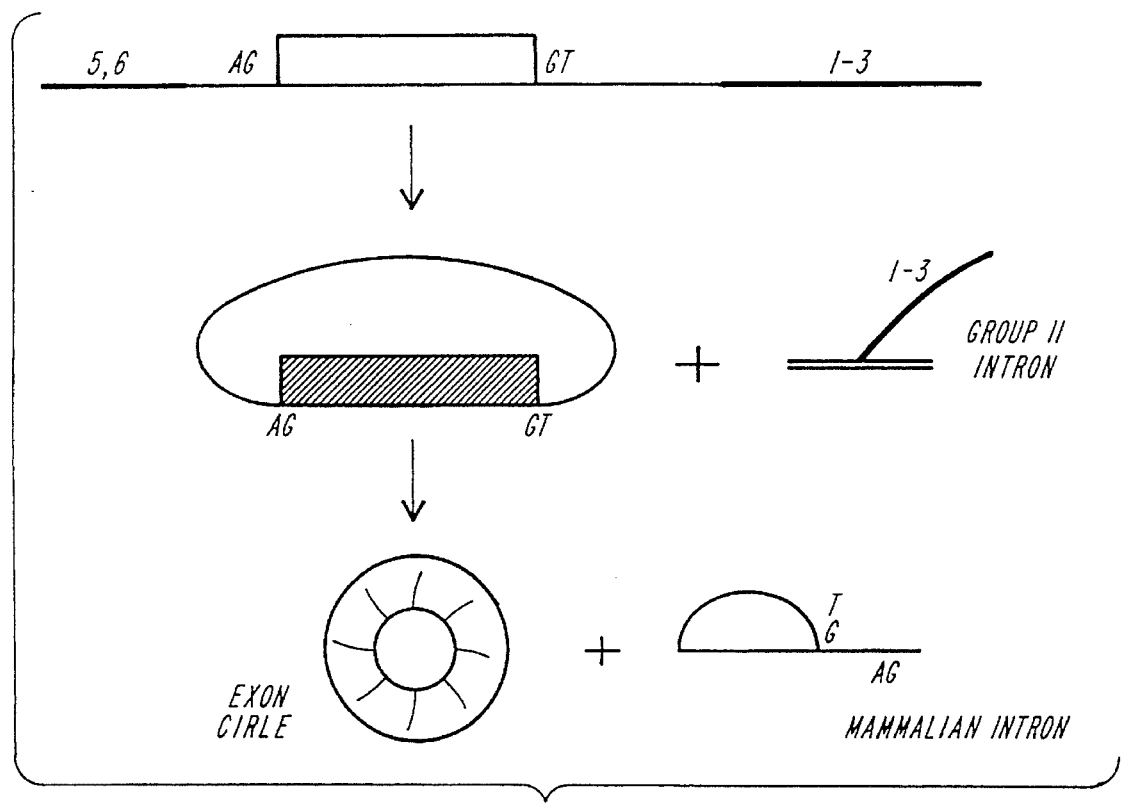
FIG. 14 shows how group II intronic fragments can be utilized to covalently join the ends of a nuclear pre-mRNA transcripts having flanking nuclear pre-mRNA intron fragments, such that the flanking nuclear pre-mRNA intron fragments can subsequently drive ligation of the 5' and 3' end of the exonic sequences.

Furthermore, as set forth in Example 2, a preferred embodiment of an exon construct using mammalian pre-mRNA intron sequences to generate circular transcripts provides an added structural element that brings together the 5' and 3' ends of the flanking pre-mRNA intron fragments. The addition of such structural elements has been demonstrated to greatly improve the efficiency of the intramolecular splicing reaction. For example, the ends of the intronic fragments can be non-covalently linked as shown in FIGS. 13B and C, by hydrogen bonding between complementary sequences. Alternatively, the ends of the nuclear pre-mRNA intron fragments can be covalently closed. In an illustrative embodiment, FIG. 14 shows how group II intronic fragments can be utilized to covalently join the ends of the nuclear pre-mRNA transcripts having flanking nuclear pre-mRNA intron fragments, which subsequently drive ligation of the 5' and 3' end of the exonic sequences.

Figure 15A:
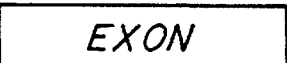
FIGS. 15A–C As illustrate how intronic ends of the same molecule can be brought together by a nucleic acid "bridge" which involves hydrogen bonding between the intronic fragments flanking an exon and a second discrete nucleic acid moiety.
Figure 15B:
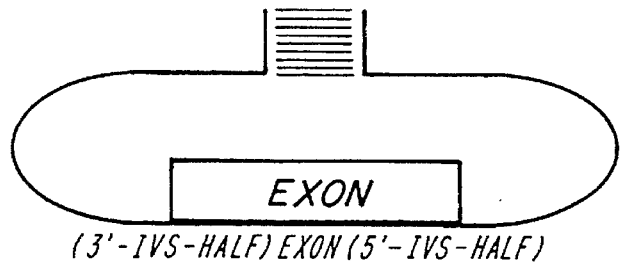
Figure 15C:
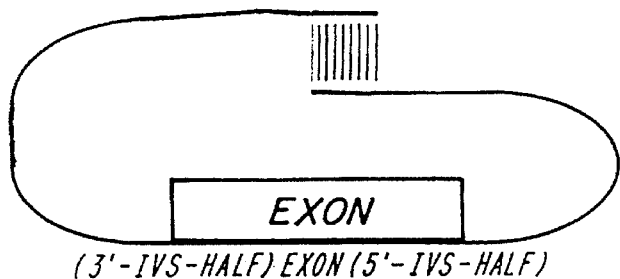

In yet another embodiment, the intronic ends can be brought together by a nucleic acid "bridge" which involves hydrogen bonding between the intronic fragments flanking the exon and a second discrete nucleic acid moiety. As illustrated in FIGS. 15A–C, such nucleic acid bridges can be formed a number of ways. Each of the splicing bridges shown differ from each other in either the orientation of the bridge oligonucleotide when base-paired to the flanking intron fragments, in the size of the bridging oligonucleotide, or both. For instance, the bridge oligonucleotide shown in FIG. 15A base-pairs in an orientation which can result in a stem-structure similar to the (3'IVS-half)-exon-(5' IVS-half) construct depicted in FIG. 13B. Moreover, when a bridge similar to one shown in FIG. 15C is used, and the 5' and 3' ends of the flanking introns base-pair some distance apart in the linear sequence of the bridge, the bridge oligonucleotide mayitself comprise the branch acceptor site. For example, the bridge oligonucleotide can be an RNA transcript comprising the yeast branch site consensus sequence UACUAAC in a portion of the bridge sequence which does not base-pair with the intronic fragments of the exon construct.

Figure 15D:
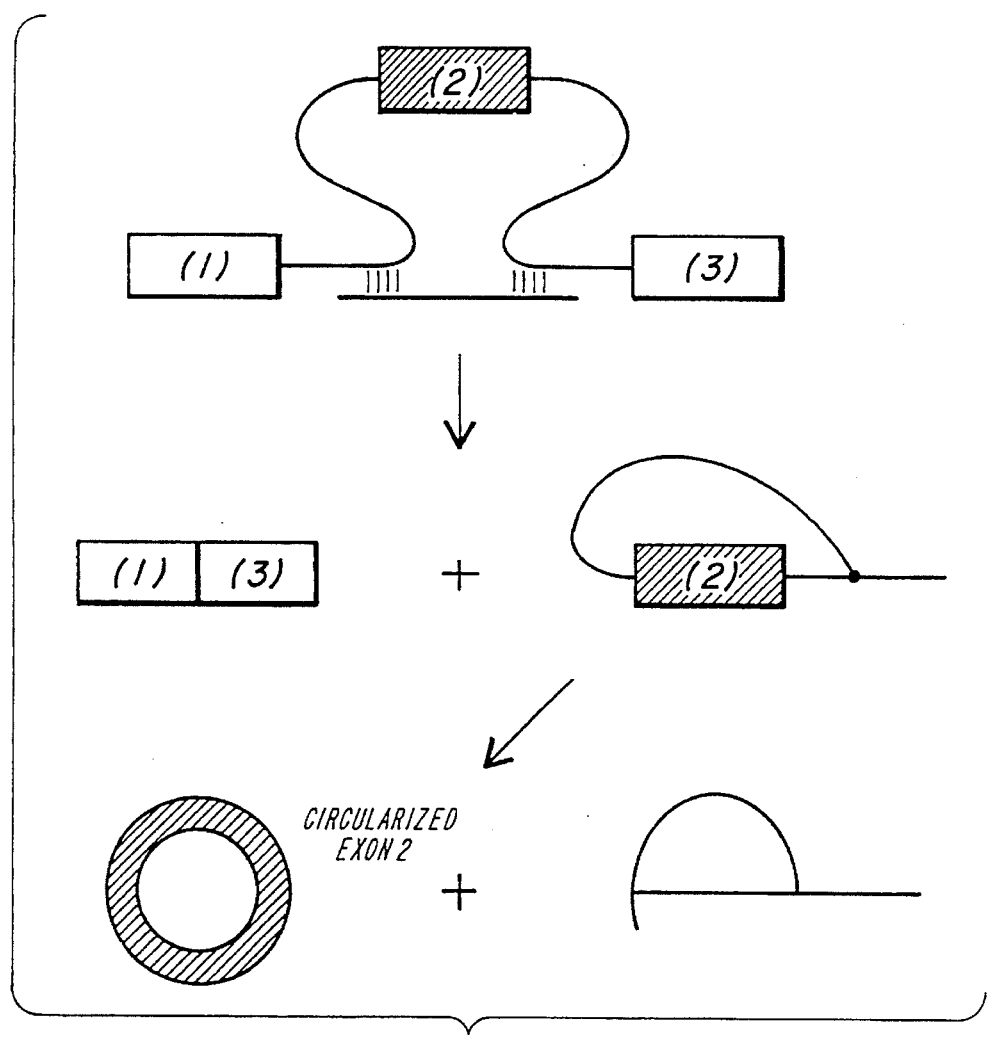
FIG. 15D shows, in an illustrative embodiment, how a nucleic acid bridge can be used to direct alternative splicing by "exon skipping".

Oligonucleotide bridges useful in driving the circularization of exon transcripts can also be used to direct alternative splicing by "exon skipping", which may be useful, for example, in disrupting expression of a particular protein. As shown in FIG. 15D, the splicing of exons 1 and 3 to each other can be the result of an oligonucleotide which loops out exon 2, effectively bringing together two complementary halves of the intronic sequences flanking exons 1 and 3. As shown in FIG. 15D, exon 2 can, in fact, be spliced into a circular RNA.

Figure 16:
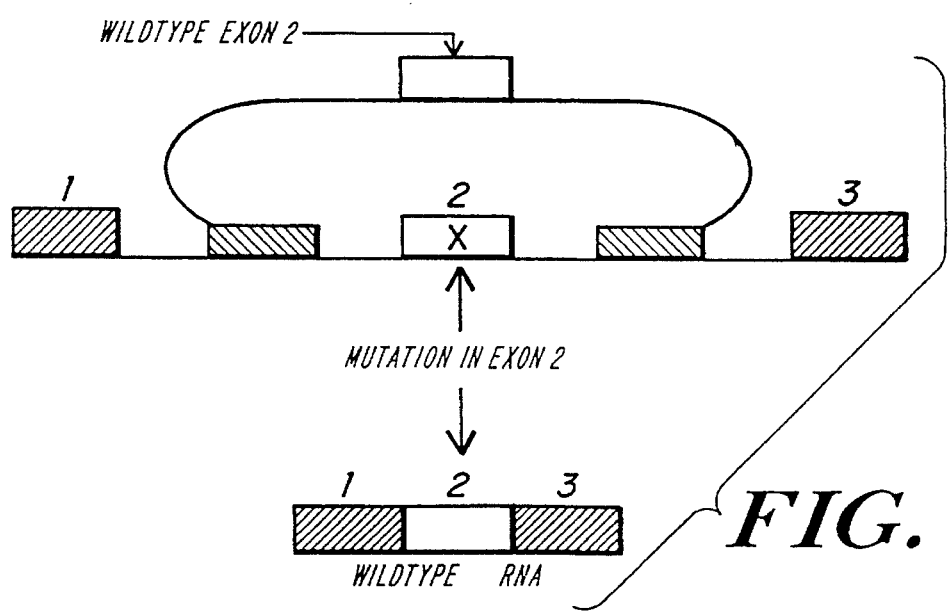
FIG. 16 illustrates a nucleic acid construct useful in mediating the alternate splicing of an exon through a trans-splicing-like mechanism.

Carrying the bridging nucleotide one step further, FIG. 16 illustrates the use of an exon construct useful in mediating the alternate splicing of an exon through a trans-splicing-like mechanism. For instance, a wild-type exon can be transspliced into an mRNA transcript so as to replace an exon in which a mutation has arisen. The wild-type exon construct comprises flanking intronic sequences which include sequences complementary to a portion of the continuous introns which connect exons 1, mutant exon 2, and exon 3. Thus, through a trans-splicing event as described above, some of the resulting mature mRNA transcripts will include the wild-type exon 2.

EXAMPLE 1

Group II Introns Can Mediate Circularization Of Exon Sequences

The (IVS 5,6) -exon- (IVS 1-3) RNA transcript, shown in FIG. 13A, was synthesized from plasmid pINV1 (Seg. ID No. 1). The intronic sequences correspond to the half molecules generated by interruption of the 5 g intron of the yeast mitochondrial oxi3 gene in domain IV; and the exonic sequences are the exon sequences E5 and E3 which are naturally disposed at the 5' and 3' ends of the 5 g intron, respectively. To construct pINV1, the Sac I-Hind III fragment of pJDI5'-75 (Jarrell et al. (1988) Mol. Cell Biol. 8:2361–2366) was isolated and the Hind III site was filled in with Klenow fragment. This DNA was ligated to pJDI3'-673 (Jarrell et al., supra) that had been cleaved with Sac I and Sma I. The RNA splicing substrates were made by in vitro transcription using T7 RNA polymearse.

Transcription, RNA purification, and splicing reactions were as described (Jarrell et al., supra). The E5-specific oligodexoynucleotide (5'-GTAGGATTAGATGCAGATACTAGAGC- 3') is identical to 26 nucleotides of the E5 region of the (IVS 5,6)exon(IVS 1-3) RNA. The E3-specific oligonucleotide (5'-GAGGACTTCAATAGTAGTATCCTGC-3') is homologous to 25 nt of the E3 region.

To purify E3,E5(C), described below, for the reverse transcription reaction, a standard 100-μl transcription was done, with pINV1 as a template. The (IVS 5,6)E3,E5(IVS 1-3) RNA was concentrated by ethanol precipitation and was then incubated under the $(NH_4)_2SO_4$ splicing conditions for 1 hr. The E3,E5(C) RNA was gel purified and dissolved in 30 μl of water. A 9-μl annealing reaction mixture was incubated at 65° C. for 3 min and then placed on ice. The annealing reacting mixture included 1 μl of the E3,E5(C) RNA plus 100 ng of the E3-specific oligonucleotide. As a control, an identical annealing reaction was done, except E3,E5(C) was not added. A buffer (4 μl) consisting of 0.25M Tris-HCl (pH 8.5), 0.25M KCl, 0.05M dithiothreitol, and 0.05M $MgCl_2$ was added to both annealing reaction mixtures. Deoxynucleoside triphosphates were each added to a final concentration of 5 mM, followed by 40 units of RNasin (Promgea) and 22 units of reverse transcriptase (Seikagaku America, Rockville, Md.). The final volume was adjusted to 20 μl with water. The mixture was incubated at 42° C. for 90 min.

Two polymerase chain reaction (PCR) experiments were done using as templates either 1 μl of the reverse transcription mixture that included E3,E5(C) or 1 μl of the control reverse transcription mixture, which lacked E3,E5(C). The PCRs were performed as described (14) and were continued for 25 cycles. The E3- and E5-specific oligonucleotides, 300 ng each, were used as PCR primers. DNA sequencing was done with Sequence (United States Biochemical) according to the protocol provided by the manufacturer.

Group II intron excision can occur by transesterification (splicing) or by site-specific hydrolysis (cleavage). The former reaction is stimulated by $(NH_4)_2SO_4$, the control RNAs, E5(IVS 1-3) plus (IVS5,6)E3, trans-spliced to yield spliced exon S(E5-E3) and a Y-branched intron [IVS(Y)]. Coincubation in the presence of KCl yielded free exons (E5 and E3) and a linear intron (IVS 1-3) as major products.

The (IVS 5,6)exon(IVS 1-3) precursor was also reactive. Most for the products could be identified based on their comigration with products of the control trans-reaction. In the presence of $(NH_4)_2SO_4$, the IVS(Y) and some linear intron were liberated; several novel products were also generated. Among these was an RNA (E3,E5) the expected size of the linear excised exons (591 nt). A slower migrating RNA [E3,E5(C)] was also observed. At short times of incubation (1 min) E3,E5(C) and IVS(Y) were the predominant products. In contrast, E3,E5 did not accumulate to significant levels before 60 min, indicating that it was not an early product of the reaction. Analysis of E3,E5(C) demonstrated that is was circular spliced exons. E3,E5(C) accumulated in the presence of $(NH_4)_2SO_4$ but not in the presence of KCl. This was significant, given that spliced exons (E3-E5) are not only product of cis or trans splicing that accumulates in the presence of $(NH_4)_2SO_4$ but not in the presence of KCl. Thus, it was likely that E3,E5(C) resulted from splicing rather than hydrolysis.

E3,E5(C) and E3,E5 were purified and analyzed by denaturing gel electrophoresis. During the purification process some E3,E5(C) was converted to a faster migrating species that comigrated with E3,E5. The extent of conversion of E3,E5(C) to the faster migrating species was increased by incubation with the group II intron under conditions that promote site-specific hydrolysis of the spliced exons. These observations are consistent with E3,E5(C) being a circular RNA that can be broken by hydrolysis to yield (linear) E3,E5.

To demonstrate that E3,E5(C) contains spliced exons, a cDNA copy of purified E3,E5(C) RNA was made by reverse transcription. The reverse transcription was primed with an oligonucleotide homologous to 25 nt of E3. If E3,E5(C) is accurately spliced circular exons, its length is 591 nt. Reverse transcription of this circular RNA would yield cDNAs of variable lengths; in particular, multiple rounds of complete reverse transcription of the circular template would generate cDNAs that are >591 nt long. A sample of the reverse transcription reaction mixture was used as a template in a PCR. The E3-specific oligonucleotide and an oligonucleotide homologous to 26 nt of the E5 sequence of the expected cDNA were used as primers. If E3,E5(C) is the product of a splicing reaction, it will contain both E3 and E5 sequences and will yield amplification products in this PCR reaction. Analysis of the PCR products revealed that the major amplification product is the size expected [313 base pairs (bp)] for a PCR product derived from spliced exons. This product was not seen in a control PCR reaction. Two additional PCR products of about 900 bp and 1500 bp were also observed. Amplification of longer cDNAs generated by multiple rounds of reverse transcription of the circular E3,E5(C) template would yield a set PCR products each an integral multiple of 591 bp longer than the 313 bp indicating that the 900 bp and 1500 bp observed products were likely generated in this manner.

The 313-bp PCR product was purified and cloned into a plasmid vector. The nucleotide sequence of each of four independently isolated clones was determined by the dideoxy sequencing method, using the E3-specific oligonucleotide as a primer. The sequence showed that the PCR product contained both E5 and E3 sequences that were joined by accurate splicing.

EXAMPLE 2

Mammalian Nuclear Pre-mRNA Introns Can Mediate Circularization Of Exonic Sequences The BGINV plasmid (SEQ ID No. 2) was derived from plasmid HBT7. HBT7 has the first intron of the human β-globin gene, flanked by β-globin exon 1 and 2 sequences, cloned into the psp73 vector. To construct BGINV, HBT7 was cut at the unique BbvI site in the intron and at the unique BamHI site, downstream of Exon 2. The ends were made blunt with klenow fragment. The DNA was diluted and ligase was added. A clone was isolated (BGUS) that had exon 1 and intron sequence, up to the filled BbvII site. In a separate experiment, HBT7 was cut with HindIII and BbvI, the ends were filled in, and the DNA was diluted and ligated. A clone was isolated BGDS, that had intron sequence, beginning with the filled BbvI site, followed by exon 2 sequences. BGDS was cut with XhoI and SmaI and the fragment containing the intron and exon 2 sequences was gel purified. This DNA was ligated into BGUS that had been cleaved with XhoI and PvuII, to yield BGINV. The inverse-β -globin RNA can be transcribed from this plasmid in vitro using T7 polymerase.

BGINV was cut with EcoRI and RNA was transcribed in vitro using T7 polymerase. In vitro splicing reaction were done as described in Hannon et al. (Hannon et al. (1990) Cell, 61, 1247–1255), except mammalian extract was used. The extract was prepared by the method of Dignam et al. (Dignam et al. (1983) Nucl. Acids Res. 11, 1475–1489). Splicing extract is also commercially available (Promega, cat.# E3980). Spliced products were separated by polyacrylamide gel electrophoresis and visualized by autoradiography.

The transcription reaction that generated the RNA that was used to create the circular precursor included GMP (final concentration, 0.8 mM); this was to ensure that some of the RNA transcripts initiated with GMP, instead of GTP, since a 5' phosphate is a substrate for ligase (while a 5' triphosphate is not). The transcript was purified from a polyacrylamide gel. Circular precursors were generated using a DNA oligonucleotide (5'-CGAGGCCGGTCTC-CCAATTCGAGCTCGGTAC) to bring the ends of the RNA together, followed by the addition of DNA ligase to covalently join the ends (Moore et al. (1992) Science 256, 992–997). The circular precursor was purified from a polyacrylamide gel. In vitro splicing reactions were done as described above.

The circular exon product was observed and characterized. This RNA was gel purified and a cDNA copy generated using the CIR-1 primer (5'GAGTGGACAGATC-CCCAAAGGACTC) which is specific to exon 2 sequences. The cDNA was amplified by PCR using the CIR-1 and CIR-2 (5'-GTGATGGCCTGGCTCACCTGGACAA) oligonucleotides as primers. A 145 nt product was observed. This amplification product is the expected size of a product generated from circular spliced exons.

The branched intermediate (generated by the first step of the reaction) was also observed and characterized. It was gel purified and treated with HeLa debranching enzyme (Ruskin et al. (1985) Science 229, 135–140). This treatment increased the rate of migration of the RNA through a denaturing polyacrylamide gel such that it migrated as a 553 nt RNA, consistent with the assignment of the product as the lariat intermediate.

V. Reagents For Molecular Biology

Molecular cloning of DNA currently relies heavily on restriction enzymes and DNA ligase to specifically cut and join molecules. The reverse-splicing "ribozymes" of the present invention can fulfill these two functions; they can both cut and join RNA molecules, and thus can serve as useful tools for nucleic acid manipulation. In similar fashion to the activation of an exon by addition of flanking intronic fragments through the reversal of splicing the recombinant RNA technology described herein involves attacking a target RNA molecule with an intronic molecule and, by the reversal of splicing, cleaving the target into two pieces while simultaneously joining specific intron sequences to the cleaved ends of the target molecule. The newly formed exon construction can be purified, and appropriate exons ligated to each other through trans-splicing mediated by the intronic fragments. Alternatively, these recombinant RNA molecules can be cloned into a plasmid, and fresh RNA transcripts generated from these plasmids, with these second generation transcript being used in a trans-splicing reaction. Thus, cleavage and ligation functions similar to those provided by restriction enzymes and ligase can be provided by RNA trans-splicing.

The advantages of this system are that potentially any 3–8 nt sequence can be specifically targeted, whereas restriction enzymes are much more limited, recognizing only a small subset of, for example, the 4096 possible 6 nt sequences present in DNA. Moreover, restriction enzymes typically require palindromic sequences which may introduce ambiguity into the orientation of DNA sequences inserted at a restriction endonuclease cleavage site. In addition, once an RNA is followed by, or preceded by, the correct intron sequences, any upstream molecule can be joined to any downstream molecule. In contrast, when molecular cloning is done with restriction enzymes, only molecules with compatible ends can be joined; for example, a molecule with Eco RI ends cannot be joined to a molecule with Hind III ends without first filling in the ends. Furthermore, molecules that are joined by trans-splicing are "seamless". That is, recognition sites do not have to be engineered into the target molecules in order to cleave and ligate the target molecule. Instead, the ribozyme is engineered to match the target. For instance, a library of reverse-splicing ribozymes can be generated to comprise every possible 6 nucleotide combination by manipulating intron sequences which interact with the "exon" target (e.g. the IBS1 for group II, and the IGS for group I). Thus, sequences can be precisely joined without adding, deleting or changing any nucleotides. Finally, for the autocatalytic introns, no enzymes need be added in order to catalyze the forward or reverse reactions. Instead, the RNAs are incubated together in a simple salt solution and other appropriate ions and the recombinant molecules are generated.

To illustrate, a group II intron or portion thereof can be used to specifically cut and join RNA molecules. As described above, the group II intron splicing reaction is reversible. If an intron lariat, a product of the forward reaction, is incubated with spliced exons at high RNA concentration under the reaction conditions used for the forward reaction, the intron specifically inserts into the spliced exons, thus regenerating the precursor RNA (see FIG. 1). Likewise, as illustrated in FIG. 6, a Y-branched form of the intron, generated for example by an inverse splicing reaction, can also insert into spliced exons. When a Y-branched intron, such as the illustrated (IVS5,6)2'-5'(IVS1-3) lariat, is used in a reverse-splicing reaction, the exon target is cleaved into two pieces. The upstream piece becomes joined to intron domains 1–3 and the downstream piece becomes joined to intron domains 5 and 6.

The 3–8 nucloetide EBS I site on the ribozyme is the primary determinant of the specificity of the reverse reaction for group II introns. In the reverse reaction, EBS I selects the site of integration by hydrogen bonding to it. The intron is subsequently inserted just downstream of this target sequence. By changing the nucleotide sequence of EBS 1, the ribozyme can be targeted to insert downstream of any specific 3–8 nt sequence. Moreover, the manipulation of the EBS 2:IBS 2 interactions can also influence the efficiency of splicing and provide even greater specificity to the insertion site (e.g. by expanding the recognition sequence to, for example, 10–14 nucleotides). Likewise, manipulation of the IGS, and other secondary intron:exon contacts analogous to EBS2, the specificity of a group I reverse splicing ribozyme, such as (IVS P1-P6.5)(IVS P6.5-P10) can be controlled.

Figure 17:
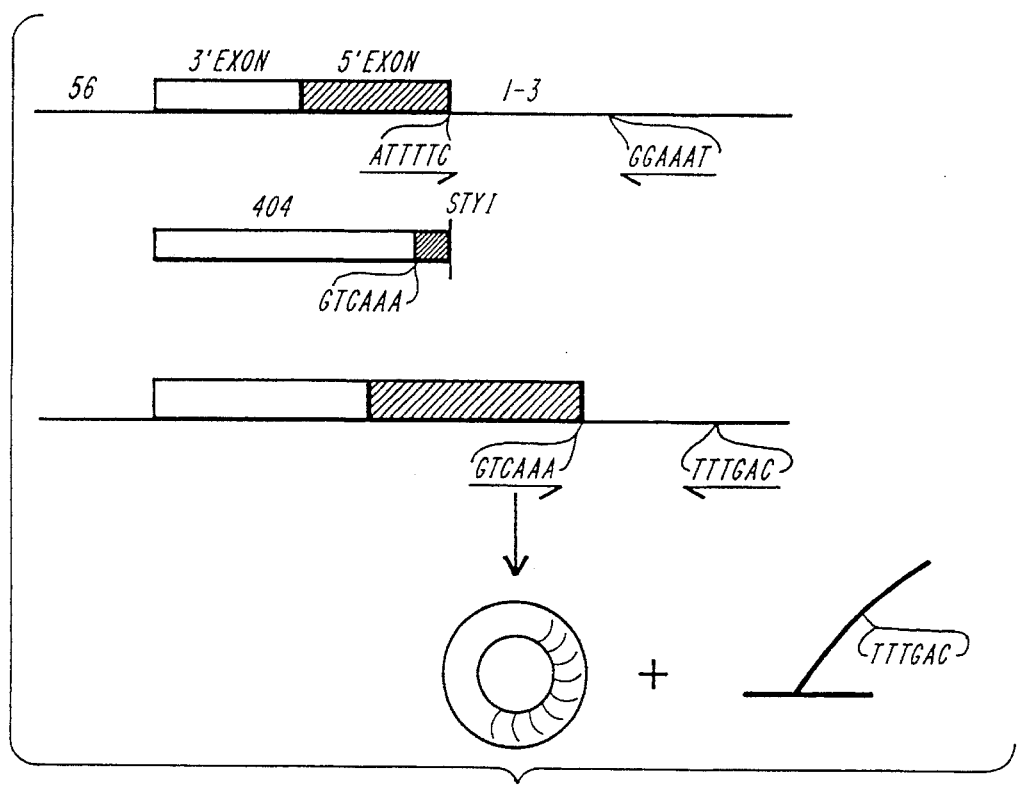
FIG. 17 is an exemplary illustration of the generation of recombinant Y-branched group II lariats.
Figure 18:
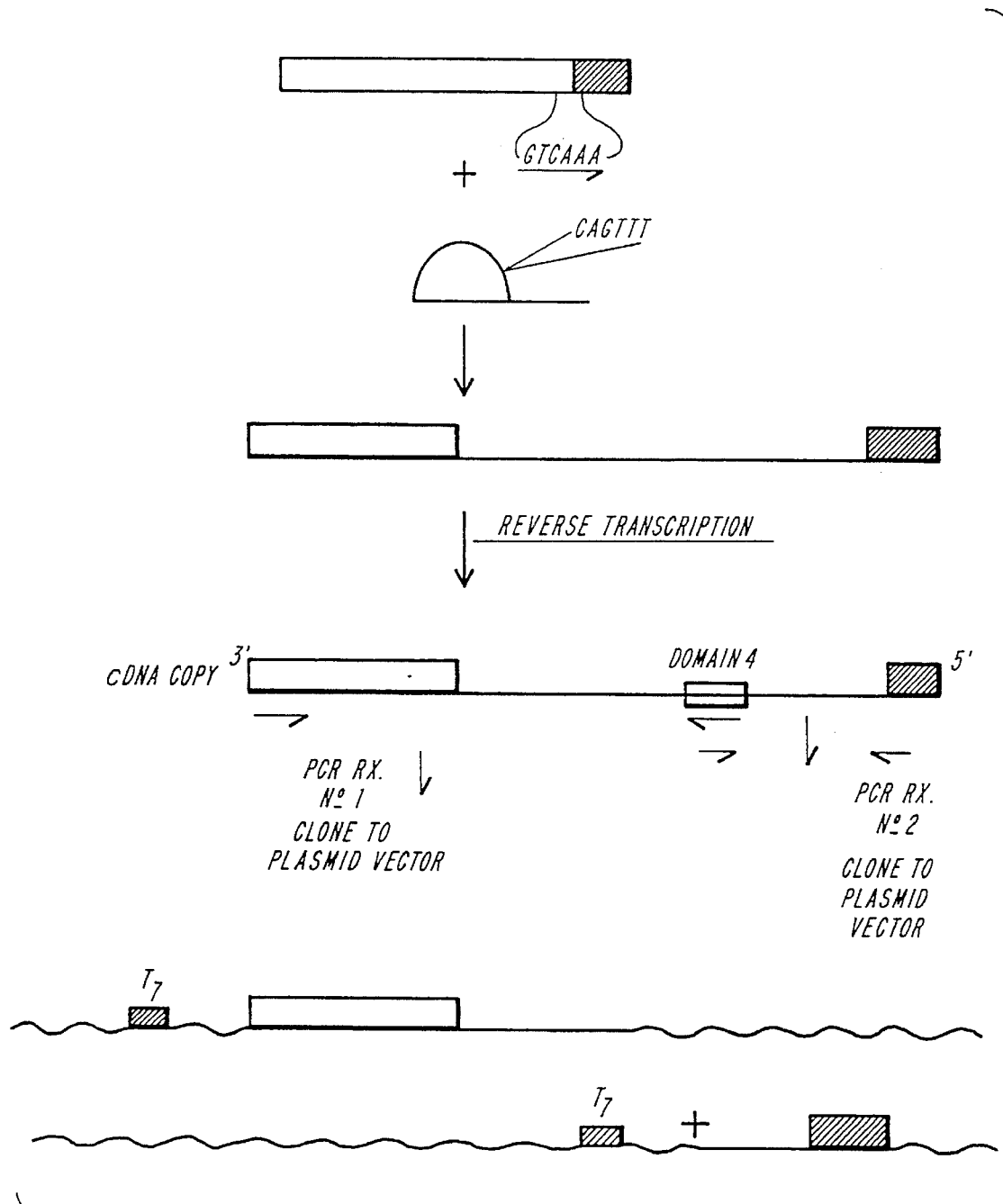
FIG. 18 depicts a further embodiment illustrating how a reverse-splicing ribozyme, such as the group II lariat IVS, can also be used to cleave and ligate target RNA molecules.

FIG. 18 depicts a further embodiment illustrating how an reverse-splicing ribozyme, such as the group II lariat IVS, can also be used to cleave and ligate target RNA molecules. The site directed mutagenesis is the same as described above (the EBS 1 and IBS 1 sequences are changed). The lariat ribozyme is generated by the forward reaction. The reverse reaction yields a single molecule with the intron specifically inserted in it. A cDNA copy is made by reverse transcriptase. Two different sets of PCR primers are used to amplify either the upstream portion of the interrupted target molecule, plus intron domains I–III -3 or to amplify domains V and VI and the downstream portion of the target molecule. Each of these amplified DNAs can be cloned into a plasmid to generate the same two constructs shown in FIG. 17.

Figure 19:
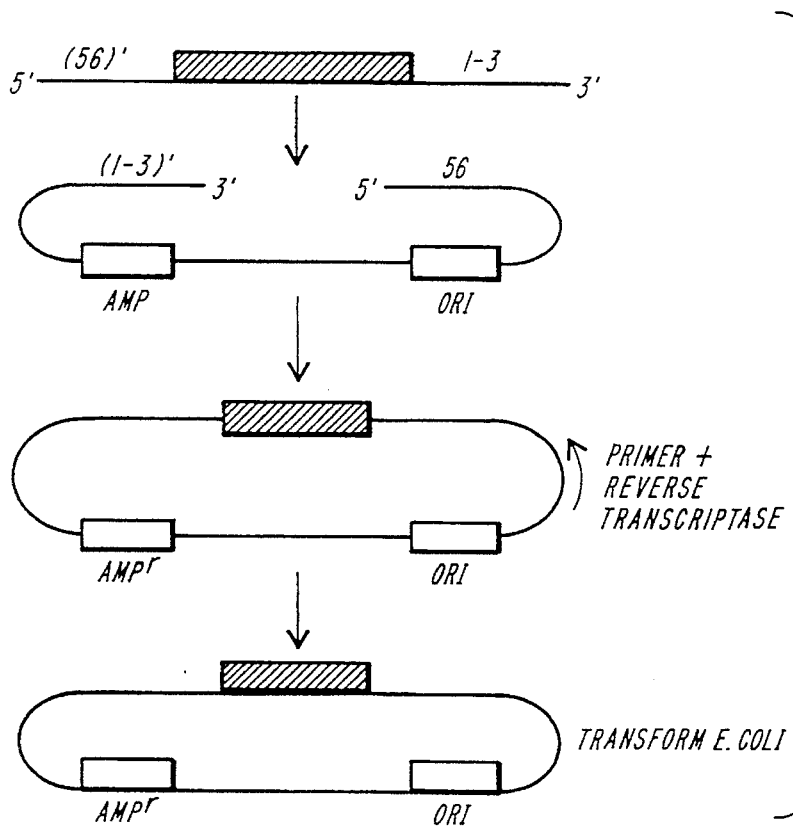
FIG. 19 depicts a method by which the present trans-splicing constructs can be used to manipulate nucleic acid sequences into a plasmid such as a cloning or expression vector.

In another illustrative embodiment, FIG. 19 depicts a method by which the present trans-splicing constructs can be used to manipulate nucleic acid sequences into a plasmid such as a cloning or expression vector. In such a scheme, the plasmid sequence is itself an exon being flanked at each end by intronic fragments capable of mediating a trans-splicing reaction. For example, as shown in FIG. 19, the plasmid can be generated as an RNA transcript comprising the backbone sequences of the plasmid, flanked at the 5' end with the group II domains V and VI, and at the 3' end with the group II and domains I–III. To generate such a transcript, a pre-plasmid can be utilized in which the 5' and 3' flanking sequences are joined with an intervening sequence including a $T_7$ RNA promoter sequences and endonuclease cleavage site. The plasmid is linearized by cleavage at the endonuclease-sensitive site, and the linearized plasmid transcribed to RNA using standard techniques.

The nucleic acid sequences to be cloned into the plasmid is generated to similarly include flanking group II intron fragments. Mixing the two transcripts under trans-splicing conditions will therefore result in ligation of the nucleic acid of interest into the plasmid, in the appropriate orientation and at the correct site. Such a method is particularly amenable to the closing of the above-described combinatorial gene libraries into replicable expression vectors. Furthermore, this trans-splicing technique of sub-cloning can be used effectively in random mutagenesis applications. For instance, the nucleic acid of interest can be first treated with actinic acid such that a discrete number of base modifications occur, and then ligated into the plasmid.

EXAMPLE 3

Use Of Group II Y-branched Lariats As Endonucleases/Ligase

FIG. 17 is an exemplary illustration of the use of these reactions to generate recombinant molecules. The last six nucleotides of the (IVS5,6)E3,E5(IVS1-3) RNA, which was generated by in vitro transcription of pINV1, are ATTTTC. The EBS 1 sequence of the flanking intron fragment is GGAAAT. As described in Example 9 below, inverse splicing of RNA transcribed from pINV1 yields a Y-branched intron with a wild-type EBS I sequence (GGAAAT). FIG. 17 shows a 404 nt RNA (TPA S,F) that includes coding information for the signal sequence and growth factor domain of the TPA cDNA clone. This transcript was generated from plasmid TPA-KS+ that had been cut with Sty I. The goal was to attack TPA S,F with a Y-branched ribozyme such that the ribozyme inserted downstream of the GTCAAA sequence that is present at the end of the growth factor domain. In order to use pINV1 to generate a Y-branched ribozyme capable of attacking the TPA S,F RNA, the EBS I and IBS I sequences of pINVI were changed by site directed mutagenesis. The IBS 1 sequence was changed to GTCAAA (that is, to the same sequence present in the TPA transcript that is to be attacked), and the EBS 1 sequence was changed to TTTGAC in order that it be complementary to the mutated IBS 1 sequence. RNA was transcribed in vitro from this altered plasmid (termed here GrII-SIG) and incubated under splicing conditions to yield the excised Y-branched molecule (SIG-Y). This Y-branched intron is identical to that derived from (IVS5,6)E5,E3,(IVS1-3) in Example 9, except the EBS 1 sequence is TTTGAC. This Y-branched ribozyme was tested for its ability to insert specifically into TAP S,F RNA. As diagrammed in FIG. 17, this RNA was incubated with the 404 nt target RNA under splicing conditions. Specific reversal generates a 1047 nt product that consists of the first 332 nt of the TPA-KS+ transcript ligated to intron domains 1–3. This 1047 nt product was gel purified and a cDNA copy was made by reverse transcription. The cDNA was amplified by PCR and cloned into a vector to yield plasmid SIG(IVS1-3). The smaller, 108 nt, product consists of intron domains 5 and 6 ligated to 72 nt of TPA S,F. A cDNA copy of the smaller product can likewise be made by reverse transcription, amplified by PCR, and the amplified product cloned into a vector to yield plasmid (IVS5,6)StyI.

It is clear from this example that potentially any 4–8 nt RNA sequence can be attacked specifically by a Y-branch ribozyme that has been engineered to have the appropriate EBS 1 sequence. The target molecule will be split into two pieces. Intron domains 1–3 will be ligated to the upstream piece, while domains 5 and 6 will be ligated to the downstream piece. Following reverse transcription and PCR, these recombinant molecules can each be cloned into a plasmid vector downstream, for example, of the T7 promoter. Synthesis of RNA from the plasmid will yield transcripts capable of trans-splicing. Thus, the original 404 nt target RNA could be regenerated by trans splicing. Moreover, it is also true that trans-splicing can be used to join the TPA sequences of SIG(IVS1-3) to any other RNA that has intron domains 5 and 6 upstream of it. The recombinant RNA molecule generated by such a trans-splicing reaction could be copied into cDNA, amplified by PCR and cloned into a plasmid vector.

VI. Generating Novel Genes and Gene Products

A major goal of the present combinatorial method is to increase the number of novel genes and gene products that can be created by exon shuffling in a reasonable period of time. As described herein, the exon portion of the present splicing constructs can encode a polypeptide derived from a naturally occurring protein, or can be artificial in sequence. The exon portion can also be a nucleic acid sequences of other function, such as a sequence derived from a ribozyme. By accelerated molecular evolution through shuffling of such exons, a far greater population of novel gene products can be generated and screened in a meaningful period of time.

In our embodiment, the field of application of the present combinatorial method is in the generation of novel enzymatic activities, such as proteolytic enzymes. For example, combinatorial trans-splicing can be used to rapidly generate a library of potential thrombolytic agents by randomly shuffling the domains of several known blood serum proteins. In another embodiment, the trans-splicing technique can be used to generate a library of antibodies from which antibodies of particular affinity for a given antigen can be isolated. As described below, such an application can also be especially useful in grafting CDRs from one variable region to another, as required in the "humanization" of non-human antibodies. Similarly, the present technology can be extended to the immunoglobulin-super family, including the T-cell receptor, etc., to generate novel immulogically active proteins.

In another illustrative embodiment, the present trans-splicing method can be used to generate novel signal-transduction proteins which can subsequently be used to generate cells which have altered responses to certain biological ligands or stimuli. For instance, protein tyrosine kinases play an important role in the control of cell growth and differentiation. Ligand binding to the extracellular domain of receptor tyrosine kinases often provides an important regulatory step which determines the selectivity of intracellular signaling pathways. Combinatorial exon splicing can be used to shuffle, for example, intracellular domains of receptor molecules or signal transduction proteins, including SH2 domains, SH3 domains, kinase domains, phosphatase domains, and phospholipase domains. In another embodiment, variant of SH2 and SH3 domains are randomly shuffled with domains engineered as either protein kinase or phosphatase inhibitors and the combinatorial polypeptide library screened for the ability to block the function of, for example, the action of oncogenic proteins such as sic or ras.

Many techniques are known in the art for screening gene products of combinatorial libraries made by point mutations, and for screening cDNA libraries for gene products having a certain property. Such techniques will be generally applicable to screening the gene libraries generated by the present exon-shuffling methodology. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose produced was detected. For instance, in the case of shuffling intracellular domains, phenstypic changes can be detected and used to isolate cells expressing a combinatorially-derived gene product conferring the new phenotype. Likewise, interaction trap assays can be used in vivo to screen large polypeptide libraries for proteins able to bind a "bait" protein, or alternatively, to inhibit binding of two proteins.

For ribozymes, one illustrative embodiment comprises screening a ribozyme library for the ability of molecules to cleave an mRNA molecule and disrupt expression of a protein in such a manner as to confer some phenotypic change to the cell. Similarly, to assay the ability of novel autocatalytic introns to mediate splicing (e.g. see the group II domain shuffling described above) the ability of a combinatorial intron to mediate splicing between two exons can be detected by the ability to score for the protein product of the two exons when accurately spliced.

In yet another screening assay, the gene product, especially if its a polypeptide, is displayed on the surface of a cell or viral particle, and the ability of particular cells or viral particles to bind another molecule via this gene product is detected in a "panning assay". For example, the gene library can be cloned into the gene for a surface membrane protein of a bacterial cell, and the resulting fusion protein detected on the surface of the bacteria (Ladner et al., WO 88/06630; Fuchs et al. (1991) Bio/Technology 9:1370–1371; and Goward et al. (1992) TIBS 18:136–140). In another embodiment, gene library is expressed as fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, large number of phage can be screened at one time. Second, since each infectious phage encodes the exon-shuffled gene product on its surface, if a particular phage is recovered from an affinity matrix in low yield, the phage can be amplified by another round of infection. The group of almost identical E. coli filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) J. Biol. Chem. 267:16007–16010; Griffths et al. (1993) EMBO J 12:725–734; Clackson et al. (1991) Nature 352:624–628; and Barbas et al. (1992) PNAS 89:4457–4461).

A. Antibody Repertoires

Mouse monoclonal antibodies are readily generated by the fusion of antibody-producing B lymphocytes with myeloma cells. However, for therapeutic applications, human monoclonal antibodies are preferred. Despite extensive efforts, including production of heterohybridomas, Epstein-Barr virus immortalization of human B cells, and "humanization" of mouse antibodies, no general method comparable to the Kohler-Milstein approach has emerged for the generation of human monoclonal antibodies.

Recently, however, techniques have been developed for the generation of antibody libraries in *E. coli* capable of expressing the antigen binding portions of immunoglobulin heavy and light chains. For example, recombinant antibodies have been generated in the form of fusion proteins containing membrane proteins such as peptidoglycan-associated lipoprotein (PAL), as well as fusion proteins with the capsular proteins of viral particles, or simply as secreted proteins which are able to cross the bacterial membrane after the addition of a bacterial leader sequence at their N-termini. (See, for example, Fuchs et al. (1991) Bio/Technology 9:1370–1372; Bettes et al. (1988) Science 240:1041–1043; Skerra et al. (1988) Science 240:1038–1041; Hay et al. (1992) Hum. Antibod. Hybridomas 3:81–85; and Barbas et al. International Publication No. WO92/18019).

The display of antibody fragments on the surface of filamentous phage that encode the antibody gene, and the selection of phage binding to a particular antigen, offer a powerful means of generating specific antibodies in vitro. Typically, phage antibodies (phAbs) have been generated and expressed in bacteria by cloning repertoires of rearranged heavy and light chain V-genes into filamentous bacteriophage. Antibodies of a particular specificity can be selected from the phAb library by panning with antigen. The present intron-mediated combinatorial approach can be applied advantageously to the production of recombinant antibodies by providing antibody libraries not readily accessible by any prior technique. For instance, in contrast to merely sampling combinations of $V_H$ and $V_L$ chains, the present method allows the complementarity-determining regions (CDRs) and framework regions (FRs) themselves to be randomly shuffled in order to create novel $V_H$ and $V_L$ regions which were not represented in the originally cloned rearranged V-genes.

Figure 20A:
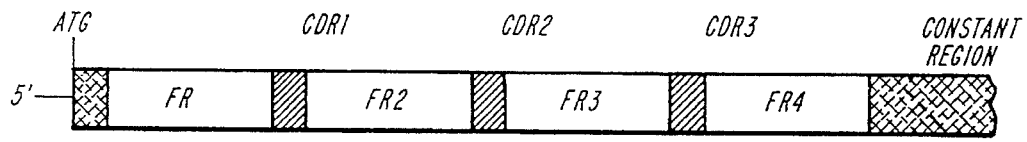
FIG. 20A is an illustration of the composite protein structure of the variable region of both heavy and light chains of an antibody.

Antibody variable domains consist of a β-sheet framework with three loops of hypervariable sequences (e.g. the CDRs) (see FIG. 20A), and the antigen binding site is shaped by loops from both heavy ($V_H$) and light ($V_L$) domains. The loops create antigen binding sites of a variety of shapes, ranging from flat surfaces to pockets. For human $V_H$ domains, the sequence diversity of the first two CDRs are encoded by a repertoire of about 50 germline $V_H$ segments (Tomlinson et al. (1992) J. Mol. Biol. 227:). The third CDR is generated from the combination of these segments with about 30 D and six J segments (Ichihara et al. (1988) EMBO J 7: 4141–4150). The lengths of the first two CDRs are restricted, with the length being 6 amino acid residues for CDR1, 17 residues, and for CDR2. However, the length of CDR3 can differ significantly, with lengths ranging from 4 to 25 residues.

For human light chain variable domains, the sequence diversity of the first two CDRs and part of CDR3 are encoded by a repertoire of about 50 human $V_\kappa$ segments (Meindl et al. (1990) Eur. J. Immunol. 20: 1855–1863) and > 10 $V_\lambda$ segments (Chuchana et al. (1990) Eur. J. Immunol. 20: 1317–1325; and Combriato et al. (1991) Eur. J. Immunol. 21: 1513–1522). The lengths of the CDRs are as follows, CDR1=11–14 residues; CDR2=8 residues; and CDR3 ranges from 6 to 10 residues for $V_\kappa$ genes and 9 to 13 for $V_\lambda$ genes.

The present invention contemplates combinatorial methods for generating diverse antibody libraries, as well as reagents and kits for carrying out such methods. In one embodiment, the present combinatorial approach can be used to recombine both the framework regions and CDRs to generate a library of novel heavy and light chains. In another embodiment, trans-splicing can be used to shuffle only the framework regions which flank specific CDR sequences. While both schemes can be used to generate antibodies directed to a certain antigen, the later strategy is particularly amenable to being used for "humanizing" non-human monoclonal antibodies.

Figure 20B:
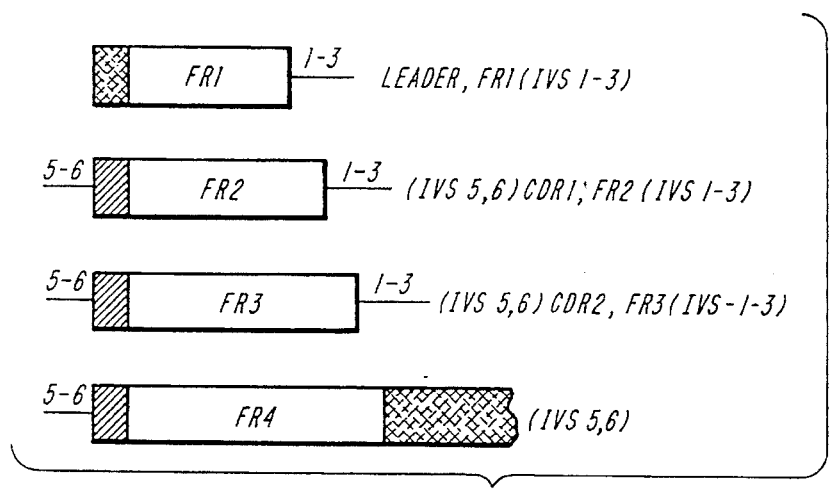
FIGS. 20B–C illustrate possible combinatorial constructs produced using antibody framework regions (FRs) and complementarity determining regions (CDRs).

The combinatorial units useful for generating diverse antibody repertoires by the present trans-splicing methods comprise exon constructs corresponding to fragments of various immunoglobulin variable regions flanked by intronic sequences that can drive their ligation. As illustrated in FIGS. 20B and 18C, the "exonic" sequences of the combinatorial units can be selected to encode essentially just a framework region or CDR; or can be generated to correspond to larger fragments which may include both CDR and FR sequences. The combinatorial units can be made by standard cloning techniques that manipulate DNA sequences into vectors which provide appropriate flanking intron fragments upon transcription. Alternatively, the combinatorial units can be generated using reverse-splicing, as described above, to specifically add intronic sequences to fragments of antibody transcripts.

Methods are generally known for directly obtaining the DNA sequence of the variable regions of any immunoglobulin chain by using a mixture of oligomer primers and PCR. For instance, mixed oligonucleotide primers corresponding to the 5' leader (signal peptide) sequences and/or FR1 sequences and a conserved 3' constant region primer have been used for PCR amplification of the heavy and light chain variable regions from a number of human antibodies directed to, for example, epitopes on HIV-I (gp 120, gp 42), digoxin, tetanus, immunoglobulins (rheumatoid factor), and MHC class I and II proteins (Larrick et al. (1991) Methods: Companion to Methods in Enzymology 2:106–110). A similar strategy has also been used to amplify mouse heavy and light chain variable regions from murine antibodies, such as antibodies raised against human T cell antigens (CD3, CD6), carcino embryonic antigen, and fibrin (Larrick et al. (1991) Bio Techniques 11: 152–156).

In the present invention, RNA is isolated from mature B cells of, for example, peripheral blood cells, bone marrow, or spleen preparations, using standard protocols. First-strand cDNA is synthesized using primers specific for the constant region of the heavy chain(s) and each of the κ and λ light chains. Using variable region PCR primers, such as those shown in Table I below, the variable regions of both heavy and light chains are amplified (preferably in separate reactions) and ligated into appropriate expression vectors. The resulting libraries of vectors (e.g. one for each of the heavy and light chains) contain a variegated population of variable regions that can be transcribed to generate mRNA enriched for $V_H$ and $V_L$ transcripts. Using the reversal of splicing reaction, group I or group II introns can be used which are designed to insert immediately downstream of specific nucleotide sites corresponding to the last (carboxy terminal) 2–3 amino acid residues of each framework region. For example, as depicted in FIG. 20B, a set of group II Y-branched lariats can be utilized to specifically insert flanking group II intron fragments between each CDR sequence and the FR sequence immediately upstream. The exon binding sequence (EBS1, and in some instances EBS2) of each Y-branched lariat is manipulated to create a panel of Y lariats based on sequence analysis of known framework regions (FR1-4). The intronic addition can be carried out simultaneously for all three FR/CDR boundaries, or at fewer than all three boundaries. For instance, the RNA transcripts can be incubated with Y lariats which drive insertion at only the FR1/CDR1 and FR2/CDR2 boundaries. The resulting intron-containing fragments can be reverse transcribed using a domain VI primer, and the cDNA amplified using PCR primers complementary to a portion of domain VI, a portion of domain I, and the leader sequence. Thus, the Leader, FR1(IVS 1-3) and (IVS 5,6)CDR1,FR2(IVS 1-3) constructs will be generated. Likewise, the RNA transcript can instead be incubated under reverse-splicing conditions with Y-branched lariats which are directed to insertion at the FR2/CDR2 and FR3/CDR3 boundaries, resulting in the (IVS 5,6)CDR2,FR3(IVS 1-3) and (IVS 5,6)CDR3,FR4 combinatorial units, which can then be isolated by reverse transcription and PCR using primers to sequences in domain I, domain VI, and the constant region.

TABLE I

Human Immunoglobulin Variable Region PCR Primers

5' End Sense
Human heavy chains
    Group A
        5'-GGGAATTCATGGACTGGACCTGGAGG(AG)TC(CT)-
            TCT(GT)C-3'
    Group B
        5'-GGGAATTCATGGAG(CT)TTGGGCTGA(CG)CTGG(CG)-
            TTTT-3'
    Group C
        5'-GGGAATTCATG(AG)A(AC)(AC)(AT)ACT(GT)TG(GT)-
            (AT)(CG)C(AT)(CT)(CG)CT(CT)CTG-3'
Human κ light chain
        5'-GGGAATTCATGGACATG(AG)(AG)(AG)(AGT)(CT)CC-
            (ACT)(ACG)G(CT)GT)CA(CG)CTT-3'
Human λ light chain
        5'-GGGAATTCATG(AG)CCTG(CG)(AT)C(CT)CCTCTC(CT)-
            T(CT)CT(CG)(AT)(CT)C-3'
3' End sense constant region
Human IgM heavy chain
    5'-CCAAGCTTAGACGAGGGGGAAAAGGGTT-3'
Human IgG1 heavy chain
    5'-CCAAGCTTGGAGGAGGGTGCCAGGGGG-3'
Human λ light chain
    5'-CCAAGCTTGAAGCTCCTCAGAGGAGGG-3'
Human κ light chain
    5'-CCAAGCTTTCATCAGATGGCGGGAAGAT-3'

Murine Immunoglobulin Variable Region PCR Primers

5' End sense
Leader (signal peptide) region (amino acids −20 to −13)
    Group A
        5'-GGGGAATTCATG(GA)A(GC)TT(GC)(TG)GG(TC)T(AC)-
            A(AG)CT(GT)G(GA)TT-3'
    Group B
        5'-GGGGAATTCATG(GA)AATG(GC)A(GC)CTGGGT(CT)-
            (TA)T(TC)CTCT-3'
Framework 1 region (amino acids 1 to 8)
        5'-GGGGAATTC(CG)AGGTG(CA)AGCTC(CG)(AT)(AG)(CG)-
            A(AG)(CT)C(CG)GGG-3'
3' End sense constant region
Mouse γ constant region (amino acids 121 to 131)
    5'-GGAAGCTTA(TC)CTCCACACACAGG(AG)(AG)CCAGTG-
        GATAGAC-3'
Mouse κ light chain (amino acids 116 to 122)
    5'-GGAAGCTTACTGGATGGTGGGAAGATGGA-3'

Bases in parentheses represent substitutions at a given residue. EcoRI and HindIII sites are underlined.

The Leader, FR1 (IVS 1-3) transcripts can be linked to an insoluble resin by standard techniques, and each set of combinatorial units (CDR1/FR2, CDR2/FR3, CDR3/FR4) can be sequentially added to the resin-bound nucleic acid by incubation under trans-splicing conditions, with unbound reactants washed away between each round of addition. After addition of the (IVS 5,6)CDR3,FR4 units to the resin bound molecules, the resulting trans-spliced molecule can be released from the resin, reverse-transcribed and PCR amplified using primers for the leader sequence and constant region, and subsequently cloned into an appropriate vector for generating a screenable population of antibody molecules.

Taking the dissection of the variable regions one step further, a set of exon libraries can be generated for ordered combinatorial ligation much the same as above, except that each combinatorial unit is flanked at its 5' end with an intron fragment that is unable to drive a trans-splicing reaction with the intron fragment at its 3' end. As described above (section II) with regard to ordered gene assembly, each combinatorial unit is effectively protected from addition by another unit having identical flanking intron fragments. The 5' and 3' flanking intronic sequences can be of the same group, but from divergent enough classes (i.e. group IIA versus group IIB) or divided in such a way that intermolecular complementation and assembly of an active splicing complex cannot occur; or the intron fragments can simply be from different groups (e.g. group I versus group II).

Figure 20C:
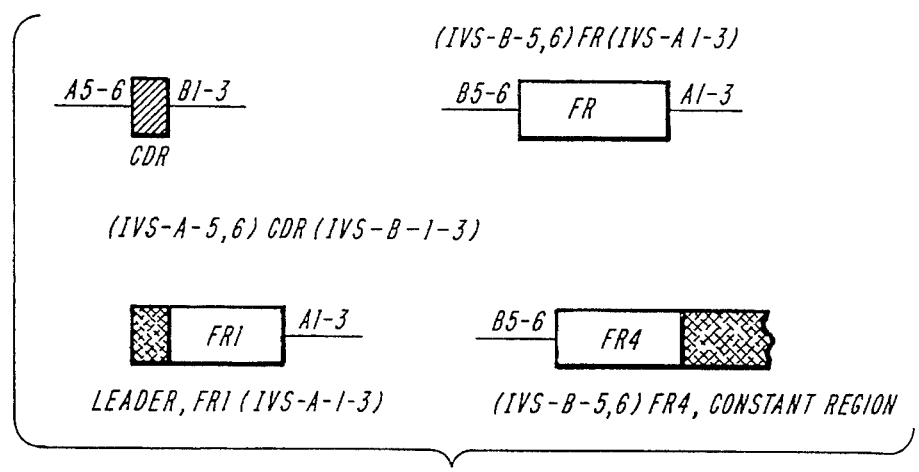

As illustrated in FIG. 20C, the combinatorial units of FIG. 20B can be generated with Y lariats derived from group IIA intron fragments (hence the designation "IVS-A-5, 6"). Each CDR is then split from the downstream framework region using a Y-branched lariat derived from a group IIB intron having a divergent enough domain V that neither combination of (IVS-A-5,6) and (IVS-B-1-3) or (IVS-B-5,6) and (IVS-A-1-3) results in a functional splicing complex. In order to avoid the need to determine the sequence of each of the cloned CDRs, the exon-binding sites of the IIB intron lariats can be constructed to match the much less variable nucleotide sequences corresponding to the first (amino terminal) 2–3 a.a. residues of each of the framework regions (FR2-4). The resulting constructs include internal exon units of the general formula (IVS-A-5,6)CDR(IVS-B-1-3) and (IVS-B-5,6)FR (IVS-A-1-3), with each CDR containing an extra 2–3 a.a. residues from the FR which previously flanked it. Thus, by sequentially adding each pool of combinatorial units to the resin-immobilized FR1, an ordered combinatorial ligation of variegated populations of CDRs and FRs can be carried out to produce a library of variable region genes in which both the CDRs and FRs have been independently randomized.

Furthermore, CDR combinatorial units can be generated which are completely random in sequence, rather than cloned from any antibody source. For instance, a plasmid similar to pINV1 (described herein) can be used to create a set of random CDR sequences of a given length and which are flanked by appropriate intronic fragments. In an illustrative embodiment, the plasmid includes restriction endonuclease sites in each of the 5' and 3' flanking intron sequences such that oligonucleotides having the CDR coding sequence can be cloned into the plasmid. For example, a degenerate oligonucleotide can be synthesized for CDR1 which encodes all possible amino acid combinations for the 6 a.a. sequence. The nucleotide sequences which flank the CDR-encoding portion of the oligonucleotide comprise the flanking intron sequences necessary to allow ligation of the degenerate oligonucleotide into the plasmid and reconstitute a construct which would produce a spliceable transcript. To avoid creation of stop codons which can result when codons are randomly synthesized using nucleotide monomers, "dirty bottle" synthesis can instead be carried out using a set of nucleotide trimers which encode all 20 amino acids.

With slight modification, the present ordered combinatorial ligation can be used to efficiently humanize monoclonal antibodies of non-human origin. The CDRs from the monoclonal antibody can be recombined with human framework region libraries (e.g. an FR1 library, an FR2 library, etc.) to produce a combinatorial population of variable regions in which the CDR sequences are held constant, but each of the framework regions have been randomized. The variable regions can be subsequently fused with sequences corresponding to the appropriate human constant regions, and the antibodies resulting from heavy and light chain association can be screened for antigen binding using standard panning assays such as phage display. In contrast to contemporary humanization schemes which require the practitioner to prejudicially choose a particular human scaffold into which the CDRs are grafted, the present technique provides a greater flexibility in choosing appropriate human framework regions which do not adversely affect antigen binding by the resultant chimeric antibody.

To illustrate, the variable regions of both the heavy and light chains of a mouse monoclonal antibody can be cloned using primers as described above. The sequence of each CDR can be obtained by standard techniques. The CDRs can be cloned into vectors which provide appropriate flanking intronic sequences, or alternatively, isolated by reverse-splicing with Y-branched lariats designed to insert precisely at each FR/CDR and CDR/FR boundary. As described above, the particular intronic fragments provided with each murine CDR and each human FR construct can be selected to disfavor multiple ligations at each step of addition to a resin bound nucleic acid. The library of human heavy chain leader, FR1 (IVS-A- 1-3) constructs can be immobilized on a resin, and in a first round of ligation, the heavy chain murine (IVS-A-5,6)CDR1(IVS-B-1-3) construct is added under trans-splicing conditions. Un-ligated combinatorial units are washed away, and the library of human heavy chain (IVS-B- 5,6)FR2(IVS-A-1-3) units are admixed and trans-spliced to the resin-bound nucleic acids terminating with the murine CDR construct. This process is carried out for the remaining murine CDR and human FR units of the heavy chain, and a similar process is used to construct combinatorial light chain chimeras as well. The resulting chimeric heavy and light chains can be cloned into a phage display library, and the phAbs screened in a panning assay to isolate humanized antibodies (and their genes) which bind the antigen of interest.

B. Combinatorial Enzyme Libraries

Plasminogen activators (PAs) are a class of serine proteases that convert the proenzyme plasminogen into plasmin, which then degrades the fibrin network of blood clots. The plasminogen activators have been classified into two immunologically unrelated groups, the urokinase-type PAs (u-PA) and the tissue-type PA (tPA), with the later activator being the physiological vascular activator. These proteins, as well as other proteases of the fibrinolytic pathway, are composed of multiple structural domains which appear to have evolved by genetic assembly of individual subunits with specific structural and/or functional properties. For instance, the amino terminal region of tPA is composed of multiple structural/functional domains found in other plasma proteins, including a "finger-like domain" homologous to the finger domains of fibronectin, an "epidermal growth factor domain" homologous to human EGF, and two disulfide-bonded triple loop structures, commonly referred to as "kringle domains", homologous to the kringle regions in plasminogen. The region comprising residues 276–527 (the "catalytic domain" is homologous to that of other serine proteases and contains the catalytic triad. In addition, the gene for tPA encodes a signal secretion peptide which directs secretion of the protein into the extracellular environment, as well as a pro-sequence which is cleaved from the inactive form of the protease (the "plasminogen") to active tPA during the fibrinolytic cascade.

These distinct domains in tPA are involved in several functions of the enzyme, including its binding to fibrin, stimulation of plasminogen activation by fibrin, and rapid in vivo clearance. Approaches used to characterize the functional contribution of these structural domains include isolation of independent structural domains as well as the production of variant proteins which lack one or more domains. For example, the fibrin selectivity of tPA is found to be mediated by its affinity for fibrin conferred by the finger-like domain and by at least one of the kringle domains.

The present combinatorial method can be used to generate novel plasminogen activators having superior thrombolytic properties, by generating a library of proteins by RNA-splicing mediated shuffling of the domains of plasma proteins. As described below, one mode of generating the combinatorial library comprises the random trans-splicing of a mixture of exons corresponding to each of the domains of the mature tPA protein. Briefly, a cDNA clone of tPA was obtained and, through the use of specific PCR amplimers, each of the 5 protein domains was amplified and isolated. Each of these amplified domains was then separately cloned into a plasmid as an exon module such that the 5' end of the exon is preceded by group II domains V–VI, and the 3' end of the exon is followed by group II domains I–III. In addition, the IBS 1 site of each of the exon was mutated in order to facilitate base pairing with the EBS 1 sequence of the 3' flanking intron fragment. Transcription of the resulting construct thus produces RNA transcripts of the general formula (IVS 5,6)-Exon-(IVS 1-3). Mixture of these transcripts under trans-splicing conditions can result in random ligation of the exons to one and other and assembly of the combinatorial gene library which can subsequently be screened for fibrinolytic activity.

Moreover, combinatorial units can be generated from other proteins, including proteins having no catalytic role in blood clotting or fibrinolysis. For example, a library of catalytic domains can be generated from other thrombolytic proteases, blood clotting factors, and other proteases having peptidic activity similar to the typsin-like activity of tPA. Likewise, libraries of splicing constructs can be derived from EGF-like domains, finger-like domains, kringle domains, and Calcium-binding domains from a vast array of proteins which contain such moieties.

EXAMPLE 4

Construction Of Plasmid TPA-KS$^+$

The cDNA clone of the human tissue plasminogen activator (tPA) gene (pETPFR) was obtained from the ATCC collection (ATCC 40403; and U.S. Pat. No. 4,766,075). The entire cDNA clone was amplified by PCR using primers 5'-ACGATGCATGCTGGAGA GAAAACCTCTGCG and 5'-ACGATGCATTCTGTAGAGAAGCACTGCGCC. TPA sequences from 70 base pairs (bp) upstream of the translation initiation site (AUG) to 88 bp downstream of the translation termination site (TGA) were amplified (SEQ. ID No. 3). In addition, the primers added Nsi I sites to both ends of the amplified DNA. The amplified DNA was cut with Nsi I and ligated into the KS$^+$ vector that had been cut with Pst I. A clone TPA-KS$^+$, was isolated with the insert oriented such that in vitro transcription with $T_7$ RNA polymerase yields an RNA that is the same polarity as the tPA mRNA.

EXAMPLE 5

Construction Of Plasmid INV-KX

Two unique restriction sites were added to the pINV1 plasmid (SEQ ID No. 1) by site directed mutagenesis, to facilitate insertion of portions of the tPA clone. A Kpn I site (GGTACC) was inserted at precisely the boundary between the end of the intron and the beginning of E3. An Xho I site was added to E5 by changing the sequence GTGGGA to a Xho I site (CTCGAG). Thus, the last seven bp of the exon were unchanged, but the six preceding base pairs were changed to create a Xho I site. The resulting plasmid is termed here INV-KX.

EXAMPLE 6

Construction Of Plasmid INV-K(K1)X

The region of the TPA cDNA clone that encodes the kringle-1 (K1) domain was amplified by PCR. The primers added a Kpn I site at the upstream end of the domain and a Xho I site to the downstream end. The amplified DNA was cut with Kpn I and Xho I and ligated into INV-KX such that the K1 sequences replaced the E3,E5 exon sequences.

EXAMPLE 7

Construction Of Plasmid (IVS 5,6)K1(IVS1-3)

Oligonucleotide splints were used in a site-directed mutagenesis experiment to change the sequences at the boundaries of the INV-KX derived introns and the K1 exon. The sequences were changed such that the intron sequences of domain 6 are directly following by kringle domain sequences ACC AGG GCC and kringle sequences TCT GAG GGA precede the intron sequences of domain 1. In addition, the sequence of the EBS 1 sequence in domain 1 was changes to TCCCTCA (this sequence is homologous to the last 7 nt of K1 (TGAGGGA). Thus, the resulting transcript, (IVS5,6)K1(IVS1-3), contains complementary IBS1 and EBS1 sequences.

EXAMPLE 8

Construction Of Plasmid GrII-Sig

Two oligonucleotide primers were used to change the IBS 1 sequence of pINV1 to TGTCAAA and the EBS 1 sequence to TTTGACA. Thus, the last seven nucleotides of E5 were changes to the sequence of the last 7 nucleotides of TPA fibronectin finger like domain and the EBS 1 sequence was made complementary. The resulting plasmid is termed here GrII-Sig.

EXAMPLE 9

Construction Of Plasmid SIG(IVS1-3)

The plasmid SIG(IVS1-3) contains the first two protein domains of TPA (the signal sequence and the finger domain) followed by group II intron domains 1–3. It was made by the reversal of splicing. Plasmid GrII-Sig (Example 8) was linearized with Hind III and RNA made using $T_7$ polymerase in vitro. The RNA was incubated under self splicing conditions for two hours and the products fractionated on an acrylamide gel. The Sig(Y) molecule (a Y-branched lariat intron comprising domains 5 and 6 joined to domains 1 through 3 by a 2'-5' phosphodiester bond) was gel purified. This molecule was the "enzyme" used for the reverse-splicing reaction. The substrate was made by cutting TPA-KS$^+$ DNA (Example 4) with Sty I, which cuts 17 bp downstream of the end of the finger domain. A 404 nt RNA was made using $T_7$ polymerase. The enzyme and substrate were mixed and incubated under splicing conditions for two hours. By the reversal of splicing, the Sig(Y) RNA attacked the substrate to yield the signal plus finger region followed by intron domains 1 through 3. A cDNA copy of the molecule was made using reverse transcriptase and amplified by PCR. It was cloned into the PBS vector in the $T_7$ orientation.

EXAMPLE 10

Construction Of Other Shuffling Clones

Clones with each of the other three protein domains (growth factor (GF) domain, kringle 2 (K2) domain and catalytic (cat) domain), flanked by group II intron sequences, can also be made by either standard cloning methods or by the reversal of splicing method, as described above, to yield constructs corresponding to (IVS5,6)FG(IVS1-3), (IVS5,6)K2(IVS1-3), and (IVS5,6)cat or (IVS5,6)cat(IVS1-3).

EXAMPLE 11

Generation Of Library

RNA transcripts are made for each of the tPA combinatorial units, SIG(IVS1-3), (IVS5,6)K1(IVS1-3), (IVS5,6)K2(IVS1-3), (IVS5,6)GF(IVS1-3), and (IVS5,6)cat-(IVS1-3). The transcripts are mixed and incubated under trans-splicing conditions. The resulting combinatorial RNA molecules can be reverse-transcribed to cDNA using primers complementary to sequences in the intron domains I–III, and the cDNA amplified by PCR using a similar primer and a primer to the tPA signal sequence. The amplified cDNAs can subsequently be cloned into suitable expressions vectors to generate an expressions library, and the library screened for fibrinolytic activity by standard assays.

All of the above-cited references and publications are hereby incorporated by reference.

Equivalents

Those skilled in the art will recognize, or be able to ascertain using no more than routine experimentation, numerous equivalents to the specific methods and reagents described herein. Such equivalents are considered to be within the scope of this invention and are covered by the following claims.

---

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 4539 base pairs
        ( B ) TYPE: nucleic acid
        ( C ) STRANDEDNESS: double
        ( D ) TOPOLOGY: both ( i i ) MOLECULE TYPE: other nucleic acid ( i x ) FEATURE:
        ( A ) NAME/KEY: misc_feature
        ( B ) LOCATION: 969..1259
        ( D ) OTHER INFORMATION: /product="E3 exon"

( i x ) FEATURE:
        ( A ) NAME/KEY: misc_feature
        ( B ) LOCATION: 1290..1559
        ( D ) OTHER INFORMATION: /product="E5 exon"

( x i ) SEQUENCE DESCRIPTION: SEQ ID NO:1:

```
TCGCGCGTTT  CGGTGATGAC  GGTGAAAACC  TCTGACACAT  GCAGCTCCCG  GAGACGGTCA      60
CAGCTTGTCT  GTAAGCGGAT  GCCGGGAGCA  GACAAGCCCG  TCAGGGCGCG  TCAGCGGGTG     120
TTGGCGGGTG  TCGGGGCTGG  CTTAACTATG  CGGCATCAGA  GCAGATTGTA  CTGAGAGTGC     180
ACCATATGCG  GTGTGAAATA  CCGCACAGAT  GCGTAAGGAG  AAAATACCGC  ATCAGGCGAC     240
GCGCCCTGTA  GCGGCGCATT  AAGCGCGGCG  GGTGTGGTGG  TTACGCGCAG  CGTGACCGCT     300
ACACTTGCCA  GCGCCCTAGC  GCCCGCTCCT  TTCGCTTTCT  TCCCTTCCTT  TCTCGCCACG     360
TTCGCCGGCT  TTCCCCGTCA  AGCTCTAAAT  CGGGGGCTCC  CTTTAGGGTT  CCGATTTAGT     420
GCTTTACGGC  ACCTCGACCC  CAAAAAACTT  GATTAGGGTG  ATGGTTCACG  TAGTGGGCCA     480
TCGCCCTGAT  AGACGGTTTT  TCGCCCTTTG  ACGTTGGAGT  CCACGTTCTT  TAATAGTGGA     540
CTCTTGTTCC  AAACTGGAAC  AACACTCAAC  CCTATCTCGG  TCTATTCTTT  TGATTTATAA     600
GGGATTTTGC  CGATTTCGGC  CTATTGGTTA  AAAAATGAGC  TGATTTAACA  AAAATTTAAC     660
GCGAATTTTA  ACAAAATATT  AACGCTTTAC  AATTTCGCCA  TTCGCCATTC  AGGCTGCGCA     720
ACTGTTGGGA  AGGGCGATCG  GTGCGGGCCT  CTTCGCTATT  ACGCCAGCTG  GCGAAAGGGG     780
```

```
GATGTGCTGC AAGGCGATTA AGTTGGGTAA CGCCAGGGTT TTCCCAGTCA CGACGTTGTA    840

AAACGACGGC CAGTGAATTG TAATACGACT CACTATAGGG CGAATTCGAG CTCGTGAGCC    900

GTATGCGATG AAAGTCGCAC GTACGGTTCT TACCGGGGGA AAACTTGTAA AGGTCTACCT    960

ATCGGGATAC TATGTATTAT CAATGGGTGC TATTTCTCT TTATTTGCAG GATACTACTA    1020

TTGAAGTCCT CAAATTTTAG GTTTAAACTA TAATGAAAAA TTAGCTCAAA TTCAATTCTG    1080

ATTAATTTTC ATTGGGGCTA ATGTTATTTT CTTCCCAATG CATTTCTTAG GTATTAATGG    1140

TATGCCTAGA AGAATTCCTG ATTATCCTGA TGCTTTCGCA GGATGAAATT ATGTCGCTTC    1200

TATTGGTTCA TTCATTGCAC TATTATCATT ATTCTTATTT ATCTATATTT TATATGATCC    1260

TCTAGAGTCG ACCTGCAGCC AAGCTGGGG ATCACATCAT ATGTATATTG TAGGATTAGA    1320

TGCAGATACT AGAGCATATT TCCTATCCGC ACTGATGATT ATTGCAATTC CAACAGGAAT    1380

TAAAATCTTT TCTTGATTAG CCCTGATCTA CGGTGGTTCA ATTAGATTAG CACTACCTAT    1440

GTTATATGCA ATTGCATTCT TATTCTTATT CACAATGGGT GGTTTAACTG GTGTTGCCTT    1500

AGCTAACGCC TCATTAGATG TGGCATTCCA CGATACTTAC TACGTGGTGG ACATTTTCG    1560

AGCGGTCTGA AAGTTATCAT AAATAATATT TACCATATAA TAATGGATAA ATTATATTTT    1620

TATCAATATA AGTCTAATTA CAAGTGTATT AAAATGGTAA CATAAATATG CTAAGCTGTA    1680

ATGACAAAAG TATCCATATT CTTGACAGTT ATTTATATT ATAAAAAAA GATGAAGGAA    1740

CTTTGACTGA TCTAATATGC TCAACGAAAG TGAATCAAAT GTTATAAAAT TACTTACACC    1800

ACTAATTGAA AACCTGTCTG ATATTCAATT ATTATTTATT ATTATATAAT TATATAATAA    1860

TAAATAAAAT GGTTGATGTT ATGTATTGGA AATGAGCATA CGATAAATCA TATAACCATT    1920

AGTAATATAA TTTGAGAGCT AAGTTAGATA TTTACGTATT TATGATAAAA CAGAATAAAC    1980

CCTATAAATT ATTATTATTA ATAATAAAAA ATAATAATAA TACCAATATA TATATTATTT    2040

AATTTATTAT TATTATATTA ATAAAATTTA ATATATATTA TAAATAATTA TTGGATTAAG    2100

AAATATAATA TTTTATAGAA ATTTCTTTA TATTTAGAGG GTAAAAGATT GTATAAAAAG    2160

CTAATGCCAT ATTGTAATGA TATGGATAAG AATTATTATT CTAAAGATGA AAATCTGCTA    2220

ACTTATACTA TAGGGGGGAT CCTCTAGAGT CGACCTGCAG GCATGCAAGC TTTTGTTCCC    2280

TTTAGTGAGG GTTAATTTCG AGCTTGGCGT AATCATGGTC ATAGCTGTTT CCTGTGTGAA    2340

ATTGTTATCC GCTCACAATT CCACACAACA TACGAGCCGG AAGCATAAAG TGTAAAGCCT    2400

GGGGTGCCTA ATGAGTGAGC TAACTCACAT TAATTGCGTT GCGCTCACTG CCCGCTTTCC    2460

AGTCGGGAAA CCTGTCGTGC CAGCTGCATT AATGAATCGG CCAACGCGCG GGAGAGGCG    2520

GTTTGCGTAT TGGGCGCTCT TCCGCTTCCT CGCTCACTGA CTCGCTGCGC TCGGTCGTTC    2580

GGCTGCGGCG AGCGGTATCA GCTCACTCAA AGGCGGTAAT ACGGTTATCC ACAGAATCAG    2640

GGGATAACGC AGGAAAGAAC ATGTGAGCAA AAGGCCAGCA AAAGGCCAGG AACCGTAAAA    2700

AGGCCGCGTT GCTGGCGTTT TTCCATAGGC TCCGCCCCCC TGACGAGCAT CACAAAAATC    2760

GACGCTCAAG TCAGAGGTGG CGAAACCCGA CAGGACTATA AAGATACCAG GCGTTTCCCC    2820

CTGGAAGCTC CCTCGTGCGC TCTCCTGTTC CGACCCTGCC GCTTACCGGA TACCTGTCCG    2880

CCTTTCTCCC TTCGGGAAGC GTGGCGCTTT CTCATAGCTC ACGCTGTAGG TATCTCAGTT    2940

CGGTGTAGGT CGTTCGCTCC AAGCTGGGCT GTGTGCACGA ACCCCCCGTT CAGCCCGACC    3000

GCTGCGCCTT ATCCGGTAAC TATCGTCTTG AGTCCAACCC GGTAAGACAC GACTTATCGC    3060

CACTGGCAGC AGCCACTGGT AACAGGATTA GCAGAGCGAG GTATGTAGGC GGTGCTACAG    3120

AGTTCTTGAA GTGGTGGCCT AACTACGGCT ACACTAGAAG GACAGTATTT GGTATCTGCG    3180
```

-continued

| | | | | | |
|---|---|---|---|---|---|
|CTCTGCTGAA|GCCAGTTACC|TTCGGAAAAA|GAGTTGGTAG|CTCTTGATCC|GGCAAACAAA 3240|
|CCACCGCTGG|TAGCGGTGGT|TTTTTTGTTT|GCAAGCAGCA|GATTACGCGC|AGAAAAAAG 3300|
|GATCTCAAGA|AGATCCTTTG|ATCTTTTCTA|CGGGGTCTGA|CGCTCAGTGG|AACGAAAACT 3360|
|CACGTTAAGG|GATTTTGGTC|ATGAGATTAT|CAAAAAGGAT|CTTCACCTAG|ATCCTTTTAA 3420|
|ATTAAAAATG|AAGTTTTAAA|TCAATCTAAA|GTATATGA|GTAAACTTGG|TCTGACAGTT 3480|
|ACCAATGCTT|AATCAGTGAG|GCACCTATCT|CAGCGATCTG|TCTATTTCGT|TCATCCATAG 3540|
|TTGCCTGACT|CCCCGTCGTG|TAGATAACTA|CGATACGGGA|GGGCTTACCA|TCTGGCCCCA 3600|
|GTGCTGCAAT|GATACCGCGA|GACCCACGCT|CACCGGCTCC|AGATTATCA|GCAATAAACC 3660|
|AGCCAGCCGG|AAGGGCCGAG|CGCAGAAGTG|GTCCTGCAAC|TTTATCCGCC|TCCATCCAGT 3720|
|CTATTAATTG|TTGCCGGGAA|GCTAGAGTAA|GTAGTTCGCC|AGTTAATAGT|TTGCGCAACG 3780|
|TTGTTGCCAT|TGCTACAGGC|ATCGTGGTGT|CACGCTCGTC|GTTTGGTATG|GCTTCATTCA 3840|
|GCTCCGGTTC|CCAACGATCA|AGGCGAGTTA|CATGATCCCC|CATGTTGTGC|AAAAAAGCGG 3900|
|TTAGCTCCTT|CGGTCCTCCG|ATCGTTGTCA|GAAGTAAGTT|GGCCGCAGTG|TTATCACTCA 3960|
|TGGTTATGGC|AGCACTGCAT|AATTCTCTTA|CTGTCATGCC|ATCCGTAAGA|TGCTTTTCTG 4020|
|TGACTGGTGA|GTACTCAACC|AAGTCATTCT|GAGAATAGTG|TATGCGGCGA|CCGAGTTGCT 4080|
|CTTGCCCGGC|GTCAATACGG|GATAATACCG|CGCCACATAG|CAGAACTTTA|AAAGTGCTCA 4140|
|TCATTGGAAA|ACGTTCTTCG|GGGCGAAAAC|TCTCAAGGAT|CTTACCGCTG|TTGAGATCCA 4200|
|GTTCGATGTA|ACCCACTCGT|GCACCCAACT|GATCTTCAGC|ATCTTTTACT|TTCACCAGCG 4260|
|TTTCTGGGTG|AGCAAAAACA|GGAAGGCAAA|ATGCCGCAAA|AAAGGGAATA|AGGGCGACAC 4320|
|GGAAATGTTG|AATACTCATA|CTCTTCCTTT|TTCAATATTA|TTGAAGCATT|TATCAGGGTT 4380|
|ATTGTCTCAT|GAGCGGATAC|ATATTTGAAT|GTATTTAGAA|AAATAAACAA|ATAGGGGTTC 4440|
|CGCGCACATT|TCCCCGAAAA|GTGCCACCTG|ACGTCTAAGA|AACCATTATT|ATCATGACAT 4500|
|TAACCTATAA|AAATAGGCGT|ATCACGAGGC|CCTTTCGTC| |4539|

( 2 ) INFORMATION FOR SEQ ID NO:2:

( i ) SEQUENCE CHARACTERISTICS:
        ( A ) LENGTH: 2939 base pairs
        ( B ) TYPE: nucleic acid
        ( C ) STRANDEDNESS: double
        ( D ) TOPOLOGY: both ( i i ) MOLECULE TYPE: other nucleic acid ( i x ) FEATURE:
        ( A ) NAME/KEY: misc_feature
        ( B ) LOCATION: 2448..2657
        ( D ) OTHER INFORMATION: /product="b-globin exon 2"

( i x ) FEATURE:
        ( A ) NAME/KEY: misc_feature
        ( B ) LOCATION: 2667..2814
        ( D ) OTHER INFORMATION: /product="b-globin exon 1"

( i x ) FEATURE:
        ( A ) NAME/KEY: misc_feature
        ( B ) LOCATION: 2815..2890
        ( D ) OTHER INFORMATION: /product="intron sequence"

( i x ) FEATURE:
        ( A ) NAME/KEY: misc_feature
        ( B ) LOCATION: 2390..2447
        ( D ) OTHER INFORMATION: /product="intron sequence"

( x i ) SEQUENCE DESCRIPTION: SEQ ID NO:2:

-continued

```
TATAGTGTCA CCTAAATCGT ATGTGTATGA TACATAAGGT TATGTATTAA TTGTAGCCGC      60
GTTCTAACGA CAATATGTCC ATATGGTGCA CTCTCAGTAC AATCTGCTCT GATGCCGCAT     120
AGTTAAGCCA GCCCGACAC CCGCCAACAC CCGCTGACGC GCCCTGACGG GCTTGTCTGC      180
TCCCGGCATC CGCTTACAGA CAAGCTGTGA CCGTCTCCGG GAGCTGCATG TGTCAGAGGT     240
TTTCACCGTC ATCACCGAAA CGCGCGAGAC GAAAGGGCCT CGTGATACGC CTATTTTAT     300
AGGTTAATGT CATGATAATA ATGGTTTCTT AGACGTCAGG TGGCACTTTT CGGGGAAATG    360
TGCGCGGAAC CCCTATTTGT TTATTTTTCT AAATACATTC AAATATGTAT CCAGAGTATG    420
AGTATTCAAC ATTTCCGTGT CGCCCTTATT CCCTTTTTG CGAGAGTATG AGTATTCAAC     480
ATTTCCGTGT CGCCCTTATT CCCTTTTTG CGGCATTTTG CCTTCCTGTT TTTGCTCACC     540
CAGAAACGCT GGTGAAAGTA AAAGATGCTG AAGATCAGTT GGGTGCACGA GTGGGTTACA    600
TCGAACTGGA TCTCAACAGC GGTAAGATCC TTGAGAGTTT TCGCCCCGAA GAACGTTTTC    660
CAATGATGAG CACTTTTAAA GTTCTGCTAT GTGGCGCGGT ATTATCCCGT ATTGACGCCG    720
GGCAAGAGCA ACTCGGTCGC CGCATACACT ATTCTCAGAA TGACTTGGTT GAGTACTCAC    780
CAGTCACAGA AAAGCATCTT ACGGATGGCA TGACAGTAAG AGAATTATGC AGTGCTGCCA    840
TAACCATGAG TGATAACACT GCGGCCAACT TACTTCTGAC AACGATCGGA GGACCGAAGG    900
AGCTAACCGC TTTTTTGCAC AACATGGGGG ATCATGTAAC TCGCCTTGAT CGTTGGGAAC    960
CGGAGCTGAA TGAAGCCATA CCAAACGACG AGCGTGACAC CACGATGCCT GTAGCAATGG   1020
CAACAACGTT GCGCAAACTA TTAACTGGCG AACTACTTAC TCTAGCTTCC CGGCAACAAT   1080
TAATAGACTG GATGGAGGCG GATAAAGTTG CAGGACCACT TCTGCGCTCG GCCCTTCCGG   1140
CTGGCTGGTT TATTGCTGAT AAATCTGGAG CCGGTGAGCG TGGGTCTCGC GGTATCATTG   1200
CAGCACTGGG GCCAGATGGT AAGCCCTCCC GTATCGTAGT TATCTACACG ACGGGGAGTC   1260
AGGCAACTAT GGATGAACGA AATAGACAGA TCGCTGAGAT AGGTGCCTCA CTGATTAAGC   1320
ATTGGTAACT GTCAGACCAA GTTACTCAT ATATACTTTA GATTGATTTA AAACTTCATT   1380
TTTAATTTAA AAGGATCTAG GTGAAGATCC TTTTTGATAA TCTCATGACC AAAATCCCTT   1440
AACGTGAGTT TTCGTTCCAC TGAGCGTCAG ACCCCGTAGA AAAGATCAAA GGATCTTCTT   1500
GAGATCCTTT TTTTCTGCGC GTAATCTGCT GCTTGCAAAC AAAAAAACCA CCGCTACCAG   1560
CGGTGGTTTG TTTGCCGGAT CAAGAGCTAC CAACTCTTTT TCCGAAGGTA ACTGGCTTCA   1620
GCAGAGCGCA GATACCAAAT ACTGTCCTTC TAGTGTAGCC GTAGTTAGGC CACCACTTCA   1680
AGAACTCTGT AGCACCGCCT ACATACCTCG CTCTGCTAAT CCTGTTACCA GTGGCTGCTG   1740
CCAGTGGCGA TAAGTCGTGT CTTACCGGGT TGGACTCAAG ACGATAGTTA CCGGATAAGG   1800
CGCAGCGGTC GGGCTGAACG GGGGGTTCGT GCACACAGCC CAGCTTGGAG CGAACGACCT   1860
ACACCGAACT GAGATACCTA CAGCGTGAGC ATTGAGAAAG CGCCACGCTT CCCGAAGGGA   1920
GAAAGGCGGA CAGGTATCCG GTAAGCGGCA GGGTCGGAAC AGGAGAGCGC ACGAGGGAGC   1980
TTCCAGGGGG AAACGCCTGG TATCTTTATA GTCCTGTCGG GTTTCGCCAC CTCTGACTTG   2040
AGCGTCGATT TTTGTGATGC TCGTCAGGGG GGCGGAGCCT ATGGAAAAAC GCCAGCAACG   2100
CGGCCTTTTT ACGGTTCCTG GCCTTTTGCT GGCCTTTTGC TCACATGTTC TTTCCTGCGT   2160
TATCCCCTGA TTCTGTGGAT AACCGTATTA CCGCCTTTGA GTGAGCTGAT ACCGCTCGCC   2220
GCAGCCGAAC GACCGAGCGC AGCGAGTCAG TGAGCGAGGA AGCGGAAGAG CGCCCAATAC   2280
GCAAACCGCC TCTCCCCGCG CGTTGGCCGA TTCATTAATG CAGGTTAACC TGGCTTATCG   2340
AAATTAATAC GACTCACTAT AGGGAGACCG GCCTCGAGCA GCTGAAGCTT TGGGTTTCTG   2400
```

```
ATAGGCACTG  ACTCTCTCTG  CCTATTGGTC  TATTTTCCCA  CCCTTAGGCT  GCTGGTGGTC     2460

TACCCTTGGA  CCCAGAGGTT  CTTTGAGTCC  TTTGGGGATC  TGTCCACTCC  TGATGCTGTT     2520

ATGGGCAACC  CTAAGGTGAA  GGCTCATGGC  AAGAAAGTGC  TCGGTGCCTT  TAGTGATGGC     2580

CTGGCTCACC  TGGACAACCT  CAAGGGCACC  TTTGCCACAC  TGAGTGAGCT  GCACTGTGAC     2640

AAGCTGCACG  TGGATCCCCC  TGAAGCTTGC  TTACATTTGC  TTCTGACACA  ACTGTGTTCA     2700

CTAGCAACCT  CAAACAGACA  CCATGGTGCA  CCTGACTCCT  GAGGAGAAGT  CTGCCGTTAC     2760

TGCCCTGTGG  GGCAAGGTGA  ACGTGGATGA  AGTTGGTGGT  GAGGCCCTGG  GCAGGTTGGT     2820

ATCAAGGTTA  CAAGACAGGT  TTAAGGAGAC  CAATAGAAAC  TGGGCATGTG  GAGACAGAGA     2880

AGACTCTTGG  GATCCCCGGG  TACCGAGCTC  GAATTCATCG  ATGATATCAG  ATCTGGTTC      2939
```

(2) INFORMATION FOR SEQ ID NO:3:

(i) SEQUENCE CHARACTERISTICS:
  (A) LENGTH: 2162 base pairs
  (B) TYPE: nucleic acid
  (C) STRANDEDNESS: double
  (D) TOPOLOGY: both (ii) MOLECULE TYPE: other nucleic acid (ix) FEATURE:
  (A) NAME/KEY: misc_feature
  (B) LOCATION: 82..334
  (D) OTHER INFORMATION: /product="Signal Sequence and Finger-like domain"

(ix) FEATURE:
  (A) NAME/KEY: misc_feature
  (B) LOCATION: 335..447
  (D) OTHER INFORMATION: /product="EGF-like domain"

(ix) FEATURE:
  (A) NAME/KEY: misc_feature
  (B) LOCATION: 448..714
  (D) OTHER INFORMATION: /product="Kringle-1 domain"

(ix) FEATURE:
  (A) NAME/KEY: misc_feature
  (B) LOCATION: 715..972
  (D) OTHER INFORMATION: /product="Kringle-2 domain"

(ix) FEATURE:
  (A) NAME/KEY: misc_feature
  (B) LOCATION: 973..2162
  (D) OTHER INFORMATION: /product="Catalytic domain"

(xi) SEQUENCE DESCRIPTION: SEQ ID NO:3:

```
TGAGCACAGG  GCTGGAGAGA  AAACCTCTGC  GAGGAAAGGG  AAGGAGCAAG  CCGTGAATTT       60

AAGGGACGCT  GTGAAGCAAT  CATGGATGCA  ATGAAGAGAG  GGCTCTGCTG  TGTGCTGCTG      120

CTGTGTGGAG  CAGTCTTCGT  TTCGCCCAGC  CAGGAAATCC  ATGCCCGATT  CAGAAGAGGA      180

GCCAGATCTT  ACCAAGTGAT  CTGCAGAGAT  GAAAAACGC   AGATGATATA  CCAGCAACAT      240

CAGTCATGGC  TGCGCCCTGT  GCTCAGAAGC  AACCGGGTGG  AATATTGCTG  GTGCAACAGT      300

GGCAGGGCAC  AGTGCCACTC  AGTGCCTGTC  AAAAGTTGCA  GCGAGCCAAG  GTGTTTCAAC      360

GGGGGCACCT  GCCAGCAGGC  CCTGTACTTC  TCAGATTTCG  TGTGCCAGTG  CCCCGAAGGA      420

TTTGCTGGGA  AGTGCTGTGA  AATAGATACC  AGGGCCACGT  GCTACGAGGA  CCAGGGCATC      480

AGCTACAGGG  GCACGTGGAG  CACAGCGGAG  AGTGGCGCCG  AGTGCACCAA  CTGGAACAGC      540

AGCGCGTTGG  CCCAGAAGCC  CTACAGCGGG  CGGAGGCCAG  ACGCCATCAG  GCTGGGCCTG      600

GGGAACCACA  ACTACTGCAG  AAACCCAGAT  CGAGACTCAA  AGCCCTGGTG  CTACGTCTTT      660

AAGGCGGGGA  AGTACAGCTC  AGAGTTCTGC  AGCACCCCTG  CCTGCTCTGA  GGGAAACAGT      720
```

| | | | | | | |
|---|---|---|---|---|---|---|
| GACTGCTACT | TTGGGAATGG | GTCAGCCTAC | CGTGGCACGC | ACAGCCTCAC | CGAGTCGGGT | 780 |
| GCCTCCTGCC | TCCCGTGGAA | TTCCATGATC | CTGATAGGCA | AGGTTTACAC | AGCACAGAAC | 840 |
| CCCAGTGCCC | AGGCACTGGG | CCTGGGCAAA | CATAATTACT | GCCGGAATCC | TGATGGGGAT | 900 |
| GCCAAGCCCT | GGTGCCACGT | GCTGAAGAAC | CGCAGGCTGA | CGTGGGAGTA | CTGTGATGTG | 960 |
| CCCTCCTGCT | CCACCTGCGG | CCTGAGACAG | TACAGCCAGC | CTCAGTTTCG | CATCAAAGGA | 1020 |
| GGGCTCTTCG | CCGACATCGC | CTCCCACCCC | TGGCAGGCTG | CCATCTTTGC | CAAGCACAGG | 1080 |
| AGGTCGCCCG | GAGAGCGGTT | CCTGTGCGGG | GGCATACTCA | TCAGCTCCTG | CTGGATTCTC | 1140 |
| TCTGCCGCCC | ACTGCTTCCA | GGAGAGGTTT | CCGCCCCACC | ACCTGACGGT | GATCTTGGGC | 1200 |
| AGAACATACC | GGGTGGTCCC | TGGCGAGGAG | GAGCAGAAAT | TTGAAGTCGA | AAAATACATT | 1260 |
| GTCCATAAGG | AATTCGATGA | TGACACTTAC | GACAATGACA | TTGCGCTGCT | GCAGCTGAAA | 1320 |
| TCGGATTCGT | CCCGCTGTGC | CCAGGAGAGC | AGCGTGGTCC | GCACTGTGTG | CCTTCCCCCG | 1380 |
| GCGGACCTGC | AGCTGCCGGA | CTGGACGGAG | TGTGAGCTCT | CCGGCTACGG | CAAGCATGAG | 1440 |
| GCCTTGTCTC | CTTTCTATTC | GGAGCGGCTG | AAGGAGGCTC | ATGTCAGACT | GTACCCATCC | 1500 |
| AGCCGCTGCA | CATCACAACA | TTTACTTAAC | AGAACAGTCA | CCGACAACAT | GCTGTGTGCT | 1560 |
| GGAGACACTC | GGAGCGGCGG | GCCCCAGGCA | AACTTGCACG | ACGCCTGCCA | GGGCGATTCG | 1620 |
| GGAGGCCCCC | TGGTGTGTCT | GAACGATGGC | CGCATGACTT | TGGTGGGCAT | CATCAGCTGG | 1680 |
| GGCCTGGGCT | GTGGACAGAA | GGATGTCCCG | GGTGTGTACA | CAAAGGTTAC | CAACTACCTA | 1740 |
| GACTGGATTC | GTGACAACAT | GCGACCGTGA | CCAGGAACAC | CCGACTCCTC | AAAAGCAAAT | 1800 |
| GAGATCCCGC | CTCTTCTTCT | TCAGAAGACA | CTGCAAAGGC | GCAGTGCTTC | TCTACAGACT | 1860 |
| TCTCCAGACC | CACCACACCG | CAGAAGCGGG | ACGAGACCCT | ACAGGAGAGG | GAAGAGTGCA | 1920 |
| TTTTCCCAGA | TACTTCCCAT | TTTGGAAGTT | TTCAGGACTT | GGTCTGATTT | CAGGATACTC | 1980 |
| TGTCAGATGG | GAAGACATGA | ATGCACACTA | GCCTCTCCAG | GAATGCCTCC | TCCCTGGGCA | 2040 |
| GAAGTGGCCA | TGCCACCCTG | TTTTCGCTAA | AGCCCAACCT | CCTGACCTGT | CACCGTGAGC | 2100 |
| AGCTTTGGAA | ACAGGACCAC | AAAAATGAAA | GCATGTCTCA | ATAGTAAAAG | AAACAAGAGA | 2160 |
| TC | | | | | | 2162 |

I claim:

1. A combinatorial method for generating a variegated population of ribonucleic acids encoding chimeric gene products, comprising admixing a variegated set of splicing constructs under trans-splicing reaction conditions, each splicing construct comprising a ribonucleic acid represented by the general formula (3'IVS)-EX-(5'IVS), wherein EX represents an exon which is intended to be present in a chimeric ribonucleic acid, said exon having a 5' exon end and a 3' exon end, (3'IVS) is absent or represents a 3' fragment of an intron, which 3' intron fragment is covalently attached to the 5' exon end of said exon by a phosphodiester bond, and (5'IVS) is absent or represents a 5' fragment of an intron, which 5' intron fragment is covalently attached to the 3' exon end of said exon by a phosphodiester bond, with the proviso that at least a portion of said splicing constructs comprise internal exons having both of said 3' and 5' intron fragments; wherein said exons of said set of splicing constructs comprise a variegated population of ribonucleic acids, and said trans-splicing reaction conditions comprise conditions in which 3' and 5' intron fragments of different splicing constructs reconstitute a functional intron through intermolecular complementation and ligate said exons to generate a variegated population of ribonucleic acids encoding chimeric gene products.

2. The method of claim 1, wherein said exons are randomly trans-spliced to each other to generate a library of combinatorial genes comprising, for every N different internal exons, $N^y$ different genes having y internal exons.

3. The method of claim 1, wherein at least a portion of said exons are spliced to each other in predetermined order.

4. The method of claim 1, wherein said 3' and 5' intron fragments of said splicing constructs comprise group II intron fragments including, i) an exon binding site, and ii) a branch site acceptor comprising an activated nucleophile for forming a phosphodiester bond with a 5' intron end of said 5' intron fragment and for cleaving said 5' intron fragment from the 3' end of said exon.

5. The method of claim 4, wherein said group II intron fragments further comprise at least a portion of a group II domain V sufficient to reconstitute said functional intron.

6. The method of claim 4, wherein said trans-splicing reaction conditions further comprise admixing with said splicing constructs at least a portion of a domain V of a group II intron sufficient to interact with said 3' and 5' intron fragments and reconstitute said functional intron.

7. The method of claim 1, wherein said 3' and 5' intron fragments of said splicing constructs comprise group I intron fragments including an internal guide sequence, a GTP-binding site, and a 3' terminal G located in said 3' intron fragment immediately adjacent said 5' exon end of said exon.

8. The method of claim 1, wherein said 3' and 5' intron fragments of said splicing constructs comprise nuclear pre-mRNA intron fragments including a 5' splice junction sequence, a 3' splice junction sequence, and a branchpoint sequence; and said trans-splicing reaction conditions include admixing, with said splicing constructs, adenosine triphosphate (ATP) and small nuclear ribonucleoproteins (snRNPs).

9. The method of claim 8, wherein said snRNPs comprise a U1 snRNP, a U2 snRNP, a U4 snRNP, a U5 snRNP, and a U6 snRNP.

10. The method of claim 1 further comprising the step of reverse transcribing said variegated population of ribonucleic acids encoding chimeric gene products.

11. A combinatorial method for generating a variegated population of ribonucleic acids encoding chimeric gene products, comprising admixing a variegated set of splicing constructs under trans-splicing conditions, each splicing construct comprising a ribonucleic acid represented by the general formula (3'IVS)-EX-(5'IVS), wherein EX represents an exon, said exon having a 5' exon end and a 3' exon end, (3'IVS) is absent or represents a 3' fragment of a group II intron, which 3' intron fragment includes a branch acceptor site and at least a portion of a domain V, and is covalently attached to the 5' exon end of said exon by a phosphodiester bond, and (5'IVS) is absent or represents a 5' fragment of a group II intron, which 5' intron fragment includes an exon binding site, and is covalently attached to the 3' exon end of said exon by a phosphodiester bond, with the proviso that at least a portion of said splicing constructs comprise internal exons having both of said 3' and 5' intron fragments;

wherein said splicing reaction conditions comprise reaction conditions in which said 3' and 5' intron fragments reconstitute a functional intron through intermolecular complementation and trans-splice said exons to generate a variegated library of chimeric ribonucleic acids.

12. The method of claim 11, wherein said branch acceptor site comprises a stem loop structure of a group II domain VI having a branch nucleotide disposed in said 3' intron fragment in the range of 5 to 10 nucleotides from said 5' exon end of said exon and oriented to facilitate nucleophilic attack of its 2'-hydroxyl on a phosphodiester at a 3' exon end of another of said exons.

13. The method of claim 12, wherein said branch nucleotide is an unbase-paired adenosine residue bulging from said stem loop structure of said domain VI.

14. The method of claim 11, wherein said exon binding site comprises from 3 to 8 consecutive nucleotides complementary in sequence to an internal binding sequence located within said exon and proximate to said 3' exon end.

15. The method of claim 11, wherein said 5' intron fragment comprises intron domains V and VI, and said 3' intron fragment comprises intron domains I– III.

16. A method of isolating a gene for chimeric gene product having a desired activity, comprising the steps of:

(i) admixing a variegated population of splicing constructs under trans-splicing reaction conditions, each splicing construct comprising a ribonucleic acid represented by the general formula (3'IVS)-EX-(5'IVS), wherein EX represents an exon, said exon having a 5' exon end and a 3' exon end, (3'IVS) is absent or represents a 3' fragment of an intron, which 3' intron fragment is covalently attached to the 5' exon end of said exon by a phosphodiester bond, and (5'IVS) is absent or represents a 5' fragment of an intron, which 5' intron fragment is covalently attached to the 3' exon end of said exon by a phosphodiester bond, with the proviso that at least a portion of said splicing constructs comprise internal exons having both of said 3' and 5' intron fragments;

wherein said trans-splicing reaction conditions comprise reaction conditions in which said 3' and 5' intron fragments reconstitute a functional intron through intermolecular complementation, which functional intron, under said trans-splicing conditions, causes ligation of said exons to generate a combinatorial library of chimeric ribonucleic acids;

(ii) generating, from said library of chimeric ribonucleic acids, a library of replicable expression vectors;

(iii) transforming suitable host cells with said library of replicable expression vectors;

(iv) culturing said transformed host cells under conditions causing expression of said library of expression vectors to generate a library of gene products;

(v) detecting, in said library of gene products, individual gene products having a desired activity; and (vi) isolating, from said library of expression vectors, genes for the gene products detected in step (v).

17. The method of claim 16, wherein said 3' and 5' intron fragments comprise group II intron fragments including an exon binding site, a branch acceptor site, and at least a potion of a domain V.

18. The method of claim 16, wherein said 3' and 5' intron fragments comprise group I intron fragments including an internal guide sequence, a GTP-binding site, and a guanosine nucleotide located in said 3' intron fragment immediately adjacent said 5' exon end.

19. The method of claim 16, wherein (i) said 3' and 5' intron fragments comprise nuclear pre-mRNA intron fragments including a 5' splice junction sequence, a 3' splice junction sequence, and a branchpoint sequence; and (ii) said trans-splicing reaction conditions include admixing, with said splicing constructs, adenosine triphosphate (ATP) and small nuclear ribonucleoproteins (snRNPs).

20. The method of claim 16, wherein said gene product is a polypeptide.

21. The method of claim 16, wherein said gene product is a ribozyme.

22. The method of claim 16, wherein said desired activity is an enzymatic activity and detecting said desired activity comprises detecting an enzymatic alteration of a substrate by individual gene products of said library of gene products.

23. The method of claim 16, wherein said desired activity is a binding affinity for a target molecule and detecting said desired activity comprises detecting binding to said target molecule by individual gene products of said library of gene products.

24. The method of claim 23, wherein said gene product is an antibody or functional binding fragment thereof.

25. The method of claim 16, wherein said library of replicable expression vectors comprises a phage display library.

26. A splicing construct comprising a nucleic acid represented by the general Formula (3' IVS)-EX-(5' IVS), wherein EX represents an exon, said exon having a 5' exon end and a 3' exon end, (3' IVS) represents a 3' fragment of an intron not normally associated with said exon, which 3' intron fragment is covalently attached to the 5' exon end of said exon by a phosphodiester bond, and (5' IVS) represents a 5' fragment of an intron not normally associated with said exon, which 5' intron fragment is covalently attached to the 3' exon end of said exon by a phosphodiester bond, wherein said exon is discontinuous with any nucleic acid sequences other than said 3' and 5' intron fragments, and said 3' and 5' intron fragments can, through intermolecular complementation, mediate trans-splicing reactions between two or more of said splicing constructs.

27. The nucleic acid construct of claim 26, wherein said exon comprises an open reading frame encoding at least a portion of a protein.

28. The nucleic acid construct of claim 27, wherein said protein is naturally encoded by genomic DNA of a eukaryotic cell.

29. The nucleic acid construct of claim 26, wherein said exon comprises at least a portion of a ribozyme nucleic acid sequence.

30. The nucleic acid construct of claim 26, wherein said 3' and 5' intron fragments comprise group II intron fragments.

31. The nucleic acid construct of claim 26, wherein said 3' and 5' intron fragments comprise group I intron fragments.

32. The nucleic acid construct of claim 26, wherein said 3' and 5' intron fragments comprise nuclear pre-mRNA intron fragments.

33. A library of splicing constructs comprising a variegated population of nucleic acids each represented by the general formula (3' IVS)-EX-(5' IVS), wherein EX represents an exon, said exon having a 5' exon end and a 3' exon end, (3' IVS) represents a 3' fragment of an intron not normally associated with said exon, which 3' intron fragment is covalently attached to the 5' exon end of said exon by a phosphodiester bond, and (5' IVS) represents a 5' fragment of an intron not normally associated with said exon, which 5' intron fragment is covalently attached to the 3' exon end of said exon by a phosphodiester bond, wherein said 3' and 5' intron fragments can, through intermolecular complementation, cause trans-splicing of two or more exons to each other, and said variegated population of nucleic acids is heterogeneous with respect to nucleotide sequences of said exon.

34. The library of splicing constructs of claim 33, wherein exons of said variegated population of nucleic acids encode portions of at least one thrombolytic protein.

35. The library of splicing constructs of claim 33, wherein exons of said variegated population of nucleic acids encode portions of at least one antibody.

36. A kit for humanizing an antibody by combinatorial intron-mediated ligation, comprising a library of human framework region (FR) constructs each represented by the general formula (3'IVS)-FR-(5'IVS), wherein FR represents an exon encoding a human framework region selected from the group consisting of FR1, FR2, FR3 and FR4, said exon having a 5' exon end and a 3' exon end, (3'IVS) is absent or represents a 3' fragment of an intron, which 3' intron fragment is covalently attached to the 5' exon end of said exon by a phosphodiester bond, and (5'IVS) is absent or represents a 5' fragment of an intron, which 5' intron fragment is covalently attached to the 3' exon end of said exon by a phosphodiester bond, with the proviso that one or both of said 3' and 5' intron fragments are present in each FR construct;

wherein said 3' and 5' intron fragments can, through intermolecular complementation, mediate trans-splicing between said exon and a complementarity determining region (CDR) of a construct comprising CDR-encoding nucleic acid having 3' and 5' intron fragments attached thereto.

37. The kit of claim 36, wherein said FR constructs are selected for sequential ligation of said exons with said CDR-encoding nucleic acids to form a ribonucleic acid represented by a general formula 5'-FR1-CDR1-FR2-CDR2-FR3-CDR3-FR4-3'.

* * * * *